(12) United States Patent
Soutschek et al.

(10) Patent No.: US 7,772,200 B2
(45) Date of Patent: Aug. 10, 2010

(54) IRNA AGENTS TARGETED TO THE RHO-A GENE

(75) Inventors: Juergen Soutschek, Kasendorf (DE); Pamela Tan, Kulmbach (DE); Anke Geick, Bayreuth (DE); Hans-Peter Vornlocher, Bayreuth (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/491,367

(22) Filed: Jul. 21, 2006

(65) Prior Publication Data

US 2007/0042984 A1    Feb. 22, 2007

Related U.S. Application Data

(60) Provisional application No. 60/701,470, filed on Jul. 21, 2005, provisional application No. 60/726,838, filed on Oct. 14, 2005, provisional application No. 60/748,316, filed on Dec. 7, 2005.

(51) Int. Cl.
*A61K 31/70* (2006.01)
*C07H 21/04* (2006.01)
*C12N 15/00* (2006.01)
*C12N 5/00* (2006.01)

(52) U.S. Cl. ................ 514/44; 536/24.5; 435/320.1; 435/325

(58) Field of Classification Search .............. None
See application file for complete search history.

(56) References Cited

U.S. PATENT DOCUMENTS

| | | | |
|---|---|---|---|
| 5,328,470 A | 7/1994 | Nabel et al. | |
| 5,624,803 A * | 4/1997 | Noonberg et al. | 435/6 |
| 5,684,133 A | 11/1997 | Schwab et al. | |
| 5,735,814 A | 4/1998 | Elsberry et al. | |
| 5,814,014 A | 9/1998 | Elsberry et al. | |
| 5,858,708 A | 1/1999 | Bandman et al. | |
| 5,945,290 A * | 8/1999 | Cowsert | 435/6 |
| 6,042,579 A | 3/2000 | Elsberry et al. | |
| 6,093,180 A | 7/2000 | Elsberry | |
| 6,107,094 A | 8/2000 | Crooke | |
| 6,410,323 B1 * | 6/2002 | Roberts et al. | 435/375 |
| 6,551,290 B1 | 4/2003 | Elsberry et al. | |
| 6,594,880 B2 | 7/2003 | Elsberry | |
| 6,945,969 B1 | 9/2005 | Morris et al. | |
| 7,189,222 B2 | 3/2007 | Elsberry | |
| 2002/0119140 A1 | 8/2002 | McKerracher et al. | |
| 2003/0124107 A1 | 7/2003 | Minden | |
| 2003/0143732 A1* | 7/2003 | Fosnaugh et al. | 435/325 |
| 2004/0191291 A1 | 9/2004 | Tohyama et al. | |
| 2005/0107325 A1 | 5/2005 | Manoharan et al. | |
| 2007/0031844 A1* | 2/2007 | Khvorova et al. | 435/6 |

FOREIGN PATENT DOCUMENTS

| | | |
|---|---|---|
| EP | 1486564 A1 | 12/2004 |
| WO | WO 90/05191 | 5/1990 |
| WO | WO 99/53945 | 10/1999 |
| WO | WO 01/15739 A1 | 3/2001 |
| WO | WO2004045543 | 6/2004 |
| WO | WO 2004/064737 | 8/2004 |
| WO | WO 2004/080406 | 9/2004 |
| WO | WO 2004/094345 | 11/2004 |
| WO | WO 2004/094595 | 11/2004 |
| WO | WO 2005/015481 | 2/2005 |
| WO | WO 2006/043014 | 4/2006 |

OTHER PUBLICATIONS

Vickers et al. Journal of Biological Chemistry 2003, vol. 278, pp. 7108-7118.*
Opalinska et al. Nature Reviews Drug Discovery, 2002, vol. 1, p. 503-514.*
Elbashir et al. EMBO Journal 2001, vol. 20, pp. 6877-6888.*
Bass Nature 2001, vol. 411, pp. 428-429.*
Vickers et al. Journal of Biological Chemistry 2003, vol. 278, pp. 7108-7118.*
Adamson et al., "Intracellular Localization of the P21$^{rho}$ Proteins", *The Journal of Cell Biology*, 119(3): 617-627 (1992).
Ahmed et al., "Disinhibition of Neurotrophin-Induced Doral Root Ganglion Cell Neurite Outgrowth on CNS Myelin by siRNA-Mediated Knockdown of NgG, p75$^{NTR}$ and Rho-A" *Mol. Cell. Neurosci.* 28: 509-523 (2005).
Allal et al., "RhoA Prenylation is Required for Promotion of Cell Growth and Transformation and Cytoskeleton Organization but Not for Induction of Serum Response Element Transcription", *The Journal of Biological Chemistry*, 276(40): 31001-31008 (2000).
Bishop, A. and Hall, A., "Rho GTPases and Their Effector Proteins" *Biochem. J.* 348: 241-255 (2000).
Byrom et al., "Inducing RNAi with siRNA Cocktails Generated by RNase III", [online] http://www.ambion.com/techlib/tn/101/4.html (2006).
Castelli et al., "A Study of the Interferon Antiviral Mechanism: Apoptosis Activation by the 2-5A System", *The Journal of Experimental Medicine*, 186(6): 967-972 (1997).
Chen et al., "Gene Therapy for Brain Tumors: Regression of Experimental Gliomas by Adenovirus-mediated Gene Transfer in vivo" *Proc. Natl. Acad. Sci.* USA, 91: 3054-3057 (1994).
Dergham et al., "Rho Signaling Pathway Targeted to Promote Spinal Chord Repair" *The Journal of Neuroscience* 22(15): 6570-6577 (2002).
Dubreuil et al., "Rho Activation Patterns After Spinal Chord Injury and the Role of Activated Rho in Apoptosis in the Central Nervous System", *The Journal of Cell Biology* 162(2): 233-243 (2003).
Elbashir et al., "RNA Interference is Mediated by 21- and 22-Nucleotide RNAs", *Genes & Development* 15: 188-200 (2001).
Fire et al., "Potent and Specific Genetic Interference by Double-Stranded RNA in *Caenorhabditis elegans*" *Nature* 391: 806-811 (1998).
Hara et al., "Protein Kinase Inhibition by Fasudil Hysdrochloride Promotes Neurological Recovery After Spinal Cord Injury in Rats" *Journal of Neurosurgery: Spine*, 93 (1): 94-101 (2000).
Heidel et al., "Lack of Interferon Response in Animals to Naked siRNAs" *Nature Biotechnology* 22(12): 1579-1582 (2004).

(Continued)

*Primary Examiner*—Tracy Vivlemore
(74) *Attorney, Agent, or Firm*—Fenwick & West LLP

(57) ABSTRACT

The invention relates to compositions and methods for modulating the expression of the RhoA gene, and more particularly to the downregulation of RhoA by chemically modified oligonucleotides.

5 Claims, 1 Drawing Sheet

OTHER PUBLICATIONS

Karnoub et al., "Molecular Basis for Rho GTPase Signaling Specificity" *Breast Cancer Research and Treatment* 84: 61-71 (2004).
Lee et al., "The Interferon-Induced Double-Stranded RNA-Activated Protein Kinase Induces Apoptosis" *Virology* 199: 491-496 (1994).
Lehmann et al., "Inactivation of Rho Signaling Pathway Promotes CNS Axon Regeneration", *The Journal of Neuroscience* 19(17); 7537-7547 (1999).
Liu et al., "Neuronal and Glial Apoptosis After Traumatic Spinal Chord Injury", *The Journal of Neuroscience* 17(14); 5395-5406 (1997).
Limbach et al., "Summary: The Modified Nucleosides of RNA" *Nucleic Acids Research* 22(12): 2183-2196 (1994).
Manche et al., "Interactions between Double-Stranded RNA Regulators and the Protein Kinase DAI", *Molecular and Cellular Biology* 12(11): 5238-5248 (1992).
Mueller et al., "RHO Kinase, A Promising Drug Target for Neurological Disorders" *Nature Reviews* 4: 387-398(2005).
Nykanen et al., "ATP Requirements and Small Interfering RNA Structure in the RNA Interference Pathway" *Cell* 107: 309-321 (2001).
Schweigreiter et al., "Versican V2 and the Central Inhibitory Domain of Nogo-A Inhibit Neurite Growth Via $p75^{NTR}$/NgR-Independent Pathways That Converge at RhoA" *Mol. Cell. Neurosci.* 27: 163-174 (2004).
Shao, F. and Dixon, J., "YpoT is a Cysteine Protease Cleaving Rho Family GTPases" *Advances in Experimental Medicine and Biology*, 259: 79-84 (2003).
Stamatakis et al., "Isoprenylation of RhoB is Necessary for Its Degradation" *The Journal of Biological Chemistry* 277(51): 49389-49396 (2002).
Wang et al., "P75 Interacts with the Nogo Receptor as a Co-Receptor for Nogo, MAG and 0Mgp," *Nature*, 420:74-78 (2002).
Wheeler, A. and Ridely, A., "Why Three Rho Proteins? RhoA, RhoB. RhoC, and the Cell Motility" *Experimental Cell Research*, 301: 43-49 (2004).
Yang et al., "Short RNA Duplexes Produced by Hydolysis with *Escherichia coli* RNase III Mediate Effective RNA Interference in Mammalian Cells" *PNAS* 99(15): 9942-9947 (2002).
Zheng et al., "Activation of the Protein Kinase PKR by Short Doublr-Stranded RNAs With Single-Stranded Tails" *RNA* 10:1934-1945 (2004).
Genbank Accession No. NM_001664, 28 pages (priority date: Oct. 8, 2006).
Genbank Accession No. NM_016802, 13 pages (priority date: Oct. 1, 2006).
Genbank Accession No. NM_057132, 8 pages (priority date: Oct. 1, 2006).
U.S. Appl. No. 60/574,744, filed May 27, 2004 75 pages.
U.S. Appl. No. 60/559,917, filed Apr. 5, 2004 250 pages.
Schwab, "Molecules Inhibiting Neurite Growth: A Minireview," Neurochem. Res. 21:755-761.
GrandPre et al., "Nogo-66 Receptor Antagonist Peptide Promotes Axonal Regeneration" Nature 417: 547- 551 (2002).
siDirect: siRNA design, "http://design.RNAi.jpl" accessed on May 7, 2008.
Soutschek et al., Therapeutic silencing of an endogenous gene by systemic administration of modified siRNAs, Nov. 2004, Nature, vol. 432, pp. 173-178.
Niederost et al., Nogo-A and myelin-associated glycoprotein mediate neurite growth inhibition by antagonistic regulation of RhoA and Rac1 , Dec. 1, 2002, The Journal of Neuroscience, vol. 22, pp. 10368-10376.
Naito et al., siDirect: highly effective, target-specific siRNA design software for mammalian RNA interference, 2004, Nucleic Acids Research, vol. 32, pp. W124-W129.
Boese, et al., "Mechanistic Insights Aid Computational Short Interfering RNA Design", Methods in Enzymology, vol. 392, 2005,pp. 73-96.
Reynolds, et al. "Rational siRNA Design for RNA Interference", Nature Biotechnology, vol. 22, No. 3, Mar. 2004, pp. 326-330.
Examiner's First Report issued by the Australian Patent Office on Nov. 27, 2008, Australian Patent Application No. 2006272808, 2 pages.
Non-Final Office Action issued by the United States Patent and Trademark Office on Mar. 31, 2009 for U.S. Appl. No. 11/491,440, 11 pages.
Supplementary European Search Report, European Patent Application No. EP 06788187.0, Apr. 14, 2010, 18 Pages.
Dernoanne, C., et al., "Cdc42 downregulates MMP-1 expression by inhibiting the ERK 1/2 pathway," Journal of Cell Science, pp. 1173-1183, vol. 118, No. 6.
Pille, J.-Y., et al., "Anti-RhoA and Anti-RhoC siRNAs inhibit the Proliferation and Invasiveness of MDA-MB-231 Breast Cancer Cells in Vitro and in Vivo," Molecular Therapy, Feb. 2005, pp. 267-274, vol. 11, No. 2.
Office Action for U.S. Appl. No. 11/491,440, Mar. 10, 2010, 16 Pages.

* cited by examiner

Cholesterol-RNA 3'-conjugates

X = S, O

SEQUENCE LISTING

<160> NUMBER OF SEQ ID NOS: 1165

<210> SEQ ID NO 1
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 1
ccggaagaaa cuggugauug uug                                              23

<210> SEQ ID NO 2
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 2
ggaagaaacu ggugauugun n                                                21

<210> SEQ ID NO 3
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 3
acaaucacca guuucuuccn n                                                21

<210> SEQ ID NO 4
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 4
cggaagaaac uggugauugu ugg                                              23

<210> SEQ ID NO 5
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 5
gaagaaacug gugauuguun n                                                21

<210> SEQ ID NO 6
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 6
aacaaucacc aguuucuucn n                                              21

<210> SEQ ID NO 7
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 7
ggaagaaacu ggugauuguu ggu                                            23

<210> SEQ ID NO 8
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 8
aagaaacugg ugauuguugn n                                              21

<210> SEQ ID NO 9
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 9
caacaaucac caguuucuun n                                              21

<210> SEQ ID NO 10
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 10
gaagaaacug gugauuguug gug                                            23

<210> SEQ ID NO 11
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 11
agaaacuggu gauuguuggn n                                              21

<210> SEQ ID NO 12
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 12
ccaacaauca ccaguuucun n                                              21

<210> SEQ ID NO 13
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 13
aagaaacugg ugauuguugg uga                                            23

<210> SEQ ID NO 14
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 14
gaaacuggug auuguuggun n                                              21

<210> SEQ ID NO 15
<211> LENGTH: 21
<212> TYPE: DNA
<213> ORGANISM: Artificial Sequence
<220> FEATURE:
<221> NAME/KEY: misc_feature
<222> LOCATION: 20, 21
<223> OTHER INFORMATION: n = 2'-deoxy-thymidine
<220> FEATURE:
<223> OTHER INFORMATION: Exemplary iRNA agents

<400> SEQUENCE: 15
accaacaauc accaguuucn n                                              21

<210> SEQ ID NO 16
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 16
agaaacuggu gauuguuggu gau                                            23

<210> SEQ ID NO 17
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

<400> SEQUENCE: 17
aaacugguga uuguuggugn n                                              21

<210> SEQ ID NO 18
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 18
caccaacaau caccaguuun n                                              21

<210> SEQ ID NO 19
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 19
gaaacuggug auuguuggug aug                                            23

<210> SEQ ID NO 20
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 20
aacuggugau uguuggugan n                                              21

<210> SEQ ID NO 21
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 21
ucaccaacaa ucaccaguun n                                              21

<210> SEQ ID NO 22
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 22
aaacugguga uuguugguga ugg                                            23

<210> SEQ ID NO 23
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 23
acuggugauu guuggugaun n                                                    21

<210> SEQ ID NO 24
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 24
aucaccaaca aucaccagun n                                                    21

<210> SEQ ID NO 25
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 25
aacuggugau uguuggugau gga                                                  23

<210> SEQ ID NO 26
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 26
cuggugauug uuggugaugn n                                                    21

<210> SEQ ID NO 27
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 27
caucaccaac aaucaccagn n                                                    21

<210> SEQ ID NO 28
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 28
acuggugauu guuggugaug gag                                           23

<210> SEQ ID NO 29
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 29
uggugauugu uggugauggn n                                             21

<210> SEQ ID NO 30
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 30
ccaucaccaa caaucaccan n                                             21

<210> SEQ ID NO 31
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 31
cuggugauug uuggugaugg agc                                           23

<210> SEQ ID NO 32
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 32
ggugauuguu ggugauggan n                                             21

<210> SEQ ID NO 33
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 33
uccaucacca acaaucaccn n                                             21
```

```
<210> SEQ ID NO 34
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 34
uggugauugu uggugaugga gcc                                              23

<210> SEQ ID NO 35
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 35
gugauuguug gugauggagn n                                                21

<210> SEQ ID NO 36
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 36
cuccaucacc aacaaucacn n                                                21

<210> SEQ ID NO 37
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 37
ggugauuguu ggugauggag ccu                                              23

<210> SEQ ID NO 38
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 38
ugauuguugg ugauggagcn n                                                21

<210> SEQ ID NO 39
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 39
gcuccaucac caacaaucan n                                                    21

<210> SEQ ID NO 40
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 40
gaaagacaug cuugcucaua guc                                                  23

<210> SEQ ID NO 41
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 41
aagacaugcu ugcucauagn n                                                    21

<210> SEQ ID NO 42
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 42
cuaugagcaa gcaugucuun n                                                    21

<210> SEQ ID NO 43
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 43
aaagacaugc uugcucauag ucu                                                  23

<210> SEQ ID NO 44
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 44
agacaugcuu gcucauagun n                                                    21
```

<210> SEQ ID NO 45
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 45
acuaugagca agcaugucun n                                          21

<210> SEQ ID NO 46
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 46
aagacaugcu ugcucauagu cuu                                        23

<210> SEQ ID NO 47
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 47
gacaugcuug cucauagucn n                                          21

<210> SEQ ID NO 48
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 48
gacuaugagc aagcaugucn n                                          21

<210> SEQ ID NO 49
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 49
agacaugcuu gcucauaguc uuc                                        23

<210> SEQ ID NO 50
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 50
acaugcuugc ucauagucun n                                               21

<210> SEQ ID NO 51
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 51
agacuaugag caagcaugun n                                               21

<210> SEQ ID NO 52
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 52
gacaugcuug cucauagucu uca                                             23

<210> SEQ ID NO 53
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
<220> FEATURE:
<221> NAME/KEY: misc_feature
<222> LOCATION: 20, 21
<223> OTHER INFORMATION: n = 2'-deoxy-thymidine

<400> SEQUENCE: 53
caugcuugcu cauagucuun n                                               21

<210> SEQ ID NO 54
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 54
aagacuauga gcaagcaugn n                                               21

<210> SEQ ID NO 55
<211> LENGTH: 23
<212> TYPE: RNA
<213> ORGANISM: Artificial Sequence
<220> FEATURE:
<223> OTHER INFORMATION: Exemplary iRNA agents
```

<400> SEQUENCE: 55
acaugcuugc ucauagucuu cag                                          23

<210> SEQ ID NO 56
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 56
augcuugcuc auagucuucn n                                            21

<210> SEQ ID NO 57
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 57
gaagacuaug agcaagcaun n                                            21

<210> SEQ ID NO 58
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 58
caugcuugcu cauagucuuc agc                                          23

<210> SEQ ID NO 59
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 59
ugcuugcuca uagucuucan n                                            21

<210> SEQ ID NO 60
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 60
ugaagacuau gagcaagcan n                                            21

<210> SEQ ID NO 61
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 61
augcuugcuc auagucuuca gca                                              23

<210> SEQ ID NO 62
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 62
gcuugcucau agucuucagn n                                                21

<210> SEQ ID NO 63
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 63
cugaagacua ugagcaagcn n                                                21

<210> SEQ ID NO 64
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 64
ugcuugcuca uagucuucag caa                                              23

<210> SEQ ID NO 65
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 65
cuugcucaua gucuucagcn n                                                21

<210> SEQ ID NO 66
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 66
gcugaagacu augagcaagn n                                              21

<210> SEQ ID NO 67
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 67
gcuugcucau agucuucagc aag                                            23

<210> SEQ ID NO 68
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 68
uugcucauag ucuucagcan n                                              21

<210> SEQ ID NO 69
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 69
ugcugaagac uaugagcaan n                                              21

<210> SEQ ID NO 70
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 70
cuugcucaua gucuucagca agg                                            23

<210> SEQ ID NO 71
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 71
ugcucauagu cuucagcaan n                                              21
```

<210> SEQ ID NO 72
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 72
uugcugaaga cuaugagcan n                                              21

<210> SEQ ID NO 73
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 73
uugcucauag ucuucagcaa gga                                            23

<210> SEQ ID NO 74
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 74
gcucauaguc uucagcaagn n                                              21

<210> SEQ ID NO 75
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 75
cuugcugaag acuaugagcn n                                              21

<210> SEQ ID NO 76
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 76
ugcucauagu cuucagcaag gac                                            23

<210> SEQ ID NO 77
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 77
cucauagucu ucagcaaggn n                                              21

<210> SEQ ID NO 78
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 78
ccuugcugaa gacuaugagn n                                              21

<210> SEQ ID NO 79
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 79
gcucauaguc uucagcaagg acc                                            23

<210> SEQ ID NO 80
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 80
ucauagucuu cagcaaggan n                                              21

<210> SEQ ID NO 81
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 81
uccuugcuga agacuaugan n                                              21

<210> SEQ ID NO 82
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 82
cucauagucu ucagcaagga cca                                            23
```

<210> SEQ ID NO 83
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 83
cauagucuuc agcaaggacn n                                              21

<210> SEQ ID NO 84
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 84
guccuugcug aagacuaugn n                                              21

<210> SEQ ID NO 85
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 85
ucauagucuu cagcaaggac cag                                            23

<210> SEQ ID NO 86
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 86
auagucuuca gcaaggaccn n                                              21

<210> SEQ ID NO 87
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 87
gguccuugcu gaagacuaun n                                              21

<210> SEQ ID NO 88
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 88
cauagucuuc agcaaggacc agu                                              23

<210> SEQ ID NO 89
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 89
uagucuucag caaggaccan n                                                21

<210> SEQ ID NO 90
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 90
ugguccuugc ugaagacuan n                                                21

<210> SEQ ID NO 91
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 91
auagucuuca gcaaggacca guu                                              23

<210> SEQ ID NO 92
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 92
agucuucagc aaggaccagn n                                                21

<210> SEQ ID NO 93
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 93
cugguccuug cugaagacun n                                    21

<210> SEQ ID NO 94
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 94
uagucuucag caaggaccag uuc                                  23

<210> SEQ ID NO 95
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 95
gucuucagca aggaccagun n                                    21

<210> SEQ ID NO 96
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 96
acugguccuu gcugaagacn n                                    21

<210> SEQ ID NO 97
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 97
agucuucagc aaggaccagu ucc                                  23

<210> SEQ ID NO 98
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 98
ucuucagcaa ggaccaguun n                                    21

<210> SEQ ID NO 99
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 99
aacugguccu ugcugaagan n                                              21

<210> SEQ ID NO 100
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 100
gucuucagca aggaccaguu ccc                                            23

<210> SEQ ID NO 101
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 101
cuucagcaag gaccaguucn n                                              21

<210> SEQ ID NO 102
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 102
gaacuggucc uugcugaagn n                                              21

<210> SEQ ID NO 103
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 103
ucuucagcaa ggaccaguuc cca                                            23

<210> SEQ ID NO 104
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

<400> SEQUENCE: 104
uucagcaagg accaguuccn n                                       21

<210> SEQ ID NO 105
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 105
ggaacugguc cuugcugaan n                                       21

<210> SEQ ID NO 106
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 106
cuucagcaag gaccaguucc cag                                     23

<210> SEQ ID NO 107
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 107
ucagcaagga ccaguucccn n                                       21

<210> SEQ ID NO 108
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 108
gggaacuggu ccuugcugan n                                       21

<210> SEQ ID NO 109
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 109
uucagcaagg accaguuccc aga                                     23

<210> SEQ ID NO 110
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 110
cagcaaggac caguucccan n                                            21

<210> SEQ ID NO 111
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 111
ugggaacugg uccuugcugn n                                            21

<210> SEQ ID NO 112
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 112
ucagcaagga ccaguuccca gag                                          23

<210> SEQ ID NO 113
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 113
agcaaggacc aguucccagn n                                            21

<210> SEQ ID NO 114
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 114
cugggaacug guccuugcun n                                            21

<210> SEQ ID NO 115
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 115
cagcaaggac caguucccag agg                                              23

<210> SEQ ID NO 116
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 116
gcaaggacca guucccagan n                                                21

<210> SEQ ID NO 117
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 117
ucugggaacu gguccuugcn n                                                21

<210> SEQ ID NO 118
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 118
agcaaggacc aguucccaga ggu                                              23

<210> SEQ ID NO 119
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 119
caaggaccag uucccagagn n                                                21

<210> SEQ ID NO 120
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 120
cucugggaac ugguccuugn n                                                21
```

<210> SEQ ID NO 121
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 121
gcaaggacca guucccagag gug                                              23

<210> SEQ ID NO 122
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 122
aaggaccagu ucccagaggn n                                                21

<210> SEQ ID NO 123
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 123
ccucugggaa cugguccuun n                                                21

<210> SEQ ID NO 124
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 124
caaggaccag uucccagagg ugu                                              23

<210> SEQ ID NO 125
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 125
aggaccaguu cccagaggun n                                                21

<210> SEQ ID NO 126
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 126
accucuggga acugguccun n                                              21

<210> SEQ ID NO 127
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 127
gaaagcaggu agaguuggcu uug                                            23

<210> SEQ ID NO 128
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 128
aagcagguag aguuggcuun n                                              21

<210> SEQ ID NO 129
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 129
aagccaacuc uaccugcuun n                                              21

<210> SEQ ID NO 130
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 130
aaagcaggua gaguuggcuu ugu                                            23

<210> SEQ ID NO 131
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 131
agcagguaga guuggcuuun n                                              21
```

<210> SEQ ID NO 132
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 132
aaagccaacu cuaccugcun n          21

<210> SEQ ID NO 133
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 133
gacagcccug auaguuuaga aaa          23

<210> SEQ ID NO 134
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 134
cagcccugau aguuuagaan n          21

<210> SEQ ID NO 135
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 135
uucuaaacua ucagggcugn n          21

<210> SEQ ID NO 136
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 136
acagcccuga uaguuuagaa aac          23

<210> SEQ ID NO 137
<211> LENGTH: 21
<212> TYPE: DNA
<213> ORGANISM: Artificial Sequence
<220> FEATURE:
<223> OTHER INFORMATION: Exemplary iRNA agents -continued

```
<220> FEATURE:
<221> NAME/KEY: misc_feature
<222> LOCATION: 20, 21
<223> OTHER INFORMATION: n = 2'-deoxy-thymidine

<400> SEQUENCE: 137
agcccugaua guuuagaaan n                                                    21

<210> SEQ ID NO 138
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 138
uuucuaaacu aucagggcun n                                                    21

<210> SEQ ID NO 139
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 139
cagcccugau aguuuagaaa aca                                                  23

<210> SEQ ID NO 140
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 140
gcccugauag uuuagaaaan n                                                    21

<210> SEQ ID NO 141
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 141
uuuucuaaac uaucagggcn n                                                    21

<210> SEQ ID NO 142
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 142
agcccugaua guuuagaaaa cau                                                  23
```

```
<210> SEQ ID NO 143
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 143
cccugauagu uagaaaacn n                                           21

<210> SEQ ID NO 144
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 144
guuuucuaaa cuaucagggn n                                          21

<210> SEQ ID NO 145
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 145
gcccugauag uuuagaaaac auc                                        23

<210> SEQ ID NO 146
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 146
ccugauaguu uagaaaacan n                                          21

<210> SEQ ID NO 147
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 147
uguuuucuaa acuaucaggn n                                          21

<210> SEQ ID NO 148
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 148
cccugauagu uuagaaaaca ucc                                              23

<210> SEQ ID NO 149
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 149
cugauaguuu agaaaacaun n                                                21

<210> SEQ ID NO 150
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 150 auguuucua aacuaucagn n                                                 21

<210> SEQ ID NO 151
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 151
ccugauaguu uagaaaacau ccc                                              23

<210> SEQ ID NO 152
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 152
ugauaguuua gaaaacaucn n                                                21

<210> SEQ ID NO 153
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 153
gauguuuucu aaacuaucan n                                              21

<210> SEQ ID NO 154
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 154
cugauaguuu agaaaacauc cca                                            23

<210> SEQ ID NO 155
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 155
gauaguuuag aaaacauccn n                                              21

<210> SEQ ID NO 156
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 156
ggauguuuuc uaaacuaucn n                                              21

<210> SEQ ID NO 157
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 157
ugauaguuua gaaaacaucc cag                                            23

<210> SEQ ID NO 158
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 158
auaguuuaga aaacaucccn n                                              21

<210> SEQ ID NO 159
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 159
gggauguuuu cuaaacuaun n                                              21

<210> SEQ ID NO 160
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 160
gauaguuuag aaaacauccc aga                                            23

<210> SEQ ID NO 161
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 161
uaguuuagaa aacaucccan n                                              21

<210> SEQ ID NO 162
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 162
ugggauguuu ucuaaacuan n                                              21

<210> SEQ ID NO 163
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 163
auaguuuaga aaacauccca gaa                                            23

<210> SEQ ID NO 164
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 164
aguuuagaaa acaucccagn n                                    21

<210> SEQ ID NO 165
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 165
cugggauguu uucuaaacun n                                    21

<210> SEQ ID NO 166
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 166
uaguuuagaa aacaucccag aaa                                  23

<210> SEQ ID NO 167
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 167
guuuagaaaa caucccagan n                                    21

<210> SEQ ID NO 168
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 168
ucugggaugu uuucuaaacn n                                    21

<210> SEQ ID NO 169
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 169
aguuuagaaa acaucccaga aaa                                  23

<210> SEQ ID NO 170
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 170
uuuagaaaac aucccagaan n                                              21

<210> SEQ ID NO 171
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 171
uucugggaug uuuucuaaan n                                              21

<210> SEQ ID NO 172
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 172
guuuagaaaa caucccagaa aag                                            23

<210> SEQ ID NO 173
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 173
uuagaaaaca ucccagaaan n                                              21

<210> SEQ ID NO 174
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 174
uuucugggau guuuucuaan n                                              21

<210> SEQ ID NO 175
<211> LENGTH: 23
<212> TYPE: RNA
<213> ORGANISM: Artificial Sequence
<220> FEATURE:
<223> OTHER INFORMATION: Exemplary iRNA agents
```

<400> SEQUENCE: 175
uuuagaaaac aucccagaaa agu                                           23

<210> SEQ ID NO 176
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 176
uagaaaacau cccagaaaan n                                             21

<210> SEQ ID NO 177
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 177
uuuucuggga uguuuucuan n                                             21

<210> SEQ ID NO 178
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 178
ccccagaagu caagcauuuc ugu                                           23

<210> SEQ ID NO 179
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 179
ccagaaguca agcauuucun n                                             21

<210> SEQ ID NO 180
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 180
agaaaugcuu gacuucuggn n                                             21

<210> SEQ ID NO 181
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 181
cccagaaguc aagcauuucu guc                                               23

<210> SEQ ID NO 182
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 182
cagaagucaa gcauuucugn n                                                 21

<210> SEQ ID NO 183
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 183
cagaaaugcu ugacuucugn n                                                 21

<210> SEQ ID NO 184
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 184
ccagaaguca agcauuucug ucc                                               23

<210> SEQ ID NO 185
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 185
agaagucaag cauuucugun n                                                 21

<210> SEQ ID NO 186
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 186
acagaaaugc uugacuucun n                                              21

<210> SEQ ID NO 187
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 187
cagaagucaa gcauuucugu ccc                                            23

<210> SEQ ID NO 188
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 188
gaagucaagc auuucugucn n                                              21

<210> SEQ ID NO 189
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 189
gacagaaaug cuugacuucn n                                              21

<210> SEQ ID NO 190
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 190
agaagucaag cauuucuguc cca                                            23

<210> SEQ ID NO 191
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 191
aagucaagca uuucuguccn n                                              21
```

```
<210> SEQ ID NO 192
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 192
ggacagaaau gcuugacuun n                                              21

<210> SEQ ID NO 193
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 193
ugaaaccuga agaaggcaga gau                                            23

<210> SEQ ID NO 194
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 194
aaaccugaag aaggcagagn n                                              21

<210> SEQ ID NO 195
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 195
cucugccuuc uucagguuun n                                              21

<210> SEQ ID NO 196
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 196
gaaaccugaa gaaggcagag aua                                            23

<210> SEQ ID NO 197
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 197
aaccugaaga aggcagagan n                                              21

<210> SEQ ID NO 198
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 198
ucucugccuu cuucagguun n                                              21

<210> SEQ ID NO 199
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 199
aaaccugaag aaggcagaga uau                                            23

<210> SEQ ID NO 200
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 200
accugaagaa ggcagagaun n                                              21

<210> SEQ ID NO 201
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 201
aucucugccu ucuucaggun n                                              21

<210> SEQ ID NO 202
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 202
aaccugaaga aggcagagau aug                                            23
```

-continued

<210> SEQ ID NO 203
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 203
ccugaagaag gcagagauan n                                              21

<210> SEQ ID NO 204
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 204
uaucucugcc uucuucaggn n                                              21

<210> SEQ ID NO 205
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 205
accugaagaa ggcagagaua ugg                                            23

<210> SEQ ID NO 206
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 206
cugaagaagg cagagauaun n                                              21

<210> SEQ ID NO 207
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 207
auaucucugc cuucuucagn n                                              21

<210> SEQ ID NO 208
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 208
ccugaagaag gcagagauau ggc                                              23

<210> SEQ ID NO 209
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 209
ugaagaaggc agagauaugn n                                                21

<210> SEQ ID NO 210
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 210
cauaucucug ccuucuucan n                                                21

<210> SEQ ID NO 211
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 211
cugaagaagg cagagauaug gca                                              23

<210> SEQ ID NO 212
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 212
gaagaaggca gagauauggn n                                                21

<210> SEQ ID NO 213
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 213
ccauaucucu gccuucuucn n                                              21

<210> SEQ ID NO 214
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 214
ugaagaaggc agagauaugg caa                                            23

<210> SEQ ID NO 215
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 215
aagaaggcag agauauggcn n                                              21

<210> SEQ ID NO 216
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 216
gccauaucuc ugccuucuun n                                              21

<210> SEQ ID NO 217
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 217
gaagaaggca gagauauggc aaa                                            23

<210> SEQ ID NO 218
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 218
agaaggcaga gauauggcan n                                              21

<210> SEQ ID NO 219
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 219
ugccauaucu cugccuucun n                                              21

<210> SEQ ID NO 220
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 220
aagaaggcag agauauggca aac                                            23

<210> SEQ ID NO 221
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 221
gaaggcagag auauggcaan n                                              21

<210> SEQ ID NO 222
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 222
uugccauauc ucugccuucn n                                              21

<210> SEQ ID NO 223
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 223
agaaggcaga gauauggcaa aca                                            23

<210> SEQ ID NO 224
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

<400> SEQUENCE: 224
aaggcagaga uauggcaaan n                                              21

<210> SEQ ID NO 225
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 225
uuugccauau cucugccuun n                                              21

<210> SEQ ID NO 226
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 226
gaaggcagag auauggcaaa cag                                            23

<210> SEQ ID NO 227
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 227
aggcagagau auggcaaacn n                                              21

<210> SEQ ID NO 228
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 228
guuugccaua ucucugccun n                                              21

<210> SEQ ID NO 229
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 229
aaggcagaga uauggcaaac agg                                            23

<210> SEQ ID NO 230
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 230
ggcagagaua uggcaaacan n                                              21

<210> SEQ ID NO 231
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 231
uguuugccau aucucugccn n                                              21

<210> SEQ ID NO 232
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 232
aggcagagau auggcaaaca gga                                            23

<210> SEQ ID NO 233
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 233
gcagagauau ggcaaacagn n                                              21

<210> SEQ ID NO 234
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 234
cuguuugcca uaucucugcn n                                              21

<210> SEQ ID NO 235
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 235
ggcagagaua uggcaaacag gau                                              23

<210> SEQ ID NO 236
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 236
cagagauaug gcaaacaggn n                                                21

<210> SEQ ID NO 237
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 237
ccuguuugcc auaucucugn n                                                21

<210> SEQ ID NO 238
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 238
gcagagauau ggcaaacagg auu                                              23

<210> SEQ ID NO 239
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 239
agagauaugg caaacaggan n                                                21

<210> SEQ ID NO 240
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 240
uccuguuugc cauaucucun n                                                21
```

```
<210> SEQ ID NO 241
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 241
cagagauaug gcaaacagga uug                                               23

<210> SEQ ID NO 242
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 242
gagauauggc aaacaggaun n                                                 21

<210> SEQ ID NO 243
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 243
auccuguuug ccauaucucn n                                                 21

<210> SEQ ID NO 244
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 244
agagauaugg caaacaggau ugg                                               23

<210> SEQ ID NO 245
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 245
agauauggca aacaggauun n                                                 21

<210> SEQ ID NO 246
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 246
aauccuguuu gccauaucun n                                                    21

<210> SEQ ID NO 247
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 247
gagauauggc aaacaggauu ggc                                                  23

<210> SEQ ID NO 248
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 248
gauauggcaa acaggauugn n                                                    21

<210> SEQ ID NO 249
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 249
caauccuguu ugccauaucn n                                                    21

<210> SEQ ID NO 250
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 250
agauauggca aacaggauug gcg                                                  23

<210> SEQ ID NO 251
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 251
auauggcaaa caggauuggn n                                                    21
```

```
<210> SEQ ID NO 252
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 252
ccaauccugu uugccauaun n                                         21

<210> SEQ ID NO 253
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 253
gauauggcaa acaggauugg cgc                                       23

<210> SEQ ID NO 254
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 254
uauggcaaac aggauuggcn n                                         21

<210> SEQ ID NO 255
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 255
gccaauccug uuugccauan n                                         21

<210> SEQ ID NO 256
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 256
auauggcaaa caggauuggc gcu                                       23

<210> SEQ ID NO 257
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 257
auggcaaaca ggauuggcgn n                                                 21

<210> SEQ ID NO 258
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 258
cgccaauccu guuugccaun n                                                 21

<210> SEQ ID NO 259
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 259
uauggcaaac aggauuggcg cuu                                               23

<210> SEQ ID NO 260
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 260
uggcaaacag gauuggcgcn n                                                 21

<210> SEQ ID NO 261
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 261
gcgccaaucc uguuugccan n                                                 21

<210> SEQ ID NO 262
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 262
auggcaaaca ggauuggcgc uuu                                               23
```

```
<210> SEQ ID NO 263
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 263
ggcaaacagg auuggcgcun n                                              21

<210> SEQ ID NO 264
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 264
agcgccaauc cuguuugccn n                                              21

<210> SEQ ID NO 265
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 265
uggcaaacag gauuggcgcu uuu                                            23

<210> SEQ ID NO 266
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 266
gcaaacagga uuggcgcuun n                                              21

<210> SEQ ID NO 267
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 267
aagcgccaau ccuguuugcn n                                              21

<210> SEQ ID NO 268
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 268
ggcaaacagg auuggcgcuu uug                                             23

<210> SEQ ID NO 269
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 269
caaacaggau uggcgcuuun n                                               21

<210> SEQ ID NO 270
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 270
aaagcgccaa uccuguuugn n                                               21

<210> SEQ ID NO 271
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 271
gcaaacagga uuggcgcuuu ugg                                             23

<210> SEQ ID NO 272
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 272
aaacaggauu ggcgcuuuun n                                               21

<210> SEQ ID NO 273
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 273
aaaagcgcca auccuguuun n                                         21

<210> SEQ ID NO 274
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 274
caaacaggau uggcgcuuuu ggg                                       23

<210> SEQ ID NO 275
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 275
aacaggauug gcgcuuuugn n                                         21

<210> SEQ ID NO 276
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 276
caaaagcgcc aauccuguun n                                         21

<210> SEQ ID NO 277
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 277
aaacaggauu ggcgcuuuug gu                                        23

<210> SEQ ID NO 278
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 278
acaggauugg cgcuuuuggn n                                         21

<210> SEQ ID NO 279
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 279
ccaaaagcgc caauccugun n                                          21

<210> SEQ ID NO 280
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 280
aacaggauug gcgcuuuugg gua                                        23

<210> SEQ ID NO 281
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 281
caggauuggc gcuuuugggn n                                          21

<210> SEQ ID NO 282
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 282
cccaaaagcg ccaauccugn n                                          21

<210> SEQ ID NO 283
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 283
acaggauugg cgcuuuuggg uac                                        23

<210> SEQ ID NO 284
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

<400> SEQUENCE: 284
aggauuggcg cuuuugggun n                                              21

<210> SEQ ID NO 285
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 285
acccaaaagc gccaauccun n                                              21

<210> SEQ ID NO 286
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 286
caggauuggc gcuuuugggu aca                                            23

<210> SEQ ID NO 287
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 287
ggauuggcgc uuuuggguan n                                              21

<210> SEQ ID NO 288
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 288
uacccaaaag cgccaauccn n                                              21

<210> SEQ ID NO 289
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 289
aggauuggcg cuuuugggua cau                                            23

<210> SEQ ID NO 290
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 290
gauuggcgcu uuggguacn n                                              21

<210> SEQ ID NO 291
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 291
guacccaaaa gcgccaaucn n                                             21

<210> SEQ ID NO 292
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 292
ggauuggcgc uuuugggauc aug                                           23

<210> SEQ ID NO 293
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 293
auuggcgcuu uuggguacan n                                             21

<210> SEQ ID NO 294
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 294
uguacccaaa agcgccaaun n                                             21

<210> SEQ ID NO 295
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 295
gauuggcgcu uuuggguaca ugg                                          23

<210> SEQ ID NO 296
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 296
uuggcgcuuu uggguacaun n                                            21

<210> SEQ ID NO 297
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 297
auguacccaa aagcgccaan n                                            21

<210> SEQ ID NO 298
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 298
auuggcgcuu uugguacau gga                                           23

<210> SEQ ID NO 299
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 299
uggcgcuuuu ggguacaugn n                                            21

<210> SEQ ID NO 300
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 300
cauguaccca aaagcgccan n                                            21
```

<210> SEQ ID NO 301
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 301
uuggcgcuuu uggguacaug gag                                              23

<210> SEQ ID NO 302
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 302
ggcgcuuuug gguacauggn n                                                21

<210> SEQ ID NO 303
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 303
ccauguaccc aaaagcgccn n                                                21

<210> SEQ ID NO 304
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 304
uggcgcuuuu ggguacaugg agu                                              23

<210> SEQ ID NO 305
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 305
gcgcuuuugg guacauggan n                                                21

<210> SEQ ID NO 306
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 306
uccauguacc caaaagcgcn n                                              21

<210> SEQ ID NO 307
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 307
ggcgcuuuug gguacaugga gug                                            23

<210> SEQ ID NO 308
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 308
cgcuuuuggg uacauggagn n                                              21

<210> SEQ ID NO 309
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 309
cuccauguac ccaaaagcgn n                                              21

<210> SEQ ID NO 310
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 310
gcgcuuuugg guacauggag ugu                                            23

<210> SEQ ID NO 311
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 311
gcuuuugggu acauggagun n                                              21
```

```
<210> SEQ ID NO 312
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 312
acuccaugua cccaaaagcn n                                              21

<210> SEQ ID NO 313
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 313 cgcuuuggg uacauggagu guu                                             23

<210> SEQ ID NO 314
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 314
cuuuugggua cauggagugn n                                              21

<210> SEQ ID NO 315
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 315
cacuccaugu acccaaaagn n                                              21

<210> SEQ ID NO 316
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 316 gcuuuggu acauggagug uuc                                              23

<210> SEQ ID NO 317
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 317 uuuugggguac auggagugun n                                             21

<210> SEQ ID NO 318
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 318
acacuccaug uacccaaaan n                                              21

<210> SEQ ID NO 319
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 319
cuuuugggua cauggagugu uca                                            23

<210> SEQ ID NO 320
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 320 uuugggguaca uggaguguun n                                             21

<210> SEQ ID NO 321
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 321
aacacuccau guacccaaan n                                              21

<210> SEQ ID NO 322
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 322 uuuugggguac auggaguguu cag                                           23
```

```
<210> SEQ ID NO 323
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 323
uuggguacau ggaguguucn n                                              21

<210> SEQ ID NO 324
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 324
gaacacucca uguacccaan n                                              21

<210> SEQ ID NO 325
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 325 uuugggguaca uggaguguuc agc                                           23

<210> SEQ ID NO 326
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 326
uggguacaug gaguguucan n                                              21

<210> SEQ ID NO 327
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 327
ugaacacucc auguacccan n                                              21

<210> SEQ ID NO 328
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 328 uugggua cau ggaguguuca gca                                              23

<210> SEQ ID NO 329
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 329
ggguacaugg aguguucagn n                                                 21

<210> SEQ ID NO 330
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 330
cugaacacuc cauguacccn n                                                 21

<210> SEQ ID NO 331
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 331
uggguacaug gaguguucag caa                                               23

<210> SEQ ID NO 332
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 332
gguacaugga guguucagcn n                                                 21

<210> SEQ ID NO 333
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 333
gcugaacacu ccauguaccn n          21

<210> SEQ ID NO 334
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 334
ggguacaugg aguguucagc aaa          23

<210> SEQ ID NO 335
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 335
guacauggag uguucagcan n          21

<210> SEQ ID NO 336
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 336
ugcugaacac uccauguacn n          21

<210> SEQ ID NO 337
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 337
gguacaugga guguucagca aag          23

<210> SEQ ID NO 338
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 338
uacauggagu guucagcaan n          21

<210> SEQ ID NO 339
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 339
uugcugaaca cuccauguan n                                           21

<210> SEQ ID NO 340
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 340
guacauggag uguucagcaa aga                                         23

<210> SEQ ID NO 341
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 341
acauggagug uucagcaaan n                                           21

<210> SEQ ID NO 342
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 342
uuugcugaac acuccaugun n                                           21

<210> SEQ ID NO 343
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 343
uacauggagu guucagcaaa gac                                         23

<210> SEQ ID NO 344
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 344
cauggagugu ucagcaaagn n                                              21

<210> SEQ ID NO 345
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 345
cuuugcugaa cacuccaugn n                                              21

<210> SEQ ID NO 346
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 346
acauggagug uucagcaaag acc                                            23

<210> SEQ ID NO 347
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 347
auggaguguu cagcaaagan n                                              21

<210> SEQ ID NO 348
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 348
ucuuugcuga acacuccaun n                                              21

<210> SEQ ID NO 349
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 349
cauggagugu ucagcaaaga cca                                            23

<210> SEQ ID NO 350
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 350
uggaguguuc agcaaagacn n                                              21

<210> SEQ ID NO 351
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 351
gucuuugcug aacacuccan n                                              21

<210> SEQ ID NO 352
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 352
auggaguguu cagcaaagac caa                                            23

<210> SEQ ID NO 353
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 353
ggaguguuca gcaaagaccn n                                              21

<210> SEQ ID NO 354
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 354
ggucuuugcu gaacacuccn n                                              21

<210> SEQ ID NO 355
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 355
uggaguguuc agcaaagacc aaa                                              23

<210> SEQ ID NO 356
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 356
gaguguucag caaagaccan n                                                21

<210> SEQ ID NO 357
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 357
uggucuuugc ugaacacucn n                                                21

<210> SEQ ID NO 358
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 358
ggaguguuca gcaaagacca aag                                              23

<210> SEQ ID NO 359
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 359
aguguucagc aaagaccaan n                                                21

<210> SEQ ID NO 360
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 360
uuggucuuug cugaacacun n                                                21
```

```
<210> SEQ ID NO 361
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 361
gaguguucag caaagaccaa aga                                              23

<210> SEQ ID NO 362
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 362
guguucagca aagaccaaan n                                                21

<210> SEQ ID NO 363
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 363
uuuggucuuu gcugaacacn n                                                21

<210> SEQ ID NO 364
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 364
aguguucagc aaagaccaaa gau                                              23

<210> SEQ ID NO 365
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 365
uguucagcaa agaccaaagn n                                                21

<210> SEQ ID NO 366
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 366
cuuuggucuu ugcugaacan n                                              21

<210> SEQ ID NO 367
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 367
guguucagca aagaccaaag aug                                            23

<210> SEQ ID NO 368
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 368
guucagcaaa gaccaaagan n                                              21

<210> SEQ ID NO 369
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 369
ucuuuggucu uugcugaacn n                                              21

<210> SEQ ID NO 370
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 370
auggagugag agagguuuuu gaa                                            23

<210> SEQ ID NO 371
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 371
ggagugagag agguuuuugn n                                              21
```

-continued

<210> SEQ ID NO 372
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 372
caaaaaccuc ucucacuccn n                                              21

<210> SEQ ID NO 373
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 373
uggagugaga gagguuuuug aaa                                            23

<210> SEQ ID NO 374
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 374
gagugagaga gguuuuugan n                                              21

<210> SEQ ID NO 375
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 375
ucaaaaaccu cucucacucn n                                              21

<210> SEQ ID NO 376
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 376
cuacgagagc ugcucugcaa gcu                                            23

<210> SEQ ID NO 377
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 377
acgagagcug cucugcaagn n                                         21

<210> SEQ ID NO 378
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 378
cuugcagagc agcucucgun n                                         21

<210> SEQ ID NO 379
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 379
uacgagagcu gcucugcaag cua                                       23

<210> SEQ ID NO 380
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 380
cgagagcugc ucugcaagcn n                                         21

<210> SEQ ID NO 381
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 381
gcuugcagag cagcucucgn n                                         21

<210> SEQ ID NO 382
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 382
acgagagcug cucugcaagc uag                                       23
```

<210> SEQ ID NO 383
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 383
gagagcugcu cugcaagcun n                                      21

<210> SEQ ID NO 384
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 384
agcuugcaga gcagcucucn n                                      21

<210> SEQ ID NO 385
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 385
cgagagcugc ucugcaagcu aga                                    23

<210> SEQ ID NO 386
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 386
agagcugcuc ugcaagcuan n                                      21

<210> SEQ ID NO 387
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 387
uagcuugcag agcagcucun n                                      21

<210> SEQ ID NO 388
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 388
gagagcugcu cugcaagcua gac                                          23

<210> SEQ ID NO 389
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 389
gagcugcucu gcaagcuagn n                                            21

<210> SEQ ID NO 390
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 390
cuagcuugca gagcagcucn n                                            21

<210> SEQ ID NO 391
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 391
agagcugcuc ugcaagcuag acg                                          23

<210> SEQ ID NO 392
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 392
agcugcucug caagcuagan n                                            21

<210> SEQ ID NO 393
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 393
ucuagcuugc agagcagcun n                                              21

<210> SEQ ID NO 394
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 394
gagcugcucu gcaagcuaga cgu                                            23

<210> SEQ ID NO 395
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 395
gcugcucugc aagcuagacn n                                              21

<210> SEQ ID NO 396
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 396
gucuagcuug cagagcagcn n                                              21

<210> SEQ ID NO 397
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 397
agcugcucug caagcuagac gug                                            23

<210> SEQ ID NO 398
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 398
cugcucugca agcuagacgn n                                              21

<210> SEQ ID NO 399
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 399
cgucuagcuu gcagagcagn n                                              21

<210> SEQ ID NO 400
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 400
uugaagugcu guuuauuaau cuu                                            23

<210> SEQ ID NO 401
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 401
gaagugcugu uuauuaaucn n                                              21

<210> SEQ ID NO 402
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 402
gauuaauaaa cagcacuucn n                                              21

<210> SEQ ID NO 403
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 403
ugaagugcug uuuauuaauc uua                                            23

<210> SEQ ID NO 404
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 404
aagugcuguu uauuaaucun n                                      21

<210> SEQ ID NO 405
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 405
agauuaauaa acagcacuun n                                      21

<210> SEQ ID NO 406
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 406
gaagugcugu uuauuaaucu uag                                    23

<210> SEQ ID NO 407
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 407
agugcuguuu auuaaucuun n                                      21

<210> SEQ ID NO 408
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 408
aagauuaaua aacagcacun n                                      21

<210> SEQ ID NO 409
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 409
aagugcuguu uauuaaucuu agu                                    23

<210> SEQ ID NO 410
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 410
gugcuguuua uuaaucuuan n                                            21

<210> SEQ ID NO 411
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 411
uaagauuaau aaacagcacn n                                            21

<210> SEQ ID NO 412
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 412
agugcuguuu auuaaucuua gug                                          23

<210> SEQ ID NO 413
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 413
ugcuguuuau uaaucuuagn n                                            21

<210> SEQ ID NO 414
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 414
cuaagauuaa uaaacagcan n                                            21

<210> SEQ ID NO 415
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 415
gugcuguuua uuaaucuuag ugu                                            23

<210> SEQ ID NO 416
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 416
gcuguuuauu aaucuuagun n                                              21

<210> SEQ ID NO 417
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 417
acuaagauua auaaacagcn n                                              21

<210> SEQ ID NO 418
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 418
ugcuguuuau uaaucuuagu gua                                            23

<210> SEQ ID NO 419
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 419
cuguuuauua aucuuagugn n                                              21

<210> SEQ ID NO 420
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 420
cacuaagauu aauaaacagn n                                              21
```

<210> SEQ ID NO 421
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 421
gcuguuuauu aaucuuagug uau                                              23

<210> SEQ ID NO 422
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 422
uguuuauuaa ucuuagugun n                                                21

<210> SEQ ID NO 423
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 423
acacuaagau uaauaaacan n                                                21

<210> SEQ ID NO 424
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 424
cuguuuauua aucuuagugu aug                                              23

<210> SEQ ID NO 425
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 425
guuuauuaau cuuaguguan n                                                21

<210> SEQ ID NO 426
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 426
uacacuaaga uuaauaaacn n                                              21

<210> SEQ ID NO 427
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 427
uguuuauuaa ucuuagugua uga                                            23

<210> SEQ ID NO 428
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 428
uuuauuaauc uuaguguaun n                                              21

<210> SEQ ID NO 429
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 429
auacacuaag auuaauaaan n                                              21

<210> SEQ ID NO 430
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 430
guuuauuaau cuuaguguau gau                                            23

<210> SEQ ID NO 431
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 431
uuauuaaucu aguguaugn n                                               21
```

<210> SEQ ID NO 432
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 432
cauacacuaa gauuaauaan n                                         21

<210> SEQ ID NO 433
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 433
uuuauuaauc uuaguguaug auu                                       23

<210> SEQ ID NO 434
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 434
uauuaaucuu aguguaugan n                                         21

<210> SEQ ID NO 435
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 435
ucauacacua agauuaauan n                                         21

<210> SEQ ID NO 436
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 436
uuauuaaucu uaguguauga uua                                       23

<210> SEQ ID NO 437
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 437
auuaaucuua guguaugaun n                                              21

<210> SEQ ID NO 438
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 438
aucauacacu aagauuaaun n                                              21

<210> SEQ ID NO 439
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 439
uauuaaucuu aguguaugau uac                                            23

<210> SEQ ID NO 440
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 440
uuaaucuuag uguaugauun n                                              21

<210> SEQ ID NO 441
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 441
aaucauacac uaagauuaan n                                              21

<210> SEQ ID NO 442
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 442
auuaaucuua guguaugauu acu                                            23
```

```
<210> SEQ ID NO 443
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 443
uaaucuuagu guaugauuan n                                               21

<210> SEQ ID NO 444
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 444
uaaucauaca cuaagauuan n                                               21

<210> SEQ ID NO 445
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 445
uuaaucuuag uguaugauua cug                                             23

<210> SEQ ID NO 446
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 446
aaucuuagug uaugauuacn n                                               21

<210> SEQ ID NO 447
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 447
guaaucauac acuaagauun n                                               21

<210> SEQ ID NO 448
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 448
uaaucuuagu guaugauuac ugg                                              23

<210> SEQ ID NO 449
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 449
aucuuagugu augauuacun n                                                21

<210> SEQ ID NO 450
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 450
aguaaucaua cacuaagaun n                                                21

<210> SEQ ID NO 451
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 451
aaucuuagug uaugauuacu ggc                                              23

<210> SEQ ID NO 452
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 452
ucuuagugua ugauuacugn n                                                21

<210> SEQ ID NO 453
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 453
caguaaucau acacuaagan n                          21

<210> SEQ ID NO 454
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 454
aucuuagugu augauuacug gcc                        23

<210> SEQ ID NO 455
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 455
cuuaguguau gauuacuggn n                          21

<210> SEQ ID NO 456
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 456
ccaguaauca uacacuaagn n                          21

<210> SEQ ID NO 457
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 457
ucuuagugua ugauuacugg ccu                        23

<210> SEQ ID NO 458
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 458
uuaguguaug auuacuggcn n                          21

<210> SEQ ID NO 459
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 459
gccaguaauc auacacuaan n                                              21

<210> SEQ ID NO 460
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 460
cuuaguguau gauuacuggc cuu                                            23

<210> SEQ ID NO 461
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 461
uaguguauga uuacuggccn n                                              21

<210> SEQ ID NO 462
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 462
ggccaguaau cauacacuan n                                              21

<210> SEQ ID NO 463
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 463
uuaguguaug auuacuggcc uuu                                            23

<210> SEQ ID NO 464
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 464
aguguaugau uacuggccun n                                              21

<210> SEQ ID NO 465
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 465
aggccaguaa ucauacacun n                                              21

<210> SEQ ID NO 466
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 466
uaguguauga uuacuggccu uuu                                            23

<210> SEQ ID NO 467
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 467
guguaugauu acuggccuun n                                              21

<210> SEQ ID NO 468
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 468
aaggccagua aucauacacn n                                              21

<210> SEQ ID NO 469
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 469
aguguaugau uacuggccuu uuu                                            23

<210> SEQ ID NO 470
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 470
uguaugauua cuggccuuun n                                              21

<210> SEQ ID NO 471
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 471
aaaggccagu aaucauacan n                                              21

<210> SEQ ID NO 472
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 472
guguaugauu acuggccuuu uuc                                            23

<210> SEQ ID NO 473
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 473
guaugauuac uggccuuuun n                                              21

<210> SEQ ID NO 474
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 474
aaaaggccag uaaucauacn n                                              21

<210> SEQ ID NO 475
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 475
uucauuuauc uauaauuuac cua                                              23

<210> SEQ ID NO 476
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 476
cauuuaucua uaauuuaccn n                                                21

<210> SEQ ID NO 477
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 477
gguaaauuau agauaaaugn n                                                21

<210> SEQ ID NO 478
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 478
ucauuuaucu auaauuuacc uaa                                              23

<210> SEQ ID NO 479
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 479
auuuaucuau aauuuaccun n                                                21

<210> SEQ ID NO 480
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 480
agguaaauua uagauaaaun n                                                21
```

-continued

<210> SEQ ID NO 481
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 481
cauuuaucua uaauuuaccu aag                                              23

<210> SEQ ID NO 482
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 482
uuuaucuaua auuuaccuan n                                                21

<210> SEQ ID NO 483
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 483
uagguaaauu auagauaaan n                                                21

<210> SEQ ID NO 484
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 484
auuuaucuau aauuuaccua aga                                              23

<210> SEQ ID NO 485
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 485
uuaucuauaa uuuaccuaan n                                                21

<210> SEQ ID NO 486
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 486
uuagguaaau uauagauaan n                                              21

<210> SEQ ID NO 487
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 487
uuuaucuaua auuuaccuaa gau                                            23

<210> SEQ ID NO 488
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 488
uaucuauaau uuaccuaagn n                                              21

<210> SEQ ID NO 489
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 489
cuuagguaaa uuauagauan n                                              21

<210> SEQ ID NO 490
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 490
uuaucuauaa uuuaccuaag auu                                            23

<210> SEQ ID NO 491
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 491
aucuauaauu uaccuaagan n                                              21
```

<210> SEQ ID NO 492
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 492
ucuuagguaa auuauagaun n                                              21

<210> SEQ ID NO 493
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 493
uaucuauaau uuaccuaaga uua                                            23

<210> SEQ ID NO 494
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 494
ucuauaauuu accuaagaun n                                              21

<210> SEQ ID NO 495
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 495
aucuuaggua aauuauagan n                                              21

<210> SEQ ID NO 496
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 496
aucuauaauu uaccuaagau uac                                            23

<210> SEQ ID NO 497
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 497
cuauaauuua ccuaagauun n                                                  21

<210> SEQ ID NO 498
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 498
aaucuuaggu aaauuauagn n                                                  21

<210> SEQ ID NO 499
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 499
ucuauaauuu accuaagauu aca                                                23

<210> SEQ ID NO 500
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 500
uauaauuuac cuaagauuan n                                                  21

<210> SEQ ID NO 501
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 501
uaaucuuagg uaaauuauan n                                                  21

<210> SEQ ID NO 502
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 502
cuauaauuua ccuaagauua caa                                                23
```

```
<210> SEQ ID NO 503
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 503
auaauuuacc uaagauuacn n                                              21

<210> SEQ ID NO 504
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 504
guaaucuuag guaaauuaun n                                              21

<210> SEQ ID NO 505
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 505
uauaauuuac cuaagauuac aaa                                            23

<210> SEQ ID NO 506
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 506
uaauuuaccu aagauuacan n                                              21

<210> SEQ ID NO 507
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 507
uguaaucuua gguaaauuan n                                              21

<210> SEQ ID NO 508
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 508
auaauuuacc uaagauuaca aau                                              23

<210> SEQ ID NO 509
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 509
aauuuaccua agauuacaan n                                                21

<210> SEQ ID NO 510
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 510
uuguaaucuu agguaaauun n                                                21

<210> SEQ ID NO 511
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 511
uaauuuaccu aagauuacaa auc                                              23

<210> SEQ ID NO 512
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 512
auuuaccuaa gauuacaaan n                                                21

<210> SEQ ID NO 513
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

<400> SEQUENCE: 513
uuuguaaucu uagguaaaun n                                              21

<210> SEQ ID NO 514
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 514
aauuuaccua agauuacaaa uca                                            23

<210> SEQ ID NO 515
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 515
uuuaccuaag auuacaaaun n                                              21

<210> SEQ ID NO 516
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 516
auuuguaauc uugguaaan n                                               21

<210> SEQ ID NO 517
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 517
auuuaccuaa gauuacaaau cag                                            23

<210> SEQ ID NO 518
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 518
uuaccuaaga uuacaaaucn n                                              21

<210> SEQ ID NO 519
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 519
gauuuguaau cuuagguaan n                                              21

<210> SEQ ID NO 520
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 520
uuuaccuaag auuacaaauc aga                                            23

<210> SEQ ID NO 521
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 521
uaccuaagau uacaaaucan n                                              21

<210> SEQ ID NO 522
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 522
ugauuuguaa ucuuagguan n                                              21

<210> SEQ ID NO 523
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 523
agaagucauc uugcuaccag uau                                            23

<210> SEQ ID NO 524
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 524
aagucaucuu gcuaccagun n                                              21

<210> SEQ ID NO 525
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 525
acugguagca agaugacuun n                                              21

<210> SEQ ID NO 526
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 526
gaagucaucu ugcuaccagu auu                                            23

<210> SEQ ID NO 527
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 527
agucaucuug cuaccaguan n                                              21

<210> SEQ ID NO 528
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 528
uacugguagc aagaugacun n                                              21

<210> SEQ ID NO 529
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 529
aagucaucuu gcuaccagua uuu                                            23

<210> SEQ ID NO 530
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 530
gucaucuugc uaccaguaun n                                              21

<210> SEQ ID NO 531
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 531
auacugguag caagaugacn n                                              21

<210> SEQ ID NO 532
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 532
agucaucuug cuaccaguau uua                                            23

<210> SEQ ID NO 533
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 533
ucaucuugcu accaguauun n                                              21

<210> SEQ ID NO 534
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 534 aauacggua gcaagaugan n                                               21

<210> SEQ ID NO 535
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 535
gucaucuugc uaccaguauu uag                                          23

<210> SEQ ID NO 536
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 536
caucuugcua ccaguauuun n                                            21

<210> SEQ ID NO 537
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 537
aaauacuggu agcaagaugn n                                            21

<210> SEQ ID NO 538
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 538
ucaucuugcu accaguauuu aga                                          23

<210> SEQ ID NO 539
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 539
aucuugcuac caguauuuan n                                            21

<210> SEQ ID NO 540
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 540
uaaauacugg uagcaagaun n                                            21
```

<210> SEQ ID NO 541
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 541
caucuugcua ccaguauuua gaa                                                23

<210> SEQ ID NO 542
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 542
ucuugcuacc aguauuuagn n                                                  21

<210> SEQ ID NO 543
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 543
cuaaauacug guagcaagan n                                                  21

<210> SEQ ID NO 544
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 544
aucuugcuac caguauuuag aag                                                23

<210> SEQ ID NO 545
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 545
cuugcuacca guauuuagan n                                                  21

<210> SEQ ID NO 546
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 546
ucuaaauacu gguagcaagn n                                              21

<210> SEQ ID NO 547
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 547
ucuugcuacc aguauuuaga agc                                            23

<210> SEQ ID NO 548
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 548
uugcuaccag uauuuagaan n                                              21

<210> SEQ ID NO 549
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 549
uucuaaauac ugguagcaan n                                              21

<210> SEQ ID NO 550
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 550
cuugcuacca guauuuagaa gcc                                            23

<210> SEQ ID NO 551
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 551
ugcuaccagu auuuagaagn n                                              21
```

```
<210> SEQ ID NO 552
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 552
cuucuaaaua cugguagcan n                                              21

<210> SEQ ID NO 553
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 553
uugcuaccag uauuuagaag cca                                            23

<210> SEQ ID NO 554
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 554
gcuaccagua uuuagaagcn n                                              21

<210> SEQ ID NO 555
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 555
gcuucuaaau acugguagcn n                                              21

<210> SEQ ID NO 556
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 556
ugcuaccagu auuuagaagc caa                                            23

<210> SEQ ID NO 557
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 557
cuaccaguau uuagaagccn n                                          21

<210> SEQ ID NO 558
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 558
ggcuucuaaa uacugguagn n                                          21

<210> SEQ ID NO 559
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 559
gcuaccagua uuuagaagcc aac                                        23

<210> SEQ ID NO 560
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 560
uaccaguauu uagaagccan n                                          21

<210> SEQ ID NO 561
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 561
uggcuucuaa auacuggan n                                           21

<210> SEQ ID NO 562
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 562
cuaccaguau uuagaagcca acu                                        23
```

```
<210> SEQ ID NO 563
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 563
accaguauuu agaagccaan n                                              21

<210> SEQ ID NO 564
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 564
uuggcuucua aauacuggun n                                              21

<210> SEQ ID NO 565
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 565
uaccaguauu uagaagccaa cua                                            23

<210> SEQ ID NO 566
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 566
ccaguauuua gaagccaacn n                                              21

<210> SEQ ID NO 567
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 567
guuggcuucu aaauacuggn n                                              21

<210> SEQ ID NO 568
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 568
cuugcuucuu ucuagaaaga gaa                                           23

<210> SEQ ID NO 569
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 569
ugcuucuuuc uagaaagagn n                                             21

<210> SEQ ID NO 570
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 570
cucuuucuag aaagaagcan n                                             21

<210> SEQ ID NO 571
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 571
uugcuucuuu cuagaaagag aaa                                           23

<210> SEQ ID NO 572
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 572
gcuucuuucu agaaagagan n                                             21

<210> SEQ ID NO 573
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 573
ucucuuucua gaaagaagcn n                                              21

<210> SEQ ID NO 574
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 574
ugcuucuuuc uagaaagaga aac                                            23

<210> SEQ ID NO 575
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 575
cuucuuucua gaaagagaan n                                              21

<210> SEQ ID NO 576
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 576
uucucuuucu agaaagaagn n                                              21

<210> SEQ ID NO 577
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 577
gcuucuuucu agaaagagaa aca                                            23

<210> SEQ ID NO 578
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 578
uucuuucuag aaagagaaan n                                              21

<210> SEQ ID NO 579
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 579
uuucucuuuc uagaaagaan n                                           21

<210> SEQ ID NO 580
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 580
cuucuuucua gaaagagaaa cag                                         23

<210> SEQ ID NO 581
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 581
ucuuucuaga aagagaaacn n                                           21

<210> SEQ ID NO 582
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 582
guuucucuuu cuagaaagan n                                           21

<210> SEQ ID NO 583
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 583
uucuuucuag aaagagaaac agu                                         23

<210> SEQ ID NO 584
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 584
cuuucuagaa agagaaacan n                                          21

<210> SEQ ID NO 585
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 585
uguuucucuu ucuagaaagn n                                          21

<210> SEQ ID NO 586
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 586
ucuuucuaga aagagaaaca guu                                        23

<210> SEQ ID NO 587
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 587
uuucuagaaa gagaaacagn n                                          21

<210> SEQ ID NO 588
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 588
cuguuucucu uucuagaaan n                                          21

<210> SEQ ID NO 589
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 589
cuuucuagaa agagaaacag uug                                        23

<210> SEQ ID NO 590
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 590
uucuagaaag agaaacagun n                                          21

<210> SEQ ID NO 591
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 591
acuguuucuc uuucuagaan n                                          21

<210> SEQ ID NO 592
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 592
uuucuagaaa gagaaacagu ugg                                        23

<210> SEQ ID NO 593
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 593
ucuagaaaga gaaacaguun n                                          21

<210> SEQ ID NO 594
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 594
aacuguuucu cuuucuagan n                                          21

<210> SEQ ID NO 595
<211> LENGTH: 23
<212> TYPE: RNA
<213> ORGANISM: Artificial Sequence
<220> FEATURE:
<223> OTHER INFORMATION: Exemplary iRNA agents
```

<400> SEQUENCE: 595
uucuagaaag agaaacaguu ggu                                          23

<210> SEQ ID NO 596
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 596
cuagaaagag aaacaguugn n                                            21

<210> SEQ ID NO 597
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 597
caacuguuuc ucuuucuagn n                                            21

<210> SEQ ID NO 598
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 598
ucuagaaaga gaaacaguug gua                                          23

<210> SEQ ID NO 599
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 599
uagaaagaga aacaguuggn n                                            21

<210> SEQ ID NO 600
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 600
ccaacuguuu cucuuucuan n                                            21

<210> SEQ ID NO 601
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 601
cuagaaagag aaacaguugg uaa                                             23

<210> SEQ ID NO 602
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 602
agaaagagaa acaguuggun n                                               21

<210> SEQ ID NO 603
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 603
accaacuguu ucucuuucun n                                               21

<210> SEQ ID NO 604
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 604
uagaaagaga aacaguuggu aac                                             23

<210> SEQ ID NO 605
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 605
gaaagagaaa caguugguan n                                               21

<210> SEQ ID NO 606
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 606
uaccaacugu uucucuuucn n                                                    21

<210> SEQ ID NO 607
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 607
agaaagagaa acaguuggua acu                                                  23

<210> SEQ ID NO 608
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 608
aaagagaaac aguugguaan n                                                    21

<210> SEQ ID NO 609
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 609
uuaccaacug uuucucuuun n                                                    21

<210> SEQ ID NO 610
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 610
gaaagagaaa caguugguaa cuu                                                  23

<210> SEQ ID NO 611
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 611
aagagaaaca guugguaacn n                                                    21
```

```
<210> SEQ ID NO 612
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 612
guuaccaacu guuucucuun n                                        21

<210> SEQ ID NO 613
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 613
aaagagaaac aguugguaac uuu                                      23

<210> SEQ ID NO 614
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 614
agagaaacag uugguaacun n                                        21

<210> SEQ ID NO 615
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 615
aguuaccaac uguuucucun n                                        21

<210> SEQ ID NO 616
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 616
aagagaaaca guugguaacu uuu                                      23

<210> SEQ ID NO 617
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 617
gagaaacagu ugguaacuun n                                              21

<210> SEQ ID NO 618
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 618
aaguuaccaa cuguuucucn n                                              21

<210> SEQ ID NO 619
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 619
agagaaacag uugguaacuu uug                                            23

<210> SEQ ID NO 620
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 620
agaaacaguu gguaacuuun n                                              21

<210> SEQ ID NO 621
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 621
aaaguuacca acuguuucn n                                               21

<210> SEQ ID NO 622
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 622
gagaaacagu ugguaacuuu ugu                                            23
```

```
<210> SEQ ID NO 623
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 623
gaaacaguug guaacuuuun n                                              21

<210> SEQ ID NO 624
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 624
aaaaguuacc aacuguuucn n                                              21

<210> SEQ ID NO 625
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 625
agaaacaguu gguaacuuuu gug                                            23

<210> SEQ ID NO 626
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 626
aaacaguugg uaacuuuugn n                                              21

<210> SEQ ID NO 627
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 627
caaaaguuac caacuguuun n                                              21

<210> SEQ ID NO 628
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 628
gaaacaguug guaacuuuug uga                                              23

<210> SEQ ID NO 629
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 629
aacaguuggu aacuuuugun n                                                21

<210> SEQ ID NO 630
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 630
acaaaaguua ccaacuguun n                                                21

<210> SEQ ID NO 631
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 631
aaacaguugg uaacuuuugu gaa                                              23

<210> SEQ ID NO 632
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 632
acaguuggua acuuuugugn n                                                21

<210> SEQ ID NO 633
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 633
cacaaaaguu accaacugun n                                               21

<210> SEQ ID NO 634
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 634
aacaguuggu aacuuugug aau                                              23

<210> SEQ ID NO 635
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 635
caguugguaa cuuuugugan n                                               21

<210> SEQ ID NO 636
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 636
ucacaaaagu uaccaacugn n                                               21

<210> SEQ ID NO 637
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 637
acaguuggua acuuuuguga auu                                             23

<210> SEQ ID NO 638
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 638
aguugguaac uuuugugaan n                                               21

<210> SEQ ID NO 639
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 639
uucacaaaag uuaccaacun n                                              21

<210> SEQ ID NO 640
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 640
caguugguaa cuuuugugaa uua                                            23

<210> SEQ ID NO 641
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 641
guugguaacu uuugugaaun n                                              21

<210> SEQ ID NO 642
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 642
auucacaaaa guuaccaacn n                                              21

<210> SEQ ID NO 643
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 643
aguugguaac uuuugugaau uag                                            23

<210> SEQ ID NO 644
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 644
uugguaacuu uugugaauun n                    21

<210> SEQ ID NO 645
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 645
aauucacaaa aguuaccaan n                    21

<210> SEQ ID NO 646
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 646
guugguaacu uuugugaauu agg                  23

<210> SEQ ID NO 647
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 647
ugguaacuuu ugugaauuan n                    21

<210> SEQ ID NO 648
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 648
uaauucacaa aaguuaccan n                    21

<210> SEQ ID NO 649
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 649
uugguaacuu uugugaauua ggc                  23

<210> SEQ ID NO 650
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 650
gguaacuuuu gugaauuagn n                                              21

<210> SEQ ID NO 651
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 651
cuaauucaca aaaguuaccn n                                              21

<210> SEQ ID NO 652
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 652
ugguaacuuu ugugaauuag gcu                                            23

<210> SEQ ID NO 653
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 653
guaacuuuug ugaauuaggn n                                              21

<210> SEQ ID NO 654
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 654
ccuaauucac aaaaguuacn n                                              21

<210> SEQ ID NO 655
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 655
gguaacuuuu gugaauuagg cug                                              23

<210> SEQ ID NO 656
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 656
uaacuuuugu gaauuaggcn n                                                21

<210> SEQ ID NO 657
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 657
gccuaauuca caaaaguuan n                                                21

<210> SEQ ID NO 658
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 658
guaacuuuug ugaauuaggc ugu                                              23

<210> SEQ ID NO 659
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 659
aacuuuugug aauuaggcun n                                                21

<210> SEQ ID NO 660
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 660
agccuaauuc acaaaaguun n                                                21
```

<210> SEQ ID NO 661
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 661 uaacuuugu gaauuaggcu gua                                        23

<210> SEQ ID NO 662
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 662
acuuuuguga auuaggcugn n                                         21

<210> SEQ ID NO 663
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 663
cagccuaauu cacaaaagun n                                         21

<210> SEQ ID NO 664
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 664
aacuuuugug aauuaggcug uaa                                       23

<210> SEQ ID NO 665
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 665
cuuuugugaa uuaggcugun n                                         21

<210> SEQ ID NO 666
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 666
acagccuaau ucacaaaagn n                                              21

<210> SEQ ID NO 667
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 667
acuuuuguga auuaggcugu aac                                            23

<210> SEQ ID NO 668
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 668
uuuugugaau uaggcuguan n                                              21

<210> SEQ ID NO 669
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 669
uacagccuaa uucacaaaan n                                              21

<210> SEQ ID NO 670
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 670
cuuuugugaa uuaggcugua acu                                            23

<210> SEQ ID NO 671
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 671
uuugugaauu aggcuguaan n                                              21
```

```
<210> SEQ ID NO 672
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 672
uuacagccua auucacaaan n                                              21

<210> SEQ ID NO 673
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 673
uuuugugaau uaggcuguaa cua                                            23

<210> SEQ ID NO 674
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 674
uugugaauua ggcuguaacn n                                              21

<210> SEQ ID NO 675
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 675
guuacagccu aauucacaan n                                              21

<210> SEQ ID NO 676
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 676
uuugugaauu aggcuguaac uac                                            23

<210> SEQ ID NO 677
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 677
ugugaauuag gcuguaacun n                                                   21

<210> SEQ ID NO 678
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 678
aguuacagcc uaauucacan n                                                   21

<210> SEQ ID NO 679
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 679
uugugaauua ggcuguaacu acu                                                 23

<210> SEQ ID NO 680
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 680
gugaauuagg cuguaacuan n                                                   21

<210> SEQ ID NO 681
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 681
uaguuacagc cuaauucacn n                                                   21

<210> SEQ ID NO 682
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 682
ugugaauuag gcuguaacua cuu                                                 23
```

-continued

<210> SEQ ID NO 683
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 683
ugaauuaggc uguaacuacn n                                            21

<210> SEQ ID NO 684
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 684
guaguuacag ccuaauucan n                                            21

<210> SEQ ID NO 685
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 685
gugaauuagg cuguaacuac uuu                                          23

<210> SEQ ID NO 686
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 686
gaauuaggcu guaacuacun n                                            21

<210> SEQ ID NO 687
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 687
aguaguuaca gccuaauucn n                                            21

<210> SEQ ID NO 688
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 688
ugaauuaggc uguaacuacu uua                                              23

<210> SEQ ID NO 689
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 689
aauuaggcug uaacuacuun n                                                21

<210> SEQ ID NO 690
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 690
aaguaguuac agccuaauun n                                                21

<210> SEQ ID NO 691
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 691
gaauuaggcu guaacuacuu uau                                              23

<210> SEQ ID NO 692
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 692
auuaggcugu aacuacuuun n                                                21

<210> SEQ ID NO 693
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 693
aaaguaguua cagccuaaun n                                      21

<210> SEQ ID NO 694
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 694
aauuaggcug uaacuacuuu aua                                    23

<210> SEQ ID NO 695
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 695
uuaggcugua acuacuuuan n                                      21

<210> SEQ ID NO 696
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 696
uaaaguaguu acagccuaan n                                      21

<210> SEQ ID NO 697
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 697
auuaggcugu aacuacuuua uaa                                    23

<210> SEQ ID NO 698
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 698
uaggcuguaa cuacuuuaun n                                      21

<210> SEQ ID NO 699
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 699
auaaaguagu uacagccuan n                                         21

<210> SEQ ID NO 700
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 700
uuaggcugua acuacuuuau aac                                       23

<210> SEQ ID NO 701
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 701
aggcuguaac uacuuuauan n                                         21

<210> SEQ ID NO 702
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 702
uauaaaguag uuacagccun n                                         21

<210> SEQ ID NO 703
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 703
uaggcuguaa cuacuuuaua acu                                       23

<210> SEQ ID NO 704
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 704
ggcuguaacu acuuuauaan n                                      21

<210> SEQ ID NO 705
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 705
uuauaaagua guuacagccn n                                      21

<210> SEQ ID NO 706
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 706
aggcuguaac uacuuuauaa cua                                    23

<210> SEQ ID NO 707
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 707
gcuguaacua cuuuauaacn n                                      21

<210> SEQ ID NO 708
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 708
guuauaaagu aguuacagcn n                                      21

<210> SEQ ID NO 709
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 709
ggcuguaacu acuuuauaac uaa                                    23

<210> SEQ ID NO 710
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 710 cguaacuac uuuauaacun n                                          21

<210> SEQ ID NO 711
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 711
aguuauaaag uaguuacagn n                                         21

<210> SEQ ID NO 712
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 712
gcuguaacua cuuuauaacu aac                                       23

<210> SEQ ID NO 713
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 713
uguaacuacu uuauaacuan n                                         21

<210> SEQ ID NO 714
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 714
uaguuauaaa guaguuacan n                                         21

<210> SEQ ID NO 715
<211> LENGTH: 23
<212> TYPE: RNA
<213> ORGANISM: Artificial Sequence
<220> FEATURE:
<223> OTHER INFORMATION: Exemplary iRNA agents
```

-continued

```
<400> SEQUENCE: 715
cuguaacuac uuuauaacua aca                                              23

<210> SEQ ID NO 716
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 716
guaacuacuu uauaacuaan n                                                21

<210> SEQ ID NO 717
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 717
uuaguuauaa aguaguuacn n                                                21

<210> SEQ ID NO 718
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 718
uguaacuacu uuauaacuaa cau                                              23

<210> SEQ ID NO 719
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 719
uaacuacuuu auaacuaacn n                                                21

<210> SEQ ID NO 720
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 720
guuaguuaua aaguaguuan n                                                21
```

<210> SEQ ID NO 721
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 721
guaacuacuu uauaacuaac aug                                              23

<210> SEQ ID NO 722
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 722
aacuacuuua uaacuaacan n                                                21

<210> SEQ ID NO 723
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 723
uguuaguuau aaaguaguun n                                                21

<210> SEQ ID NO 724
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 724
uaacuacuuu auaacuaaca ugu                                              23

<210> SEQ ID NO 725
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 725
acuacuuuau aacuaacaun n                                                21

<210> SEQ ID NO 726
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 726
auguuaguua uaaaguagun n                                          21

<210> SEQ ID NO 727
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 727
aacuacuuua uaacuaacau guc                                        23

<210> SEQ ID NO 728
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 728
cuacuuuaua acuaacaugn n                                          21

<210> SEQ ID NO 729
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 729
cauguuaguu auaaaguagn n                                          21

<210> SEQ ID NO 730
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 730
acuacuuuau aacuaacaug ucc                                        23

<210> SEQ ID NO 731
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 731
uacuuuauaa cuaacaugn n                                           21
```

<210> SEQ ID NO 732
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 732
acauguuagu uauaaaguan n                                              21

<210> SEQ ID NO 733
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 733
cuacuuuaua acuaacaugu ccu                                            23

<210> SEQ ID NO 734
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 734
acuuuauaac uaacaugucn n                                              21

<210> SEQ ID NO 735
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 735
gacauguuag uuauaaagun n                                              21

<210> SEQ ID NO 736
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 736
uacuuuauaa cuaacauguc cug                                            23

<210> SEQ ID NO 737
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 737
cuuuauaacu aacauguccn n                                                 21

<210> SEQ ID NO 738
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 738
ggacauguua guuauaaagn n                                                 21

<210> SEQ ID NO 739
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 739
acuuuauaac uaacaugucc ugc                                               23

<210> SEQ ID NO 740
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 740
uuuauaacua acauguccun n                                                 21

<210> SEQ ID NO 741
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 741
aggacauguu aguuauaaan n                                                 21

<210> SEQ ID NO 742
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 742
cuuuauaacu aacauguccu gcc                                               23
```

<210> SEQ ID NO 743
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 743
uuauaacuaa cauguccugn n                                              21

<210> SEQ ID NO 744
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 744
caggacaugu uaguuauaan n                                              21

<210> SEQ ID NO 745
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 745
uuuauaacua acauguccug ccu                                            23

<210> SEQ ID NO 746
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 746
uauaacuaac auguccugcn n                                              21

<210> SEQ ID NO 747
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 747
gcaggacaug uuaguuauan n                                              21

<210> SEQ ID NO 748
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 748
uuauaacuaa cauguccugc cua                                              23

<210> SEQ ID NO 749
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 749
auaacuaaca uguccugccn n                                                21

<210> SEQ ID NO 750
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 750
ggcaggacau guuaguuaun n                                                21

<210> SEQ ID NO 751
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 751
uauaacuaac auguccugcc uau                                              23

<210> SEQ ID NO 752
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 752
uaacuaacau guccugccun n                                                21

<210> SEQ ID NO 753
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 753
aggcaggaca uguuaguuan n					21

<210> SEQ ID NO 754
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 754
auaacuaaca uguccugccu auu					23

<210> SEQ ID NO 755
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 755
aacuaacaug uccugccuan n					21

<210> SEQ ID NO 756
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 756
uaggcaggac auguuaguun n					21

<210> SEQ ID NO 757
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 757
uggcagaguu acaguucugu ggu					23

<210> SEQ ID NO 758
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 758
gcagaguuac aguucugugn n					21

<210> SEQ ID NO 759
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 759
cacagaacug uaacucugcn n                                              21

<210> SEQ ID NO 760
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 760
ggcagaguua caguucugug guu                                            23

<210> SEQ ID NO 761
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 761
cagaguuaca guucuguggn n                                              21

<210> SEQ ID NO 762
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 762
ccacagaacu guaacucugn n                                              21

<210> SEQ ID NO 763
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 763
gcagaguuac aguucugugg uuu                                            23

<210> SEQ ID NO 764
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

<400> SEQUENCE: 764
agaguuacag uucuguggun n					21

<210> SEQ ID NO 765
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 765
accacagaac uguaacucun n					21

<210> SEQ ID NO 766
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 766
uuucauguua guuaccuuau agu				23

<210> SEQ ID NO 767
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 767
ucauguuagu uaccuuauan n					21

<210> SEQ ID NO 768
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 768
uauaagguaa cuaacaugan n					21

<210> SEQ ID NO 769
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 769
uucauguuag uuaccuuaua guu				23

<210> SEQ ID NO 770
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 770
cauguuaguu accuuauagn n                                              21

<210> SEQ ID NO 771
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 771
cuauaaggua acuaacaugn n                                              21

<210> SEQ ID NO 772
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 772
ucauguuagu uaccuuauag uua                                            23

<210> SEQ ID NO 773
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 773
auguuaguua ccuuauagun n                                              21

<210> SEQ ID NO 774
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 774
acuauaaggu aacuaacaun n                                              21

<210> SEQ ID NO 775
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 775
cauguuaguu accuuauagu uac                                              23

<210> SEQ ID NO 776
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 776
uguuaguuac cuuauaguun n                                                21

<210> SEQ ID NO 777
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 777
aacuauaagg uaacuaacan n                                                21

<210> SEQ ID NO 778
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 778
auguuaguua ccuuauaguu acu                                              23

<210> SEQ ID NO 779
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 779
guuaguuacc uuauaguuan n                                                21

<210> SEQ ID NO 780
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 780
uaacuauaag guaacuaacn n                                                21
```

<210> SEQ ID NO 781
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 781
uguuaguuac cuuauaguua cug                                              23

<210> SEQ ID NO 782
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 782
uuaguuaccu uauaguuacn n                                                21

<210> SEQ ID NO 783
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 783
guaacuauaa gguaacuaan n                                                21

<210> SEQ ID NO 784
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 784
guuaguuacc uuauaguuac ugu                                              23

<210> SEQ ID NO 785
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 785
uaguuaccuu auaguuacun n                                                21

<210> SEQ ID NO 786
<211> LENGTH: 21
<212> TYPE: DNA
<213> ORGANISM: Artificial Sequence
<220> FEATURE:
<223> OTHER INFORMATION: Exemplary iRNA agents

```
-continued

<220> FEATURE:
<221> NAME/KEY: misc_feature
<222> LOCATION: 20, 21
<223> OTHER INFORMATION: n = 2'-deoxy-thymidine

<400> SEQUENCE: 786
aguaacuaua agguaacuan n                                              21

<210> SEQ ID NO 787
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 787
uuaguuaccu uauaguuacu gug                                            23

<210> SEQ ID NO 788
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 788
aguuaccuua uaguuacugn n                                              21

<210> SEQ ID NO 789
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 789
caguaacuau aagguaacun n                                              21

<210> SEQ ID NO 790
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 790
uaguuaccuu auaguuacug ugu                                            23

<210> SEQ ID NO 791
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 791
guuaccuuau aguuacugun n                                              21
```

<210> SEQ ID NO 792
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 792
acaguaacua uaagguaacn n                                              21

<210> SEQ ID NO 793
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 793
aguuaccuua uaguuacugu gua                                            23

<210> SEQ ID NO 794
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 794
uuaccuuaua guuacugugn n                                              21

<210> SEQ ID NO 795
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 795
cacaguaacu auaagguaan n                                              21

<210> SEQ ID NO 796
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 796
guuaccuuau aguuacugug uaa                                            23

<210> SEQ ID NO 797
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 797
uaccuuauag uuacugugun n                                            21

<210> SEQ ID NO 798
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 798
acacaguaac uauaagguan n                                            21

<210> SEQ ID NO 799
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 799
uuaccuuaua guuacugugu aau                                          23

<210> SEQ ID NO 800
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 800
accuuauagu uacuguguan n                                            21

<210> SEQ ID NO 801
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 801
uacacaguaa cuauaaggun n                                            21

<210> SEQ ID NO 802
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 802
uaccuuauag uuacugugua auu                                          23
```

<210> SEQ ID NO 803
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 803
ccuuauaguu acuguguaan n                                        21

<210> SEQ ID NO 804
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 804
uuacacagua acuauaaggn n                                        21

<210> SEQ ID NO 805
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 805
accuuauagu uacuguguaa uua                                      23

<210> SEQ ID NO 806
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 806
cuuauaguua cuguguaaun n                                        21

<210> SEQ ID NO 807
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 807
auuacacagu aacuauaagn n                                        21

<210> SEQ ID NO 808
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 808
ccuuauaguu acuguguaau uag                                              23

<210> SEQ ID NO 809
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 809
uuauaguuac uguguaauun n                                                21

<210> SEQ ID NO 810
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 810
aauuacacag uaacuauaan n                                                21

<210> SEQ ID NO 811
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 811
cuuauaguua cuguguaauu agu                                              23

<210> SEQ ID NO 812
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 812
uauaguuacu guguaauuan n                                                21

<210> SEQ ID NO 813
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 813
uaauuacaca guaacuauan n                                              21

<210> SEQ ID NO 814
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 814
uuauaguuac uguguaauua gug                                            23

<210> SEQ ID NO 815
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 815
auaguuacug uguaauuagn n                                              21

<210> SEQ ID NO 816
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 816
cuaauuacac aguaacuaun n                                              21

<210> SEQ ID NO 817
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 817
uauaguuacu guguaauuag ugc                                            23

<210> SEQ ID NO 818
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 818
uaguuacugu guaauuagun n                                              21

<210> SEQ ID NO 819
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 819
acuaauuaca caguaacuan n                                              21

<210> SEQ ID NO 820
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 820
auaguuacug uguaauuagu gcc                                            23

<210> SEQ ID NO 821
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 821
aguuacugug uaauuagugn n                                              21

<210> SEQ ID NO 822
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 822
cacuaauuac acaguaacun n                                              21

<210> SEQ ID NO 823
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 823
uaguuacugu guaauuagug cca                                            23

<210> SEQ ID NO 824
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

```
<400> SEQUENCE: 824
guuacugugu aauuagugcn n                                      21

<210> SEQ ID NO 825
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 825
gcacuaauua cacaguaacn n                                      21

<210> SEQ ID NO 826
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 826
aguuacugug uaauuagugc cac                                    23

<210> SEQ ID NO 827
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 827
uuacugugua auuagugccn n                                      21

<210> SEQ ID NO 828
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 828
ggcacuaauu acacaguaan n                                      21

<210> SEQ ID NO 829
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 829
guuacugugu aauuagugcc acu                                    23

<210> SEQ ID NO 830
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 830
uacuguguaa uuagugccan n                                              21

<210> SEQ ID NO 831
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 831
uggcacuaau uacacaguan n                                              21

<210> SEQ ID NO 832
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 832
uuacugugua auuagugcca cuu                                            23

<210> SEQ ID NO 833
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 833
acuguguaau uagugccacn n                                              21

<210> SEQ ID NO 834
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 834
guggcacuaa uuacacagun n                                              21

<210> SEQ ID NO 835
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 835
uacuguguaa uuagugccac uua                                              23

<210> SEQ ID NO 836
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 836
cuguguaauu agugccacun n                                                21

<210> SEQ ID NO 837
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 837
aguggcacua auuacacagn n                                                21

<210> SEQ ID NO 838
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 838
acuguguaau uagugccacu uaa                                              23

<210> SEQ ID NO 839
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 839
uguguaauua gugccacuun n                                                21

<210> SEQ ID NO 840
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 840
aaguggcacu aauuacacan n                                                21
```

<210> SEQ ID NO 841
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 841
cuguguaauu agugccacuu aau                                             23

<210> SEQ ID NO 842
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 842
guguaauuag ugccacuuan n                                               21

<210> SEQ ID NO 843
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 843
uaaguggcac uaauuacacn n                                               21

<210> SEQ ID NO 844
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 844
uguguaauua gugccacuua aug                                             23

<210> SEQ ID NO 845
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 845
uguaauuagu gccacuuaan n                                               21

<210> SEQ ID NO 846
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 846
uuaaguggca cuaauuacan n                                              21

<210> SEQ ID NO 847
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 847
guguaauuag ugccacuuaa ugu                                            23

<210> SEQ ID NO 848
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 848
guaauuagug ccacuuaaun n                                              21

<210> SEQ ID NO 849
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 849
auuaaguggc acuaauuacn n                                              21

<210> SEQ ID NO 850
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 850
uguaauuagu gccacuuaau gua                                            23

<210> SEQ ID NO 851
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 851
uaauuagugc cacuuaaugn n                                              21
```

```
<210> SEQ ID NO 852
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 852
cauuaagugg cacuaauuan n                                              21

<210> SEQ ID NO 853
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 853
guaauuagug ccacuuaaug uau                                            23

<210> SEQ ID NO 854
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 854
aauuagugcc acuuaaugun n                                              21

<210> SEQ ID NO 855
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 855
acauuaagug gcacuaauun n                                              21

<210> SEQ ID NO 856
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 856 uaauuaguluc cacuuaaugu aug                                           23

<210> SEQ ID NO 857
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 857
auuagugcca cuuaauguan n                                                    21

<210> SEQ ID NO 858
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 858
uacauuaagu ggcacuaaun n                                                    21

<210> SEQ ID NO 859
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 859
aauuagugcc acuuaaugua ugu                                                  23

<210> SEQ ID NO 860
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 860
uuagugccac uuaauguaun n                                                    21

<210> SEQ ID NO 861
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 861
auacauuaag uggcacuaan n                                                    21

<210> SEQ ID NO 862
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 862
auuagugcca cuuaauguau guu                                                  23
```

<210> SEQ ID NO 863
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 863
uagugccacu uaauguaugn n                                        21

<210> SEQ ID NO 864
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 864
cauacauuaa guggcacuan n                                        21

<210> SEQ ID NO 865
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 865
uuagugccac uuaauguaug uua                                      23

<210> SEQ ID NO 866
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 866
agugccacuu aauguaugun n                                        21

<210> SEQ ID NO 867
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 867
acauacauua aguggcacun n                                        21

<210> SEQ ID NO 868
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 868
uagugccacu uaauguaugu uac                                              23

<210> SEQ ID NO 869
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 869
gugccacuua auguauguun n                                                21

<210> SEQ ID NO 870
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 870
aacauacauu aaguggcacn n                                                21

<210> SEQ ID NO 871
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 871
agugccacuu aauguauguu acc                                              23

<210> SEQ ID NO 872
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 872
ugccacuuaa uguauguuan n                                                21

<210> SEQ ID NO 873
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 873
uaacauacau uaaguggcan n                                              21

<210> SEQ ID NO 874
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 874
gugccacuua auguauguua cca                                            23

<210> SEQ ID NO 875
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 875
gccacuuaau guauguuacn n                                              21

<210> SEQ ID NO 876
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 876
guaacauaca uuaaguggcn n                                              21

<210> SEQ ID NO 877
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 877
ugccacuuaa uguauguuac caa                                            23

<210> SEQ ID NO 878
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 878
ccacuuaaug uauguuaccn n                                              21

<210> SEQ ID NO 879
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 879
gguaacauac auuaaguggn n                                              21

<210> SEQ ID NO 880
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 880
gccacuuaau guauguuacc aaa                                            23

<210> SEQ ID NO 881
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 881
cacuuaaugu auguuaccan n                                              21

<210> SEQ ID NO 882
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 882
ugguaacaua cauuaagugn n                                              21

<210> SEQ ID NO 883
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 883
ccacuuaaug uauguuacca aaa                                            23

<210> SEQ ID NO 884
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 884
acuuaaugua uguuaccaan n                                     21

<210> SEQ ID NO 885
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 885
uugguaacau acauuaagun n                                     21

<210> SEQ ID NO 886
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 886
cacuuaaugu auguuaccaa aaa                                   23

<210> SEQ ID NO 887
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 887
cuuaauguau guuaccaaan n                                     21

<210> SEQ ID NO 888
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 888
uuugguaaca uacauuaagn n                                     21

<210> SEQ ID NO 889
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 889
acuuaaugua uguuaccaaa aau                                   23

<210> SEQ ID NO 890
<211> LENGTH: 21
```

<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 890
uuaauguaug uuaccaaaan n                                   21

<210> SEQ ID NO 891
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 891
uuuugguaac auacauuaan n                                   21

<210> SEQ ID NO 892
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 892
cuuaauguau guuaccaaaa aua                                 23

<210> SEQ ID NO 893
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 893
uaauguaugu uaccaaaaan n                                   21

<210> SEQ ID NO 894
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 894
uuuuugguaa cauacauuan n                                   21

<210> SEQ ID NO 895
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 895
aauaaauaua ucuacccag acu    23

<210> SEQ ID NO 896
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 896
uaaauauauc uaccccagan n    21

<210> SEQ ID NO 897
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 897
ucugggguag auauauuuan n    21

<210> SEQ ID NO 898
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 898
auaaauauau cuaccccaga cua    23

<210> SEQ ID NO 899
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 899
aaauauaucu accccagacn n    21

<210> SEQ ID NO 900
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 900
gucuggggua gauauauuun n    21

<210> SEQ ID NO 901
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 901
uaaauauauc uaccccagac uag                                              23

<210> SEQ ID NO 902
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 902
aauauaucua ccccagacun n                                                21

<210> SEQ ID NO 903
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 903
agucuggggu agauauauun n                                                21

<210> SEQ ID NO 904
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 904
aaauauaucu accccagacu aga                                              23

<210> SEQ ID NO 905
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 905
auauaucuac cccagacuan n                                                21

<210> SEQ ID NO 906
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 906 uagucuggg uagauauaun n                                              21

<210> SEQ ID NO 907
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 907
aauauaucua ccccagacua gau                                           23

<210> SEQ ID NO 908
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 908
uauaucuacc ccagacuagn n                                             21

<210> SEQ ID NO 909
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 909
cuagucuggg guagauauan n                                             21

<210> SEQ ID NO 910
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 910
auauaucuac cccagacuag aug                                           23

<210> SEQ ID NO 911
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 911
auaucuaccc cagacuagan n                                             21
```

```
<210> SEQ ID NO 912
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 912
ucuagucugg gguagauaun n                                              21

<210> SEQ ID NO 913
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 913
uauaucuacc ccagacuaga ugu                                            23

<210> SEQ ID NO 914
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 914
uaucuacccc agacuagaun n                                              21

<210> SEQ ID NO 915
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 915
aucuagucug ggguagauan n                                              21

<210> SEQ ID NO 916
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 916
auaucuaccc cagacuagau gua                                            23

<210> SEQ ID NO 917
<211> LENGTH: 21
<212> TYPE: DNA
<213> ORGANISM: Artificial Sequence
<220> FEATURE:
<223> OTHER INFORMATION: Exemplary iRNA agents
```

```
<220> FEATURE:
<221> NAME/KEY: misc_feature
<222> LOCATION: 20, 21
<223> OTHER INFORMATION: n = 2'-deoxy-thymidine

<400> SEQUENCE: 917
aucuacccca gacuagaugn n                                              21

<210> SEQ ID NO 918
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 918
caucuagucu gggguagaun n                                              21

<210> SEQ ID NO 919
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 919
uaucuacccc agacuagaug uag                                            23

<210> SEQ ID NO 920
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 920
ucuaccccag acuagaugun n                                              21

<210> SEQ ID NO 921
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 921
acaucuaguc ugggguagan n                                              21

<210> SEQ ID NO 922
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 922
aucuacccca gacuagaugu agu                                            23
```

<210> SEQ ID NO 923
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 923
cuaccccaga cuagauguan n                                              21

<210> SEQ ID NO 924
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 924
uacaucuagu cugggguagn n                                              21

<210> SEQ ID NO 925
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 925
ucuaccccag acuagaugua gua                                            23

<210> SEQ ID NO 926
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 926
uaccccagac uagauguagn n                                              21

<210> SEQ ID NO 927
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 927
cuacaucuag ucuggggguan n                                             21

<210> SEQ ID NO 928
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 928
cuaccccaga cuagauguag uau                                              23

<210> SEQ ID NO 929
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 929
accccagacu agauguagun n                                                21

<210> SEQ ID NO 930
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 930
acuacaucua gucugggun n                                                 21

<210> SEQ ID NO 931
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 931
uaccccagac uagauguagu auu                                              23

<210> SEQ ID NO 932
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 932
ccccagacua gauguagan n                                                 21

<210> SEQ ID NO 933
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 933
uacuacaucu agucuggggn n                                              21

<210> SEQ ID NO 934
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 934
accccagacu agauguagua uuu                                            23

<210> SEQ ID NO 935
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 935
cccagacuag auguaguaun n                                              21

<210> SEQ ID NO 936
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 936
auacuacauc uagucugggn n                                              21

<210> SEQ ID NO 937
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 937
ccccagacua gauguaguau uuu                                            23

<210> SEQ ID NO 938
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 938
ccagacuaga uguaguauun n                                              21

<210> SEQ ID NO 939
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 939
aauacuacau cuagucuggn n                                              21

<210> SEQ ID NO 940
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 940
cccagacuag auguaguauu uuu                                            23

<210> SEQ ID NO 941
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 941
cagacuagau guaguauuun n                                              21

<210> SEQ ID NO 942
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 942
aaauacuaca ucuagucugn n                                              21

<210> SEQ ID NO 943
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 943
ccagacuaga uguaguauuu uuu                                            23

<210> SEQ ID NO 944
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
<400> SEQUENCE: 944
agacuagaug uaguauuuun n                                              21

<210> SEQ ID NO 945
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 945
aaaauacuac aucuagucun n                                              21

<210> SEQ ID NO 946
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 946
cagacuagau guaguauuuu uug                                            23

<210> SEQ ID NO 947
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 947
gacuagaugu aguauuuuun n                                              21

<210> SEQ ID NO 948
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 948
aaaaauacua caucuagucn n                                              21

<210> SEQ ID NO 949
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 949
agacuagaug uaguauuuuu ugu                                            23

<210> SEQ ID NO 950
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 950
acuagaugua guauuuuuun n                                              21

<210> SEQ ID NO 951
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 951
aaaaaauacu acaucuagun n                                              21

<210> SEQ ID NO 952
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 952
gacuagaugu aguauuuuuu gua                                            23

<210> SEQ ID NO 953
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 953
cuagauguag uauuuuugn n                                               21

<210> SEQ ID NO 954
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 954
caaaaaauac uacaucuagn n                                              21

<210> SEQ ID NO 955
<211> LENGTH: 23
<212> TYPE: RNA
<213> ORGANISM: Artificial Sequence
<220> FEATURE:
<223> OTHER INFORMATION: Exemplary iRNA agents
```

<400> SEQUENCE: 955
acuagaugua guauuuuuug uau                                           23

<210> SEQ ID NO 956
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 956
uagauguagu auuuuugun n                                              21

<210> SEQ ID NO 957
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 957
acaaaaaaua cuacaucuan n                                             21

<210> SEQ ID NO 958
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 958
cuagauguag uauuuuugu aua                                            23

<210> SEQ ID NO 959
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 959
agauguagua uuuuuguan n                                              21

<210> SEQ ID NO 960
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 960
uacaaaaaau acuacaucun n                                             21

<210> SEQ ID NO 961
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 961
uagauguagu auuuuugua uaa                                              23

<210> SEQ ID NO 962
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 962
gauguaguau uuuuguaun n                                                21

<210> SEQ ID NO 963
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 963
auacaaaaaa uacuacaucn n                                               21

<210> SEQ ID NO 964
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 964
agauguagua uuuuuguau aau                                              23

<210> SEQ ID NO 965
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 965
auguaguauu uuuguauan n                                                21

<210> SEQ ID NO 966
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 966
uauacaaaaa auacuacaun n                                              21

<210> SEQ ID NO 967
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 967
gauguaguau uuuuguaua auu                                             23

<210> SEQ ID NO 968
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 968
uguaguauuu uuuguauaan n                                              21

<210> SEQ ID NO 969
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 969
uuauacaaaa aauacuacan n                                              21

<210> SEQ ID NO 970
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 970
auguaguauu uuuuguauaa uug                                            23

<210> SEQ ID NO 971
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 971
guaguauuuu uuguauaaun n                                              21
```

<210> SEQ ID NO 972
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 972
auuauacaaa aaauacuacn n                                              21

<210> SEQ ID NO 973
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 973
uguaguauuu uuuguauaau ugg                                            23

<210> SEQ ID NO 974
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 974
uaguauuuuu uguauaauun n                                              21

<210> SEQ ID NO 975
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 975
aauuauacaa aaaauacuan n                                              21

<210> SEQ ID NO 976
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 976
guaguauuuu uuguauaauu gga                                            23

<210> SEQ ID NO 977
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 977
aguauuuuuu guauaauugn n                                              21

<210> SEQ ID NO 978
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 978
caauuauaca aaaaauacun n                                              21

<210> SEQ ID NO 979
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 979
uaguauuuuu uguauaauug gau                                            23

<210> SEQ ID NO 980
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 980
guauuuuuug uauaauuggn n                                              21

<210> SEQ ID NO 981
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 981
ccaauuauac aaaaaauacn n                                              21

<210> SEQ ID NO 982
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 982
aguauuuuuu guauaauugg auu                                            23
```

```
<210> SEQ ID NO 983
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 983 uauuuuugu auaauuggan n                                              21

<210> SEQ ID NO 984
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 984
uccaauuaua caaaaaauan n                                             21

<210> SEQ ID NO 985
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 985 guauuuuug uauaauugga uuu                                            23

<210> SEQ ID NO 986
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 986 auuuuugua uaauuggaun n                                              21

<210> SEQ ID NO 987
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 987
auccaauuau acaaaaaaun n                                             21

<210> SEQ ID NO 988
<211> LENGTH: 23
```

```
<212> TYPE: RNA
<213> ORGANISM: Artificial Sequence
<220> FEATURE:
<223> OTHER INFORMATION: Exemplary iRNA agents

<400> SEQUENCE: 988 uauuuuugu auaauuggau uuc                                              23

<210> SEQ ID NO 989
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 989 uuuuuguau aauuggauun n                                                21

<210> SEQ ID NO 990
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 990
aauccaauua uacaaaaaan n                                               21

<210> SEQ ID NO 991
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 991 auuuuugua uaauuggauu ucc                                              23

<210> SEQ ID NO 992
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 992
uuuuuguaua auggauuun n                                                21

<210> SEQ ID NO 993
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 993
aaauccaauu auacaaaaan n                                          21

<210> SEQ ID NO 994
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 994
uuuuuuguau aauuggauuu ccu                                        23

<210> SEQ ID NO 995
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 995
uuuuguauaa uuggauuucn n                                          21

<210> SEQ ID NO 996
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 996
gaaauccaau uauacaaaan n                                          21

<210> SEQ ID NO 997
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 997
uuuuuguaua auuggauuuc cua                                        23

<210> SEQ ID NO 998
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 998
uuuguauaau uggauuuccn n                                          21

<210> SEQ ID NO 999
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 999
ggaaauccaa uuauacaaan n                                              21

<210> SEQ ID NO 1000
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1000
uuuuguauaa uuggauuucc uaa                                            23

<210> SEQ ID NO 1001
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1001
uuguauaauu ggauuuccun n                                              21

<210> SEQ ID NO 1002
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1002
aggaaaucca auuauacaan n                                              21

<210> SEQ ID NO 1003
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1003
uuuguauaau uggauuuccu aau                                            23

<210> SEQ ID NO 1004
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

-continued

<400> SEQUENCE: 1004
uguauaauug gauuuccuan n                                              21

<210> SEQ ID NO 1005
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1005
uaggaaaucc aauuauacan n                                              21

<210> SEQ ID NO 1006
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1006
uuguauaauu ggauuccua aua                                             23

<210> SEQ ID NO 1007
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1007
guauaauugg auuccuaan n                                               21

<210> SEQ ID NO 1008
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1008
uuaggaaauc caauuauacn n                                              21

<210> SEQ ID NO 1009
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1009
uguauaauug gauuuccuaa uac                                            23

<210> SEQ ID NO 1010
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1010
uauaauugga uuccuaaun n                                              21

<210> SEQ ID NO 1011
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1011
auuaggaaau ccaauuauan n                                             21

<210> SEQ ID NO 1012
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1012
guauuuggaa auaaagucag aug                                           23

<210> SEQ ID NO 1013
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1013
auuuggaaau aaagucagan n                                             21

<210> SEQ ID NO 1014
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1014
ucugacuuua uuccaaaun n                                              21

<210> SEQ ID NO 1015
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 1015
uauuuggaaa uaaagucaga ugg                                              23

<210> SEQ ID NO 1016
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1016
uuuggaaaua aagucagaun n                                                21

<210> SEQ ID NO 1017
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1017
aucugacuuu auuccaaan n                                                 21

<210> SEQ ID NO 1018
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1018
auuuggaaau aaagucagau gga                                              23

<210> SEQ ID NO 1019
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1019
uuggaaauaa agucagaugn n                                                21

<210> SEQ ID NO 1020
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1020
caucugacuu uauuccaan n                                                 21
```

<210> SEQ ID NO 1021
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1021
uuuggaaaua aagucagaug gaa                                          23

<210> SEQ ID NO 1022
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1022
uggaaauaaa gucagauggn n                                            21

<210> SEQ ID NO 1023
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1023
ccaucugacu uuauuuccan n                                            21

<210> SEQ ID NO 1024
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1024
uuggaaauaa agucagaugg aaa                                          23

<210> SEQ ID NO 1025
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1025
ggaaauaaag ucagauggan n                                            21

<210> SEQ ID NO 1026
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 1026
uccaucugac uuuauuuccn n                                           21

<210> SEQ ID NO 1027
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1027
uggaaauaaa gucagaugga aaa                                         23

<210> SEQ ID NO 1028
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1028
gaaauaaagu cagauggaan n                                           21

<210> SEQ ID NO 1029
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1029
uuccaucuga cuuuauuucn n                                           21

<210> SEQ ID NO 1030
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1030
ucccucccag aggagccacc agu                                         23

<210> SEQ ID NO 1031
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1031
ccucccagag gagccaccan n                                           21
```

<210> SEQ ID NO 1032
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1032
ugguggcucc ucugggaggn n                                              21

<210> SEQ ID NO 1033
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1033
cccucccaga ggagccacca guu                                            23

<210> SEQ ID NO 1034
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1034
cucccagagg agccaccagn n                                              21

<210> SEQ ID NO 1035
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1035
cugguggcuc cucugggagn n                                              21

<210> SEQ ID NO 1036
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1036
ccucccagag gagccaccag uuc                                            23

<210> SEQ ID NO 1037
<211> LENGTH: 21
<212> TYPE: DNA
<213> ORGANISM: Artificial Sequence
<220> FEATURE:
<223> OTHER INFORMATION: Exemplary iRNA agents

```
<220> FEATURE:
<221> NAME/KEY: misc_feature
<222> LOCATION: 20, 21
<223> OTHER INFORMATION: n = 2'-deoxy-thymidine

<400> SEQUENCE: 1037
ucccagagga gccaccagun n                                              21

<210> SEQ ID NO 1038
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1038 acuggugcu ccucugggan n                                               21

<210> SEQ ID NO 1039
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1039
cucccagagg agccaccagu ucu                                            23

<210> SEQ ID NO 1040
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1040
cccagaggag ccaccaguun n                                              21

<210> SEQ ID NO 1041
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1041
aacugguggc uccucugggn n                                              21

<210> SEQ ID NO 1042
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1042
ucccagagga gccaccaguu cuc                                            23
```

<210> SEQ ID NO 1043
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1043
ccagaggagc caccaguucn n                                              21

<210> SEQ ID NO 1044
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1044
gaacuggugg cuccucuggn n                                              21

<210> SEQ ID NO 1045
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1045
cccagaggag ccaccaguuc uca                                            23

<210> SEQ ID NO 1046
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1046
cagaggagcc accaguucun n                                              21

<210> SEQ ID NO 1047
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1047
agaacuggug gcuccucugn n                                              21

<210> SEQ ID NO 1048
<211> LENGTH: 23

```
<212> TYPE: RNA
<213> ORGANISM: Artificial Sequence
<220> FEATURE:
<223> OTHER INFORMATION: Exemplary iRNA agents

<400> SEQUENCE: 1048
cuucucucca gcugacuaaa cuu                                              23

<210> SEQ ID NO 1049
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1049
ucucuccagc ugacuaaacn n                                                21

<210> SEQ ID NO 1050
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1050
guuuagucag cuggagagan n                                                21

<210> SEQ ID NO 1051
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1051
uucuguacca guuaauuuuu cca                                              23

<210> SEQ ID NO 1052
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1052
cuguaccagu uaauuuuucn n                                                21

<210> SEQ ID NO 1053
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

<400> SEQUENCE: 1053
gaaaaauuaa cugguacagn n                                              21

<210> SEQ ID NO 1054
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1054
ucuguaccag uuaauuuuuc caa                                            23

<210> SEQ ID NO 1055
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1055
uguaccaguu aauuuuuccn n                                              21

<210> SEQ ID NO 1056
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1056
ggaaaaauua acugguacan n                                              21

<210> SEQ ID NO 1057
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1057
cuguaccagu uaauuuuucc aac                                            23

<210> SEQ ID NO 1058
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1058
guaccaguua auuuuuccan n                                              21

<210> SEQ ID NO 1059
<211> LENGTH: 21

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1059
uggaaaaauu aacugguacn n                                              21

<210> SEQ ID NO 1060
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1060
uguaccaguu aauuuuucca acu                                            23

<210> SEQ ID NO 1061
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1061
uaccaguuaa uuuuuccaan n                                              21

<210> SEQ ID NO 1062
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1062
uuggaaaaau uaacugguan n                                              21

<210> SEQ ID NO 1063
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1063
guaccaguua auuuuuccaa cua                                            23

<210> SEQ ID NO 1064
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine
```

```
-continued

<400> SEQUENCE: 1064
accaguuaau uuuccaacn n                                            21

<210> SEQ ID NO 1065
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1065
guuggaaaaa uuaacuggun n                                           21

<210> SEQ ID NO 1066
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1066
uaccaguuaa uuuuccaac uac                                          23

<210> SEQ ID NO 1067
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1067
ccaguuaauu uuccaacun n                                            21

<210> SEQ ID NO 1068
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1068
aguuggaaaa auuaacuggn n                                           21

<210> SEQ ID NO 1069
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1069
accaguuaau uuuccaacu acu                                          23

<210> SEQ ID NO 1070
<211> LENGTH: 21
```

```
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1070
caguuaauuu uuccaacuan n                                               21

<210> SEQ ID NO 1071
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1071
uaguuggaaa aauuaacugn n                                               21

<210> SEQ ID NO 1072
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1072
uaauagaaua aaggcaguuu ucu                                             23

<210> SEQ ID NO 1073
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1073
auagaauaaa ggcaguuuun n                                               21

<210> SEQ ID NO 1074
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1074
aaaacugccu uuauucuaun n                                               21

<210> SEQ ID NO 1075
<211> LENGTH: 23
<212> TYPE: RNA
<213> ORGANISM: Artificial Sequence
<220> FEATURE:
<223> OTHER INFORMATION: Exemplary iRNA agents
```

```
<400> SEQUENCE: 1075
aauagaauaa aggcaguuuu cua                                              23

<210> SEQ ID NO 1076
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1076
uagaauaaag gcaguuuucn n                                                21

<210> SEQ ID NO 1077
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1077
gaaaacugcc uuuauucuan n                                                21

<210> SEQ ID NO 1078
<211> LENGTH: 23
<212> TYPE: RNA
<213> ORGANISM: Artificial Sequence
<220> FEATURE:
<223> OTHER INFORMATION: Exemplary iRNA agents

<400> SEQUENCE: 1078
auagaauaaa ggcaguuuuc uaa                                              23

<210> SEQ ID NO 1079
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1079
agaauaaagg caguuuucun n                                                21

<210> SEQ ID NO 1080
<211> LENGTH: 21
<212> TYPE: DNA
<213> ORGANISM: Artificial Sequence
<220> FEATURE:
<223> OTHER INFORMATION: Exemplary iRNA agents
<220> FEATURE:
<221> NAME/KEY: misc_feature
<222> LOCATION: 20, 21
<223> OTHER INFORMATION: n = 2'-deoxy-thymidine

<400> SEQUENCE: 1080
agaaaacugc cuuuauucun n                                                21
```

<210> SEQ ID NO 1081
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy-thymidine

<400> SEQUENCE: 1081
gauuaugacc gucugaggcn n                                              21

<210> SEQ ID NO 1082
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy-thymidine

<400> SEQUENCE: 1082
gccucagucg gucauaaucn n                                              21

<210> SEQ ID NO 1083
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1083
ggaucuucgg aaugaugagn n                                              21

<210> SEQ ID NO 1084
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1084
cucaucauuc cgaagauccn n                                              21

<210> SEQ ID NO 1085
<211> LENGTH: 21
<212> TYPE: DNA
<213> ORGANISM: Artificial Sequence

```
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy-thymidine

<400> SEQUENCE: 1085
agaccaaaga cggagugagn n                                              21

<210> SEQ ID NO 1086
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1086
cucacuccgu cuuuggucun n                                              21

<210> SEQ ID NO 1087
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy-thymidine

<400> SEQUENCE: 1087
ugaagcagga gccgguaaan n                                              21

<210> SEQ ID NO 1088
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1088
uuuaccggcu ccugcuucan n                                              21

<210> SEQ ID NO 1089
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 6, 9, 11, 12, 13,19
<223> OTHER INFORMATION: 2'- O-methyl modification corresponding base
```

```
<220> FEATURE:
<221> NAME/KEY: misc_feature
<222> LOCATION: 20,
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1089
gcuaccagua uuuagaagcn n                                                   21

<210> SEQ ID NO 1090
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 6, 10, 16
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1090
gcuucuaaau acugguagcn n                                                   21

<210> SEQ ID NO 1091
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 4, 5, 8, 10, 11, 12, 18, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1091
cuaccaguau uuagaagccn n                                                   21

<210> SEQ ID NO 1092
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 7, 11, 17
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
```

```
<221> NAME/KEY: misc_feature
<222> LOCATION: 21
<223> OTHER INFORMATION: n = 2'-deoxy-thymidine phosphorothioate
      linkages

<400> SEQUENCE: 1092
ggcuucuaaa uacugguagn n                                              21

<210> SEQ ID NO 1093
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 8, 9, 11, 12, 13, 14, 16, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1093
gcuguaacua cuuuauaacn n                                              21

<210> SEQ ID NO 1094
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 5, 10, 14, 16
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1094
guuauaaagu aguuacagcn n                                              21

<210> SEQ ID NO 1095
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 6, 8, 10, 13, 14, 17, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages
```

-continued

<400> SEQUENCE: 1095
guuacugugu aauuagugcn n                                                21

<210> SEQ ID NO 1096
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 5, 9, 11, 13, 16
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1096
gcacuaauua cacaguaacn n                                                21

<210> SEQ ID NO 1097
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 4, 5, 6, 9, 11, 13, 15, 16, 18, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1097
ccacuuaaug uauguuaccn n                                                21

<210> SEQ ID NO 1098
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6, 8, 10, 13
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1098
gguaacauac auuaaguggn n                                                21

```
<210> SEQ ID NO 1099
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 5, 6, 7, 10, 13, 14, 15
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1099
cagcccugau aguuuagaan n                                              21

<210> SEQ ID NO 1100
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 9, 12
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1100
uucuaaacua ucagggcugn n                                              21

<210> SEQ ID NO 1101
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 4, 5, 8, 11, 12, 13
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1101
gcccugauag uuuagaaaan n                                              21

<210> SEQ ID NO 1102
<211> LENGTH: 21
<212> TYPE: DNA
<213> ORGANISM: Artificial Sequence
<220> FEATURE:
```

```
<223> OTHER INFORMATION: Synthetically generated oligonucleotide
<220> FEATURE:
<221> NAME/KEY: modified_base
<222> LOCATION: 6, 11, 14
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1102
uuuucuaaac uaucagggcn n                                              21

<210> SEQ ID NO 1103
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 7, 10, 11, 12, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1103
cccugauagu uuagaaaacn n                                              21

<210> SEQ ID NO 1104
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 7, 12, 15
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 20
<223> OTHER INFORMATION: n = 2'-deoxy-thymidine

<400> SEQUENCE: 1104
guuuucuaaa cuaucagggn n                                              21

<210> SEQ ID NO 1105
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6, 7, 8, 15, 17, 18, 19
<223> OTHER INFORMATION: 2'- O-methyl modification corresponding base
<220> FEATURE:
```

```
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1105
gauaguuuag aaaacauccn n                                              21

<210> SEQ ID NO 1106
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 11, 16
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1106
ggauguuuuc uaaacuaucn n                                              21

<210> SEQ ID NO 1107
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 5, 6, 13, 15, 16, 17, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1107
uaguuuagaa aacaucccan n                                              21

<210> SEQ ID NO 1108
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 13, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
```

```
<222> LOCATION: 21
<223> OTHER INFORMATION: n = 2'-deoxy-thymidine phosphorothioate
      linkages

<400> SEQUENCE: 1108
ugggauguuu ucuaaacuan n                                                   21

<210> SEQ ID NO 1109
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 5, 6, 10, 12, 15, 17, 18, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1109
cagacuagau guaguauuun n                                                   21

<210> SEQ ID NO 1110
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 7, 9, 13
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1110
aaauacuaca ucuagucugn n                                                   21

<210> SEQ ID NO 1111
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 8, 9, 13, 15, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1111
```
ccccagacua gauguaguan n                                     21

<210> SEQ ID NO 1112
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 6, 10
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1112
uacuacaucu agucuggggn n                                     21

<210> SEQ ID NO 1113
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 6, 7, 11, 13, 16, 18, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1113
ccagacuaga uguaguauun n                                     21

<210> SEQ ID NO 1114
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6, 8, 12
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1114
aauacuacau cuagucuggn n                                     21

<210> SEQ ID NO 1115

```
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 7, 8, 12, 14, 17, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1115
cccagacuag auguaguaun n                                              21

<210> SEQ ID NO 1116
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 5, 7, 11
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1116
auacuacauc uagucugggn n                                              21

<210> SEQ ID NO 1117
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 6, 7, 8, 11, 13, 15, 17, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1117
ugccacuuaa uguauguuan n                                              21

<210> SEQ ID NO 1118
<211> LENGTH: 21
<212> TYPE: DNA
<213> ORGANISM: Artificial Sequence
<220> FEATURE:
<223> OTHER INFORMATION: Synthetically generated oligonucleotide
```

```
<220> FEATURE:
<221> NAME/KEY: modified_base
<222> LOCATION: 1, 4, 6, 8, 11, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1118
uaacauacau uaaguggcan n                                                    21

<210> SEQ ID NO 1119
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 6, 7, 8, 10, 11, 14, 15, 16, 17
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1119
ugcuguuuau uaaucuuagn n                                                    21

<210> SEQ ID NO 1120
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 8, 11, 15, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1120
cuaagauuaa uaaacagcan n                                                    21

<210> SEQ ID NO 1121
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 4, 6, 7, 10, 11, 13, 14, 15, 16, 18
<223> OTHER INFORMATION: 2'- O-methyl modification corresponding base
<220> FEATURE:
```

```
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1121
ucauguuagu uaccuuauan n                                              21

<210> SEQ ID NO 1122
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 8, 12, 15
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1122
uauaagguaa cuaacaugan n                                              21

<210> SEQ ID NO 1123
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6,  9, 10, 11, 12, 13,, 14, 15, 18, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1123
ccaguuaauu uuuccaacun n                                              21

<210> SEQ ID NO 1124
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 13
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
```

```
<222> LOCATION: 21
<223> OTHER INFORMATION: n = 2'-deoxy-thymidine phosphorothioate
      linkages

<400> SEQUENCE: 1124
aguuggaaaa auuaacuggn n                                              21

<210> SEQ ID NO 1125
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 5, 10, 11, 13, 17, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1125
uaccuaagau uacaaaucan n                                              21

<210> SEQ ID NO 1126
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 8, 14, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1126
ugauuuguaa ucuuagguan n                                              21

<210> SEQ ID NO 1127
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 6, 7, 9, 10, 13, 15, 16, 17
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1127
```
ucuugcuacc aguauuuagn n                                              21

<210> SEQ ID NO 1128
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 6, 12, 15
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1128
cuaaauacug guagcaagan n                                              21

<210> SEQ ID NO 1129
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 5, 8, 9, 12, 14, 15, 17, 18, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1129
uguguaauua gugccacuun n                                              21

<210> SEQ ID NO 1130
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 7, 10, 14, 16, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1130
aaguggcacu aauuacacan n                                              21

<210> SEQ ID NO 1131

```
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 4, 5, 7, 8, 10, 11, 14, 16, 17, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1131
aucuugcuac caguauuuan n                                                   21

<210> SEQ ID NO 1132
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 5, 11, 14
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1132
uaaauacugg uagcaagaun n                                                   21

<210> SEQ ID NO 1133
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 4, 7, 8, 10, 11, 12, 13, 15, 18, 19
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1133
cuguaacuac uuuauaacun n                                                   21

<210> SEQ ID NO 1134
<211> LENGTH: 21
<212> TYPE: DNA
<213> ORGANISM: Artificial Sequence
<220> FEATURE:
<223> OTHER INFORMATION: Synthetically generated oligonucleotide
```

```
<220> FEATURE:
<221> NAME/KEY: modified_base
<222> LOCATION: 4, 6, 11, 15, 17
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1134
aguuauaaag uaguuacagn n                                               21

<210> SEQ ID NO 1135
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 6, 7, 11, 12, 14, 17, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1135
gugaauuagg cuguaacuan n                                               21

<210> SEQ ID NO 1136
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 5, 7, 12, 17,
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1136
uaguuacagc cuaauucacn n                                               21

<210> SEQ ID NO 1137
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 4, 5, 8, 10, 11, 12, 18, 19
<223> OTHER INFORMATION: 2'- O-methyl modification corresponding base
<220> FEATURE:
```

```
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages, conjugated 1-{6-[cholester-3-yloxycarbonylamino]-
      hexanoyl}-4-hydroxy-pyrrolidin-3-phosphorothioate diester

<400> SEQUENCE: 1137
cuaccaguau uuagaagccn n                                              21

<210> SEQ ID NO 1138
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 7, 11, 17
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1138
ggcuucuaaa uacugguagn n                                              21

<210> SEQ ID NO 1139
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 6, 7, 8, 10, 11, 14, 15, 16, 17
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
<220> FEATURE:
<221> NAME/KEY: misc_feature
<222> LOCATION: 21
<223> OTHER INFORMATION: n = 2'-deoxy-thymidine phosphorothioate
      linkages, conjugated 1-{6-[cholester-3-yloxycarbonylamino]-
      hexanoyl}-4-hydroxy-pyrrolidin-3-phosphorothioate diester

<400> SEQUENCE: 1139
ugcuguuuau uaaucuuagn n                                              21

<210> SEQ ID NO 1140
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 8, 11, 15, 18
<223> OTHER INFORMATION: 2'- O-methyl modification corresponding base
<220> FEATURE:
<221> NAME/KEY: misc_feature
<222> LOCATION: 20
<223> OTHER INFORMATION: n = 2'-deoxy-thymidine
```

```
<220> FEATURE:
<221> NAME/KEY: misc_feature
<222> LOCATION: 21
<223> OTHER INFORMATION: n = 2'-deoxy-thymidine phosphorothioate
      linkages

<400> SEQUENCE: 1140
cuaagauuaa uaaacagcan n                                           21

<210> SEQ ID NO 1141
<211> LENGTH: 46
<212> TYPE: DNA
<213> ORGANISM: Rattus norvegicus

<400> SEQUENCE: 1141
ccattttcct gggatgtttt ctaaattttt ctcttggaaa gaaagt                 46

<210> SEQ ID NO 1142
<211> LENGTH: 45
<212> TYPE: DNA
<213> ORGANISM: Rattus norvegicus

<400> SEQUENCE: 1142
acagaaatgc ttgacttctg gagttttttc tcttggaaag aaagt                  45

<210> SEQ ID NO 1143
<211> LENGTH: 41
<212> TYPE: DNA
<213> ORGANISM: Rattus norvegicus

<400> SEQUENCE: 1143
cttcaggttt taccggctcc tttttctctt ggaaagaaag t                      41

<210> SEQ ID NO 1144
<211> LENGTH: 43
<212> TYPE: DNA
<213> ORGANISM: Rattus norvegicus

<400> SEQUENCE: 1144
ctgtttgcca tatctctgcc tttttttctc ttggaaagaa agt                    43

<210> SEQ ID NO 1145
<211> LENGTH: 43
<212> TYPE: DNA
<213> ORGANISM: Rattus norvegicus

<400> SEQUENCE: 1145
ttggtctttg ctgaacactc catttttctc ttggaaagaa agt                    43

<210> SEQ ID NO 1146
<211> LENGTH: 40
<212> TYPE: DNA
<213> ORGANISM: Rattus norvegicus

<400> SEQUENCE: 1146
cccgcgtcta gcttgcagat ttttctcttg gaaagaaagt                        40

<210> SEQ ID NO 1147
<211> LENGTH: 44
<212> TYPE: DNA
<213> ORGANISM: Rattus norvegicus

<400> SEQUENCE: 1147
aggatgatgg gcacatttgg tttttaggca taggacccgt gtct                   44
```

```
<210> SEQ ID NO 1148
<211> LENGTH: 45
<212> TYPE: DNA
<213> ORGANISM: Rattus norvegicus

<400> SEQUENCE: 1148
gccttgtgtg ctcatcattc cttttttaggc ataggacccg tgtct                    45

<210> SEQ ID NO 1149
<211> LENGTH: 46
<212> TYPE: DNA
<213> ORGANISM: Rattus norvegicus

<400> SEQUENCE: 1149
tgcttcattt tggctaactc cctttttagg cataggaccc gtgtct                    46

<210> SEQ ID NO 1150
<211> LENGTH: 44
<212> TYPE: DNA
<213> ORGANISM: Rattus norvegicus

<400> SEQUENCE: 1150
tgtacccaaa agcgccaatc ttttaggca taggacccgt gtct                       44

<210> SEQ ID NO 1151
<211> LENGTH: 43
<212> TYPE: DNA
<213> ORGANISM: Rattus norvegicus

<400> SEQUENCE: 1151
gcagctctcg tggccatctt ttttaggcat aggacccgtg tct                       43

<210> SEQ ID NO 1152
<211> LENGTH: 44
<212> TYPE: DNA
<213> ORGANISM: Rattus norvegicus

<400> SEQUENCE: 1152
aggcaccccg acttttttctt ttttaggca taggacccgt gtct                      44

<210> SEQ ID NO 1153
<211> LENGTH: 21
<212> TYPE: DNA
<213> ORGANISM: Rattus norvegicus

<400> SEQUENCE: 1153
ctatcagggc tgtcgatgga a                                               21

<210> SEQ ID NO 1154
<211> LENGTH: 23
<212> TYPE: DNA
<213> ORGANISM: Rattus norvegicus

<400> SEQUENCE: 1154
gaagatcctt cttgttccca act                                             23

<210> SEQ ID NO 1155
<211> LENGTH: 23
<212> TYPE: DNA
<213> ORGANISM: Rattus norvegicus

<400> SEQUENCE: 1155
caaaaacctc tctcactccg tct                                             23
```

<210> SEQ ID NO 1156
<211> LENGTH: 41
<212> TYPE: DNA
<213> ORGANISM: Rattus norvegicus

<400> SEQUENCE: 1156
ccagcttccc attctcagcc tttttctctt ggaaagaaag t          41

<210> SEQ ID NO 1157
<211> LENGTH: 41
<212> TYPE: DNA
<213> ORGANISM: Rattus norvegicus

<400> SEQUENCE: 1157
tctcgctcct ggaagatggt tttttctctt ggaaagaaag t          41

<210> SEQ ID NO 1158
<211> LENGTH: 41
<212> TYPE: DNA
<213> ORGANISM: Rattus norvegicus

<400> SEQUENCE: 1158
cccatttgat gttagcggga tttttctctt ggaaagaaag t          41

<210> SEQ ID NO 1159
<211> LENGTH: 42
<212> TYPE: DNA
<213> ORGANISM: Rattus norvegicus

<400> SEQUENCE: 1159
cggagatgat gacccttttg gttttttctct tggaaagaaa gt          42

<210> SEQ ID NO 1160
<211> LENGTH: 44
<212> TYPE: DNA
<213> ORGANISM: Rattus norvegicus

<400> SEQUENCE: 1160
gatgggtttc ccgttgatga tttttaggca taggacccgt gtct          44

<210> SEQ ID NO 1161
<211> LENGTH: 47
<212> TYPE: DNA
<213> ORGANISM: Rattus norvegicus

<400> SEQUENCE: 1161
gacatactca gcaccagcat cactttttag gcataggacc cgtgtct          47

<210> SEQ ID NO 1162
<211> LENGTH: 44
<212> TYPE: DNA
<213> ORGANISM: Rattus norvegicus

<400> SEQUENCE: 1162
cccagccttc tccatggtgg tttttaggca taggacccgt gtct          44

<210> SEQ ID NO 1163
<211> LENGTH: 21
<212> TYPE: DNA
<213> ORGANISM: Rattus norvegicus

<400> SEQUENCE: 1163
ttgactgtgc cgttgaactt g          21

```
<210> SEQ ID NO 1164
<211> LENGTH: 19
<212> TYPE: DNA
<213> ORGANISM: Rattus norvegicus

<400> SEQUENCE: 1164
ccccaccctt caggtgagc                                                 19

<210> SEQ ID NO 1165
<211> LENGTH: 17
<212> TYPE: DNA
<213> ORGANISM: Rattus norvegicus

<400> SEQUENCE: 1165
ggcatcagcg gaagggg                                                   17
```

IRNA AGENTS TARGETED TO THE RHO-A GENE

RELATED APPLICATIONS

This application claims the benefit of U.S. Provisional Application No. 60/701,470, filed Jul. 21, 2005, U.S. Provisional Application No. 60/726,838, filed Oct. 14, 2005, and U.S. Provisional Application No. 60/748,316, filed Dec. 7, 2005. The contents of each of these priority applications are incorporated herein by reference in their entirety.

SEQUENCE LISTING

This application incorporates by reference the sequence listing saved as an ASCII text file on CD-ROM. The sequence listing saved on CD-ROM was created on Oct. 5, 2006, and is identified as "14174-139001.txt." The file contains 280 KB of data. Three identical copies of the sequence listing have been submitted, including one "Computer-Readable Format" (CRF) and two "Official Copies" (Copy 1 and Copy 2).

TECHNICAL FIELD

The invention relates to compositions and methods for modulating the expression of RhoA, and more particularly to the downregulation of RhoA mRNA and RhoA protein levels by oligonucleotides via RNA interference, e.g., chemically modified oligonucleotides.

BACKGROUND

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function.

Numerous myelin-derived axon growth inhibitors have been characterized (see, for review, David et al., WO995394547, 1999; Bandman et al. U.S. Pat. No. 5,858, 708, 1999; Schwab, *Neurochem. Res.* 21:755-761, 1996). Several components of CNS white matter, NI35, NI250 (Nogo) and Myelin-associated glycoprotein (MAG), which have inhibitory activity for axonal extension, have been described as well (Schwab et al., WO9005191, 1990; Schwab et al., U.S. Pat. No. 5,684,133, 1997). In particular, RhoA is a member of the large family of Rho (Ras homologue) GTPases, itself belonging to the superfamily of Ras GTPases. All eukaryotes contain at least one Rho GTPase. During the process of evolution the number of Rho GTPases increased from 5 to 6 per organism (yeast) to over 20 (mammals) (Karnoub, A. E., et al., Breast Cancer Res. Treat. 2004, 84:61). Like other GTPases, RhoA has intrinsic GTPase activity and shuttles between an inactive GDP-bound state and an active GTP-bound state. In vitro, the exchange of GDP to GTP occurs very slowly, and is catalyzed by guanine nucleotide exchange factors (GEFs), which exchange GDP for GTP. GTPase activating proteins (GAPs) catalyze hydrolysis of the γ-phosphate of GTP. (Wheeler, A. P., Ridley, A. J., Exp. Cell Res. 2004, 301:43). A third set of regulatory proteins, the guanine nucleotide-dissociation inhibitors (GDIs), sequester GTPAses in the cytosol in the inactive, GDP-bound state.

The N-terminal half of Rho GTPases contains the majority of the amino acids involved in GTP binding and hydrolysis, together with the Switch 1 and 2 regions that change conformation between the GTP-bound and GDP-bound states (Bishop, A. L., Hall, A., Biochem. J. 2000, 348 (Pt. 2):241). The C-terminus of Rho family GTPases is essential for correct localization of the proteins. It is post-translationally modified by prenylation of a conserved C-terminal cysteine followed by methylation and proteolytic removal of the last three amino acids (Shao, F., Dixon, J. E., Adv. Exp. Med. Biol. 2003, 529:79). The prenyl group anchors the GTPases into membranes and this modification is essential for cell growth, transformation, and cytoskeleton organization (Allal, C., et al., J. Biol. Chem. 2000, 275:31001). Prenylation of Rho proteins appears to be important for their stability, inhibitors of enzymes that synthesize prenyl groups induce a decrease in Rho protein levels and their function (Stamatakis, K., et al., J. Biol. Chem 2002, 277:49389). In the case of RhoA, prenylation adds a geranylgeranyl group. RhoA is mainly found in the cytoplasm or at the plasma membrane (Adamson, P., et al., J. Cell Biol. 1992, 119:617).

RhoA may bind to the intracellular portion of p75NTR and is activated by Nogo-R in a p75NTR-dependent manner (Wang, K. C., et al., Nature 2002, 420:74), which is how MAG, Nogo-66, and oligodendrocyte-myelin glycoprotein achieve RhoA activation. The central inhibitory domain of Nogo-A, NiG, distinct from Nogo-66, and Versican V2, a chondroitin-sulfate proteoglycan and another component of myelin, are able to activate RhoA in the absence of p75NTR, by an alternative pathway of RhoA activation remaining to be elucidated (Schweigreiter, R., et al., Mol. Cell Neurosci. 2004, 27:163). Further pathways of activation may exist.

RhoA is part of the growth inhibitory machinery present in the central nervous system (CNS), but not in peripheral nerves, which prevents the regeneration of CNS tissue after injury. Both the expression and the activation of RhoA is induced in brain and spinal cord injury (Mueller, K., et al., Nature Reviews 2005, 4:387). Activation of RhoA leads to neuronal growth cone collapse, retraction bulb formation and neurite withdrawal. Inactivation of RhoA leads to neurite outgrowth in primary neurons on otherwise inhibitory substrates in vitro, and promotes axon regeneration and functional recovery after spinal cord injury in rats and mice in vivo (Lehmann, M. A., et al., J. Neurosci. 1999, 19:7537; Hara, M, et al., J. Neurosurg. 2000, 93:94; Dergham, P., et al., J. Neurosci. 2002, 22:6570). Furthermore, inactivation of Rho has been shown to protect endogenous cells of the spinal cord from apoptosis induced by spinal cord injury (Dubreuil, C. I., et al, J. Cell Biol. 2003, 162:233). These findings have clinical relevance because neuroprotective treatments after spinal cord injury lead to improved functional recovery (Liu, X. Z., et al., J. Neurosci. 1997, 17:5395).

Evidently, RhoA is a potential target for therapeutic intervention strategies aimed at diseases and conditions involving, e.g., the destruction and/or impaired regeneration of cells of the CNS. The present invention advances the art by providing methods and medicaments encompassing short dsRNAs leading to the downregulation of RhoA mRNA and protein levels in cells expressing the RhoA gene. These methods and medicaments may be used in the treatment of disorders or pathological processes mediated, at least in part, by RhoA, e.g., by preventing the RhoA inhibition of axonal elongation and regeneration, and consequently stimulating nerve growth and proliferation.

SUMMARY

The present invention is based, at least in part, on an investigation of the RhoA gene using iRNA agents and further testing of the iRNA agents that target the RhoA site. The present invention provides compositions and methods that are useful in reducing RhoA mRNA levels, RhoA protein levels and the treatment of pathological process mediated, at least in part, by RhoA, e.g. preventing RhoA inhibition of axonal elongation and regeneration, in a subject, e.g., a mammal, such as a human.

In one aspect, the invention provides iRNA agents comprising a sense strand, wherein the sense strand comprises at least 15 contiguous nucleotides that differ by no more than 1, 2, or 3 nucleotides from the sense strand sequences of any one agent selected from the group consisting of: agents number 6477 to 6836 as given in Table 1 below, and an antisense strand, wherein the antisense strand comprises at least 15 contiguous nucleotides that differ by no more than 1, 2, or 3 nucleotides from the antisense sequences of any one agent selected from the group consisting of: agents number 6477 to 6836.

In a further aspect, the invention provides iRNA agents for inhibiting the expression of a rhoA gene in a cell comprising a sense strand, wherein the sense strand comprises at least 15 contiguous nucleotides that differ by no more than 1, 2, or 3 nucleotides from the sense strand sequences of any one agent selected from the group consisting of: agents number 6477 to 6836, and an antisense strand wherein the antisense strand comprises at least 15 contiguous nucleotides of the antisense sequences of any one agent selected from the group consisting of: agents number 6477 to 6836, and wherein the iRNA agent reduces the amount of RhoA mRNA present in cultured human cells after incubation with these agents by 40% or more compared to cells which have not been incubated with the agent.

In a further aspect, the invention provides iRNA agents for inhibiting the expression of a rhoA gene in a cell comprising a sense strand and an antisense strand each comprising a sequence of at least 16, 17 or 18 nucleotides which is essentially identical to one of the sequences of any one agent selected from the group consisting of: agents number 6477 to 6836, except that not more than 1, 2 or 3 nucleotides per strand, respectively, have been substituted by other nucleotides (e.g. adenosine replaced by uracil), while essentially retaining the ability to inhibit RhoA expression. Preferably, for such agents the sense and/or antisense strand sequence is chosen from the group consisting of: the sense and antisense strand sequences of agent numbers 6523, 6524, 6530, 6614, 6650, 6656, 6657, 6661, 6662, 6703, 6712, 6713, 6732, 6751, 6756, 6767, 6769, 6787, 6789, 6790, 6832.

Evidently, in the above embodiments, the sense strands and/or antisense strands of the iRNA agents of the invention can also be identical to the sense strands and antisense strands of the agents, agent numbers 6477 to 6836.

The iRNA agents of the invention may comprise a modification, e.g a modification that causes the iRNA agent to have increased stability in a biological sample. For example, they may comprise a phosphorothioate, a 2'-modified nucleotide, a locked nucleotide, an abasic nucleotide, morpholino nucleotide, a phosphoramidate, or a non-natural base comprising nucleotide. For purposes of the above embodiments, an iRNA agent is considered to comprise one of the sequences of the agents, agent numbers 6477 to 6836, irrespective of the potential presence of nucleotide modifications, i.e. a 2'-O-methyl guanosine would be considered a guanosine for such comparison. However, certain patterns of modifications are particularly preferred embodiments of the present invention. Consequently, in another embodiment, the invention provides iRNA agents for inhibiting the expression of a rhoA gene in a cell wherein the sense and/or antisense strand sequence is chosen from the group consisting of: the sense and antisense strand sequences of agent numbers AL-DP-5972, AL-DP-5973, AL-DP-5974, AL-DP-5975, AL-DP-5976, AL-DP-5978, AL-DP-5979, AL-DP-5981, AL-DP-5982, AL-DP-5983, AL-DP-5984, AL-DP-5986, AL-DP-5987, AL-DP-5988, AL-DP-5989, AL-DP-5990, AL-DP-5991, AL-DP-5992, AL-DP-5993, AL-DP-5994, AL-DP-5995, AL-DP-6176, AL-DP-6177.

In the iRNA agents of the present invention, the antisense RNA strand may be 30 or fewer nucleotides in length, and the duplex region of the iRNA agent may be 15-30 nucleotide pairs in length.

A 2'-modified nucleotide according to the instant invention may comprise at least one 5'-uridine-adenine-3' (5'-ua-3') dinucleotide wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide.

The iRNA agents of the invention may be designed such that every 5'-nucleotide in 5'-ua-3',5'-uu-3',5'-ca-3', and 5'-ug-3' motifs is a 2'-modified in sense strand, and every 5'-nucleotide in 5'-ua-3' and 5'-ca-3' motifs is 2'-modified in antisense strand, or every 5'-nucleotide in 5'-ua-3',5'-uu-3',5'-ca-3', and 5'-ug-3' motifs is 2'-modified in the sense and antisense strand, or every pyrimidine nucleotide is 2'-modified in the sense strand, and every 5'-nucleotide in 5'-ua-3' and 5'-ca-3' motifs is 2'-modified in the antisense strand, or every pyrimidine nucleotide is 2'-modified in sense strand, and every 5'-nucleotide in 5'-ua-3',5'-uu-3',5'-ca-3', and 5'-ug-3' motifs is 2'-modified in the antisense strand, or every pyrimidine nucleotide in the sense strand is 2'-modified, and no nucleotide is 2'-modified in the antisense strand.

The 2'-modification in the iRNA agents of the invention may be selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The iRNA agents of the invention may comprise a nucleotide overhang having 1 to 4 unpaired nucleotides, preferably 2 or 3 unpaired nucleotides. The nucleotide overhang may be at the 3'-end of the antisense strand of the iRNA agent. The iRNA agents may comprise a cholesterol moiety, which is preferably conjugated to the 3'-end of the sense strand of the iRNA agent. In a preferred embodiment, the iRNA agent is targeted for uptake by nerve cells or nerve sheath cells.

The present invention further provides methods for reducing the level of RhoA mRNA in a cell. The present methods utilize the cellular mechanisms involved in RNA interference to selectively degrade RhoA mRNA in a cell and are comprised of the step of contacting a cell with one of the iRNA agents of the present invention. Such methods can be performed directly on a cell or can be performed on a mammalian subject by administering to a subject one of the iRNA agents of the present invention. Reduction of RhoA mRNA in a cell results in a reduction in the amount of RhoA protein produced, and in an organism, may result in a decrease in RhoA specific pathological/disease effects, e.g. preventing RhoA inhibition of axonal elongation and regeneration.

In another aspect of the invention, a method of treating a human subject having a pathological process mediated in part by RhoA is provided, comprising administering an iRNA agent of the invention, e.g. wherein the iRNA agent comprises a sense strand wherein the sense strand comprises at least 15 contiguous nucleotides that differ by no more than 1, 2, or 3 nucleotides from the sense strand sequences any one of the agents, agent numbers 6477 to 6836, and an antisense strand, wherein the antisense strand comprises at least 15 contiguous nucleotides that differ by no more than 1, 2, or 3 nucleotides from the antisense strand sequences of any one of the agents, agent numbers 6477 to 6836.

In one embodiment of the above methods of the invention, the pathological process is the inhibition of nerve growth or elongation, preferably as a result of nerve injury or damage. In another preferred embodiment, the iRNA agent is administered in an amount sufficient to reduce the expression of RhoA in a cell or tissue of the subject. Preferably, the subject is a human.

In another aspect, the instant invention provides pharmaceutical compositions, comprising:
 a.) an iRNA agent of the invention; and
 b.) a pharmaceutically acceptable carrier In another embodiment, the invention provides a cell comprising an iRNA agent of the invention.

In another embodiment, the invention provides a method for inhibiting the expression of a RhoA gene in a cell, the method comprising:
 (a) introducing into the cell an iRNA agent of the invention; and
 (b) maintaining the cell produced in step (a) for a time sufficient to obtain degradation of the mRNA transcript of the RhoA gene, thereby inhibiting expression of the RhoA gene in the cell.

In another embodiment, the invention provides a vector for inhibiting the expression of a RhoA gene in a cell, said vector comprising a regulatory sequence operably linked to a nucleotide sequence that encodes at least one strand of an iRNA agent of the invention.

In another embodiment, the invention provides a cell comprising the above vector.

The methods and compositions of the invention, e.g., the methods and iRNA compositions can be used with any dosage and/or formulation described herein, as well as with any route of administration described herein.

The details of one or more embodiments of the invention are set forth in the description below. Other features, objects, and advantages of the invention will be apparent from this description and from the claims. This application incorporates all cited references, patents, and patent applications by references in their entirety for all purposes.

DETAILED DESCRIPTION

Figure 1:
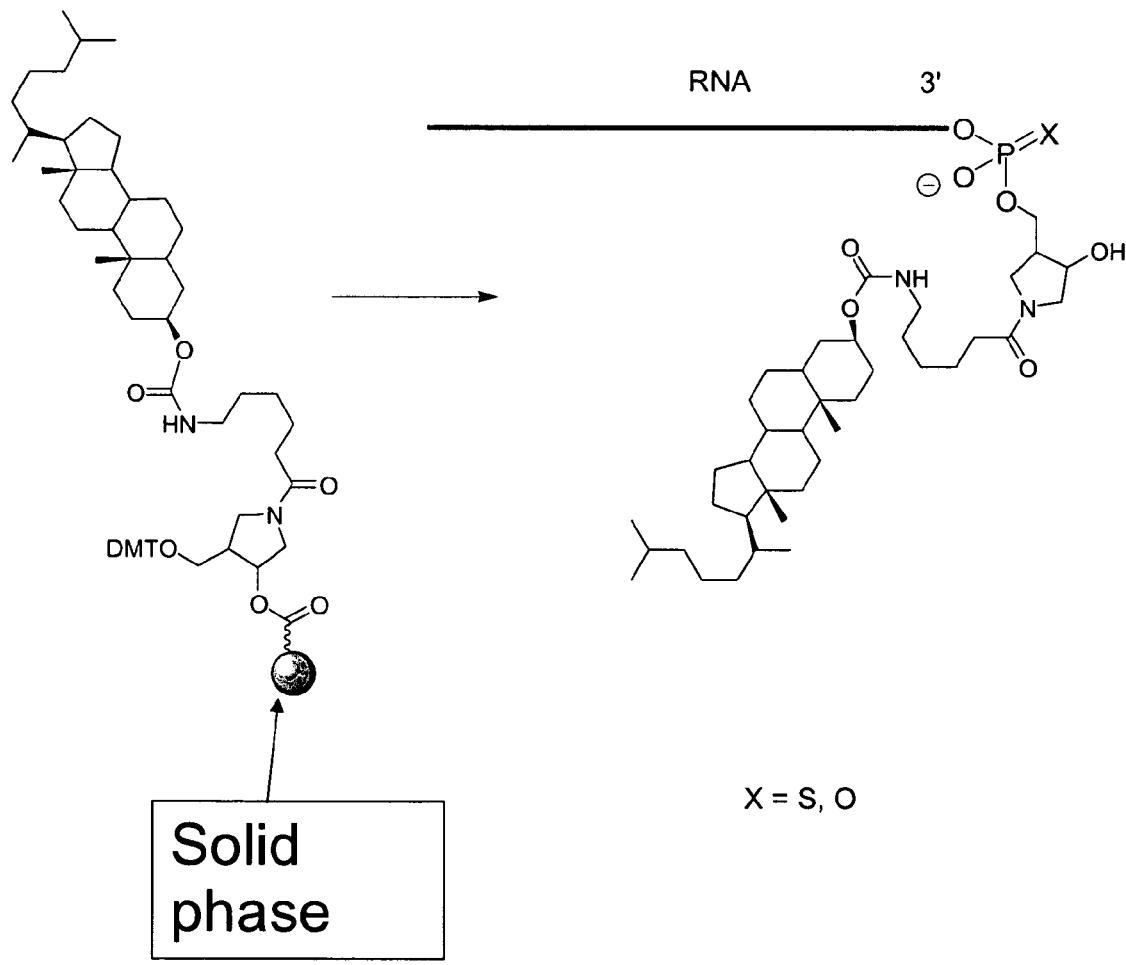
FIG. 1 is a schematic illustrating the synthesis and structure of cholesterol conjugated RNA strands. The sphere represents the solid phase (controlled pore glass, CPG).

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogate, each of which is described herein or is well known in the RNA synthetic art. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can down-regulate the expression of a target gene, e.g., RhoA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded iRNA agent.

A "ds iRNA agent" (abbreviation for "double stranded iRNA agent"), as used herein, is an iRNA agent which includes more than one, and preferably two, strands in which interstrand hybridization can form a region of duplex structure. A "strand" herein refers to a contiguouous sequence of nucleotides (including non-naturally occurring or modified nucleotides). The two or more strands may be, or each form a part of, separate molecules, or they may be covalently interconnected, e.g., by a linker, e.g., a polyethyleneglycol linker, to form one molecule. At least one strand can include a region which is sufficiently complementary to a target RNA. Such strand is termed the "antisense strand." A second strand of the dsRNA agent, which comprises a region complementary to the antisense strand, is termed the "sense strand." However, a ds iRNA agent can also be formed from a single RNA molecule which is at least partly self-complementary, forming, e.g., a hairpin or panhandle structure, including a duplex region. In such case, the term "strand" refers to one of the regions of the RNA molecule that is complementary to another region of the same RNA molecule.

Although, in mammalian cells, long ds iRNA agents can induce the interferon response which is frequently deleterious, short ds iRNA agents do not trigger the interferon response, at least not to an extent that is deleterious to the cell and/or host (Manche et al., *Mol. Cell. Biol.* 12:5238, 1992; Lee et al., *Virology* 199:491, 1994; Castelli et al., *J. Exp. Med.* 186:967, 1997; Zheng et al., *RNA* 10: 1934, 2004; Heidel et al., "Lack of interferon response in animals to naked siRNAs" *Nature Biotechn. advance online publication* doi:10.1038/nbt1038, Nov. 21, 2004). The iRNA agents of the present invention include molecules which are sufficiently short that they do not trigger a deleterious non-specific interferon response in normal mammalian cells. Thus, the administration of a composition including an iRNA agent (e.g., formulated as described herein) to a subject can be used to decreased expression of the RhoA genes in RhoA expressing cells in the subject, while circumventing an interferon response. Molecules that are short enough that they do not trigger a deleterious interferon response are termed siRNA agents or siRNAs herein. "siRNA agent" or "siRNA" as used herein, refers to an iRNA agent, e.g., a ds iRNA agent, that is sufficiently short that it does not induce a deleterious interferon response in a human cell, e.g., it has a duplexed region of less than 60 but preferably less than 50, 40, or 30 nucleotide pairs.

The isolated iRNA agents described herein, including ds iRNA agents and siRNA agents, can mediate the decreased expression of a RhoA nucleic acid, e.g., by RNA degradation. For convenience, such RNA is also referred to herein as the RNA to be silenced. Such a nucleic acid is also referred to as a target gene. Preferably, the RNA to be silenced is a gene product of an endogenous RhoA gene.

As used herein, the phrase "mediates RNAi" refers to the ability of an agent to silence, in a sequence specific manner, a target gene. "Silencing a target gene" means the process whereby a cell containing and/or expressing a certain product of the target gene when not in contact with the agent, will contain and/or express at least 10%, 15%, 20%, 25%, 30%, 35%, 40%, 45%, 50%, 55%, 60%, 65%, 70%, 75%, 80%, 85%, or 90% less of such gene product when contacted with the agent, as compared to a similar cell which has not been contacted with the agent. Such product of the target gene can, for example, be a messenger RNA (mRNA), a protein, or a regulatory element.

As used herein, the term "complementary" is used to indicate a sufficient degree of complementarity such that stable and specific binding occurs between a compound of the invention and a target RNA molecule, e.g., a RhoA mRNA. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ from the target sequences by at least 4 nucleotides.

As used herein, an iRNA agent is "sufficiently complementary" to a target RNA, e.g., a target mRNA (e.g., a target RhoA mRNA) if the iRNA agent reduces the production of a protein encoded by the target RNA in a cell. The iRNA agent may also be "exactly complementary" to the target RNA, e.g., the target RNA and the iRNA agent anneal, preferably to form a hybrid made exclusively of Watson-Crick basepairs in the region of exact complementarity. A "sufficiently complementary" iRNA agent can include an internal region (e.g., of at least 10 nucleotides) that is exactly complementary to a target RhoA RNA. Moreover, in some embodiments, the iRNA agent specifically discriminates a single-nucleotide difference. In this case, the iRNA agent only mediates RNAi if exact complementarity is found in the region (e.g., within 7 nucleotides of) the single-nucleotide difference. Preferred iRNA agents will be based on or consist of or comprise the sense and antisense sequences provided in Table 1.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g., adenosine replaced by uracil). "Essentially retaining the ability to inhibit RhoA expression in cultured human RhoA expressing cells," as used herein referring to an iRNA agent not identical to but derived from one of the iRNA agents of Table 1 by deletion, addition or substitution of nucleotides, means that the derived iRNA agent possesses an inhibitory activity not more than 20% (in terms of remaining target mRNA) different from the inhibitory activity of the iRNA agent of Table 1 from which it was derived. For example, an iRNA agent derived from an iRNA agent of Table 1 which lowers the amount of RhoA mRNA present in cultured human Rho-A expressing cells by 70% may itself lower the amount of RhoA mRNA present in cultured human RhoA expressing cells by at least 50% in order to be considered as essentially retaining the ability to inhibit RhoA expression in cultured human RhoA expressing cells. Optionally, an iRNA agent of the invention may lower the amount of RhoA mRNA present in cultured human RhoA expressing cells by at least 50%, or at least 40%.

As used herein, a "subject" refers to a mammalian organism undergoing treatment for a disorder mediated by RhoA protein expression. The subject can be any mammal, such as a cow, horse, mouse, rat, dog, pig, goat, or a primate. In the preferred embodiment, the subject is a human.

Design and Selection of iRNA Agents

As used herein, "disorders associated with RhoA expression" refers to any biological or pathological state that (1) is mediated in part by the presence of RhoA mRNA and/or protein and (2) whose outcome can be affected by reducing the level of RhoA mRNA and/or protein present. Specific disorders associated with RhoA expression are noted below and are primarily based on the responsibility of RhoA action in inhibiting axonal elongation and regeneration.

The present invention is based on the design, synthesis and generation of iRNA agents that target RhoA and the demonstration of silencing of a RhoA gene in vitro in cultured cells after incubation with an iRNA agent, and the resulting RhoA-specific effect.

An iRNA agent can be rationally designed based on sequence information and desired characteristics. For example, an iRNA agent can be designed according to the relative melting temperature of the candidate duplex. Generally, the duplex should have a lower melting temperature at the 5' end of the antisense strand than at the 3' end of the antisense strand.

Candidate iRNA agents can also be designed by performing, for example, a gene walk analysis of the genes that will serve as the target gene. Overlapping, adjacent, or closely spaced candidate agents corresponding to all or some of the transcribed region can be generated and tested. Each of the iRNA agents can be tested and evaluated for the ability to down regulate the target gene expression (see below, "Evaluation of Candidate iRNA agents").

Herein, potential iRNA agents targeting RhoA were designed using the known sequences of RhoA for human, rat and mouse and other known RhoA sequences. The target sequences shown in Table 1 hereinabove were selected from those regions of the human RhoA mRNA sequences that show complete homology with the corresponding sequences in rat and mouse. Therefore, the siRNA agents, agent numbers 6477-6836 should show cross reactivity between thesethree species. Based on the results provided, the presentinvention provides iRNA agents that silence RhoA in cultured human RhoA expressing cells and in a subject.

Table 1 provides exemplary iRNA agents targeting RhoA

TABLE 1

Exemplary iRNA agents for targeting RhoA mRNA

| Agent number. | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6477 | 288 | 1 | ccggaagaaacuggugauuguug | double | 2 | ggaagaaacuggugauuguuTT | 3 | acaaucaccaguuucuuccTT |
| 6478 | 289 | 4 | cggaagaaacuggugauuguugg | double | 5 | gaagaaacuggugauuguuTT | 6 | aacaaucaccaguuucuucTT |
| 6479 | 290 | 7 | ggaagaaacuggugauuguuggu | double | 8 | aagaaacuggugauuguugTT | 9 | caacaaucaccaguuucuuTT |
| 6480 | 291 | 10 | gaagaaacuggugauuguuggug | double | 11 | agaaacuggugauuguuggTT | 12 | ccaacaaucaccaguuucuTT |
| 6481 | 292 | 13 | aagaaacuggugauuguugguga | double | 14 | gaaacuggugauuguugguTT | 15 | accaacaaucaccaguuucTT |
| 6482 | 293 | 16 | agaaacuggugauuguuggugau | double | 17 | aaacuggugauuguuggugTT | 18 | caccaacaaucaccaguuuTT |
| 6483 | 294 | 19 | gaaacuggugauuguuggugaug | double | 20 | aacuggugauuguugguGaTT | 21 | ucaccaacaaucaccaguuTT |
| 6484 | 295 | 22 | aaacuggugauuguuggugaugg | double | 23 | acuggugauuguuggugauTT | 24 | aucaccaacaaucaccaguTT |
| 6485 | 296 | 25 | aacuggugauuguuggugaugga | double | 26 | cuggugauuguuggugaugTT | 27 | caucaccaacaaucaccagTT |
| 6486 | 297 | 28 | acuggugauuguuggugauggag | double | 29 | uggugauuguuggugauggTT | 30 | ccaucaccaacaaucaccaTT |
| 6487 | 298 | 31 | cuggugauuguuggugauggagc | double | 32 | ggugauuguuggugauggaTT | 33 | uccaucaccaacaaucaccTT |
| 6488 | 299 | 34 | uggugauuguuggugauggagcc | double | 35 | gugauuguuggugauggagTT | 36 | cuccaucaccaacaaucacTT |
| 6489 | 300 | 37 | ggugauuguuggugauggagccu | double | 38 | ugauuguuggugauggagcTT | 39 | gcuccaucaccaacaaucaTT |
| 6490 | 326 | 40 | gaaagacaugcuugcucauaguc | double | 41 | aagacaugcuugcucauagTT | 42 | cuaugagcaagcaugucuuTT |
| 6491 | 327 | 43 | aaagacaugcuugcucauagucu | double | 44 | agacaugcuugcucauaguTT | 45 | acuaugagcaagcaugucuTT |
| 6492 | 328 | 46 | aagacaugcuugcucauagucuu | double | 47 | gacaugcuugcucauagucTT | 48 | gacuaugagcaagcaugucTT |
| 6493 | 329 | 49 | agacaugcuugcucauagucuuc | double | 50 | acaugcuugcucauagucuTT | 51 | agacuaugagcaagcauguTT |
| 6494 | 330 | 52 | gacaugcuugcucauagucuuca | double | 53 | caugcuugcucauagucuuTT | 54 | aagacuaugagcaagcaugTT |
| 6495 | 331 | 55 | acaugcuugcucauagucuucag | double | 56 | augcuugcucauagucuucTT | 57 | gaagacuaugagcaagcauTT |
| 6496 | 332 | 58 | caugcuugcucauagucuucagc | double | 59 | ugcuugcucauagucuucaTT | 60 | ugaagacuaugagcaagcaTT |
| 6497 | 333 | 61 | augcuugcucauagucuucagca | double | 62 | gcuugcucauagucuucagTT | 63 | cugaagacuaugagcaagcTT |
| 6498 | 334 | 64 | ugcuugcucauagucuucagcaa | double | 65 | cuugcucauagucuucagcTT | 66 | gcugaagacuaugagcaagTT |
| 6499 | 335 | 67 | gcuugcucauagucuucagcaag | double | 68 | uugcucauagucuucagcaTT | 69 | ugcugaagacuaugagcaaTT |
| 6500 | 336 | 70 | cuugcucauagucuucagcaagg | double | 71 | ugcucauagucuucagcaaTT | 72 | uugcugaagacuaugagcaTT |
| 6501 | 337 | 73 | uugcucauagucuucagcaagga | double | 74 | gcucauagucuucagcaagTT | 75 | cuugcugaagacuaugagcTT |
| 6502 | 338 | 76 | ugcucauagucuucagcaaggac | double | 77 | cucauagucuucagcaaggTT | 78 | ccuugcugaagacuaugagTT |
| 6503 | 339 | 79 | gcucauagucuucagcaaggacc | double | 80 | ucauagucuucagcaaggaTT | 81 | uccuugcugaagacuaugaTT |
| 6504 | 340 | 82 | cucauagucuucagcaaggacca | double | 83 | cauagucuucagcaaggacTT | 84 | guccuugcugaagacuaugTT |
| 6505 | 341 | 85 | ucauagucuucagcaaggaccag | double | 86 | auagucuucagcaaggaccTT | 87 | gguccuugcugaagacuauTT |
| 6506 | 342 | 88 | cauagucuucagcaaggaccagu | double | 89 | uagucuucagcaaggaccaTT | 90 | ugguccuugcugaagacuaTT |
| 6507 | 343 | 91 | auagucuucagcaaggaccaguu | double | 92 | agucuucagcaaggaccagTT | 93 | cugguccuugcugaagacuTT |
| 6508 | 344 | 94 | uagucuucagcaaggaccaguuc | double | 95 | gucuucagcaaggaccaguTT | 96 | acugguccuugcugaagacTT |
| 6509 | 345 | 97 | agucuucagcaaggaccaguucc | double | 98 | ucuucagcaaggaccaguuTT | 99 | aacugguccuugcugaagaTT |
| 6510 | 346 | 100 | gucuucagcaaggaccaguuccc | double | 101 | cuucagcaaggaccaguucTT | 102 | gaacugguccuugcugaagTT |

TABLE 1-continued

Exemplary iRNA agents for targeting RhoA mRNA

| Agent number. | Start pos. in RNA[b] | SEQ ID NO. | target sequence (5'-3') | duplex design (over- hang)[a] | sense strand SEQ ID NO. | sequence (5'-3') | antisense strand SEQ ID NO. | sequence (5'-3') |
|---|---|---|---|---|---|---|---|---|
| 6511 | 347 | 103 | ucuucagcaaggaccaguuccca | double | 104 | uucagcaaggaccaguuccTT | 105 | ggaacugguccuugcugaaTT |
| 6512 | 348 | 106 | cuucagcaaggaccaguucccag | double | 107 | ucagcaaggaccaguucccTT | 108 | gggaacugguccuugcugaTT |
| 6513 | 349 | 109 | uucagcaaggaccaguucccaga | double | 110 | cagcaaggaccaguucccaTT | 111 | ugggaacugguccuugcugTT |
| 6514 | 350 | 112 | ucagcaaggaccaguucccagag | double | 113 | agcaaggaccaguucccagTT | 114 | cugggaacugguccuugcuTT |
| 6515 | 351 | 115 | cagcaaggaccaguucccagagg | double | 116 | gcaaggaccaguucccagaTT | 117 | ucugggaacugguccuugcTT |
| 6516 | 352 | 118 | agcaaggaccaguucccagaggu | double | 119 | caaggaccaguucccagagTT | 120 | cucugggaacugguccuugTT |
| 6517 | 353 | 121 | gcaaggaccaguucccagaggug | double | 122 | aaggaccaguucccagaggTT | 123 | ccucugggaacugguccuuTT |
| 6518 | 354 | 124 | caaggaccaguucccagaggugu | double | 125 | aggaccaguucccagagguTT | 126 | accucugggaacugguccuTT |
| 6519 | 425 | 127 | gaaagcagguagaguuggcuuug | double | 128 | aagcagguagaguuggcuuTT | 129 | aagccaacucuaccugcuuTT |
| 6520 | 426 | 130 | aaagcagguagaguuggcuugu | double | 131 | agcagguagaguuggcuuuTT | 132 | aaagccaacucuaccugcuTT |
| 6521 | 535 | 133 | gacagcccugauaguuuagaaaa | double | 134 | cagcccugauaguuuagaaTT | 135 | uucuaaacuaucagggcugTT |
| 6522 | 536 | 136 | acagcccugauaguuuagaaaac | double | 137 | agcccugauaguuuagaaaTT | 138 | uuucuaaacuaucagggcuTT |
| 6523 | 537 | 139 | cagcccugauaguuuagaaaaca | double | 140 | gcccugauaguuuagaaaaTT | 141 | uuuucuaaacuaucagggcTT |
| 6524 | 538 | 142 | agcccugauaguuuagaaaacau | double | 143 | cccugauaguuuagaaaacTT | 144 | guuuucuaaacuaucagggTT |
| 6525 | 539 | 145 | gcccugauaguuuagaaaacauc | double | 146 | ccugauaguuuagaaaacaTT | 147 | uguuuucuaaacuaucaggTT |
| 6526 | 540 | 148 | cccugauaguuuagaaaacaucc | double | 149 | cugauaguuuagaaaacauTT | 150 | auguuuucuaaacuaucagTT |
| 6527 | 541 | 151 | ccugauaguuuagaaaacauccc | double | 152 | ugauaguuuagaaaacaucTT | 153 | gauguuuucuaaacuaucaTT |
| 6528 | 542 | 154 | cugauaguuuagaaaacauccca | double | 155 | gauaguuuagaaaacauccTT | 156 | ggauguuuucuaaacuaucTT |
| 6529 | 543 | 157 | ugauaguuuagaaaacaucccag | double | 158 | auaguuuagaaaacaucccTT | 159 | gggauguuuucuaaacuauTT |
| 6530 | 544 | 160 | gauaguuuagaaaacaucccaga | double | 161 | uaguuuagaaaacaucccaTT | 162 | ugggauguuuucuaaacuaTT |
| 6531 | 545 | 163 | auaguuuagaaaacaucccagaa | double | 164 | aguuuagaaaacaucccagTT | 165 | cugggauguuuucuaaacuTT |
| 6532 | 546 | 166 | uaguuuagaaaacaucccagaaa | double | 167 | guuuagaaaacaucccagaTT | 168 | ucugggauguuuucuaaacTT |
| 6533 | 547 | 169 | aguuuagaaaacaucccagaaaa | double | 170 | uuuagaaaacaucccagaaTT | 171 | uucugggauguuuucuaaaTT |
| 6534 | 548 | 172 | guuuagaaaacaucccagaaaag | double | 173 | uuagaaaacaucccagaaaTT | 174 | uuucugggauguuuucuaaTT |
| 6535 | 549 | 175 | uuuagaaaacaucccagaaaagu | double | 176 | uagaaaacaucccagaaaaTT | 177 | uuuucugggauguuuucuaTT |
| 6536 | 575 | 178 | ccccagaagucaagcauuucugu | double | 179 | ccagaagucaagcauuucuTT | 180 | agaaaugcuugacuucggTT |
| 6537 | 576 | 181 | cccagaagucaagcauuucuguc | double | 182 | cagaagucaagcauuucugTT | 183 | cagaaaugcuugacuucgTT |
| 6538 | 577 | 184 | ccagaagucaagcauuucugucc | double | 185 | agaagucaagcauuucuguTT | 186 | acagaaaugcuugacuucuTT |
| 6539 | 578 | 187 | cagaagucaagcauuucugucc | double | 188 | gaagucaagcauuucugucTT | 189 | gacagaaaugcuugacuucTT |
| 6540 | 579 | 190 | agaagucaagcauuucugucca | double | 191 | aagucaagcauuucuguccTT | 192 | ggacagaaaugcuugacuuTT |
| 6541 | 692 | 193 | ugaaaccugaagaaggcagagau | double | 194 | aaaccugaagaaggcagagTT | 195 | cucugccuucuucagguuuTT |
| 6542 | 693 | 196 | gaaaccugaagaaggcagagaua | double | 197 | aaccugaagaaggcagagaTT | 198 | ucucugccuucuucagguuTT |
| 6543 | 694 | 199 | aaaccugaagaaggcagagauau | double | 200 | accugaagaaggcagagauTT | 201 | aucucugccuucuucagguTT |
| 6544 | 695 | 202 | aaccugaagaaggcagagauaug | double | 203 | ccugaagaaggcagagauaTT | 204 | uaucucugccuucuucaggTT |
| 6545 | 696 | 205 | accugaagaaggcagagauaugg | double | 206 | cugaagaaggcagagauauTT | 207 | auaucucugccuucuucagTT |

TABLE 1-continued

Exemplary iRNA agents for targeting RhoA mRNA

| Agent number. | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6546 | 697 | 208 | ccugaagaaggcagagauauggc | double | 209 | ugaagaaggcagagauaugTT | 210 | cauaucucugccuucuucaTT |
| 6547 | 698 | 211 | cugaagaaggcagagauauggca | double | 212 | gaagaaggcagagauauggTT | 213 | ccauaucucugccuucuucTT |
| 6548 | 699 | 214 | ugaagaaggcagagauauggcaa | double | 215 | aagaaggcagagauauggcTT | 216 | gccauaucucugccuucuuTT |
| 6549 | 700 | 217 | gaagaaggcagagauauggcaaa | double | 218 | agaaggcagagauauggcaTT | 219 | ugccauaucucugccuucuTT |
| 6550 | 701 | 220 | aagaaggcagagauauggcaaac | double | 221 | gaaggcagagauauggcaaTT | 222 | uugccauaucucugccuucTT |
| 6551 | 702 | 223 | agaaggcagagauauggcaaaca | double | 224 | aaggcagagauauggcaaaTT | 225 | uuugccauaucucugccuuTT |
| 6552 | 703 | 226 | gaaggcagagauauggcaaacag | double | 227 | aggcagagauauggcaaacTT | 228 | guuugccauaucucugccuTT |
| 6553 | 704 | 229 | aaggcagagauauggcaaacagg | double | 230 | ggcagagauauggcaaacaTT | 231 | uguuugccauaucucugccTT |
| 6554 | 705 | 232 | aggcagagauauggcaaacagga | double | 233 | gcagagauauggcaaacagTT | 234 | cuguuugccauaucucugcTT |
| 6555 | 706 | 235 | ggcagagauauggcaaacaggau | double | 236 | cagagauauggcaaacaggTT | 237 | ccuguuugccauaucucugTT |
| 6556 | 707 | 238 | gcagagauauggcaaacaggauu | double | 239 | agagauauggcaaacaggaTT | 240 | uccuguuugccauaucucuTT |
| 6557 | 708 | 241 | cagagauauggcaaacaggauug | double | 242 | gagauauggcaaacaggauTT | 243 | auccuguuugccauaucucTT |
| 6558 | 709 | 244 | agagauauggcaaacaggauugg | double | 245 | agauauggcaaacaggauuTT | 246 | aauccuguuugccauaucuTT |
| 6559 | 710 | 247 | gagauauggcaaacaggauuggc | double | 248 | gauauggcaaacaggauugTT | 249 | caauccuguuugccauaucTT |
| 6560 | 711 | 250 | agauauggcaaacaggauuggcg | double | 251 | auauggcaaacaggauuggTT | 252 | ccaauccuguuugccauauTT |
| 6561 | 712 | 253 | gauauggcaaacaggauuggcgc | double | 254 | uauggcaaacaggauuggcTT | 255 | gccaauccuguuugccauaTT |
| 6562 | 713 | 256 | auauggcaaacaggauuggcgcu | double | 257 | auggcaaacaggauuggcgTT | 258 | cgccaauccuguuugccauTT |
| 6563 | 714 | 259 | uauggcaaacaggauuggcgcuu | double | 260 | uggcaaacaggauuggcgcTT | 261 | gcgccaauccuguuugccaTT |
| 6564 | 715 | 262 | auggcaaacaggauuggcgcuuu | double | 263 | ggcaaacaggauuggcgcuTT | 264 | agcgccaauccuguuugccTT |
| 6565 | 716 | 265 | uggcaaacaggauuggcgcuuuu | double | 266 | gcaaacaggauuggcgcuuTT | 267 | aagcgccaauccuguuugcTT |
| 6566 | 717 | 268 | ggcaaacaggauuggcgcuuuug | double | 269 | caaacaggauuggcgcuuuTT | 270 | aaagcgccaauccuguuugTT |
| 6567 | 718 | 271 | gcaaacaggauuggcgcuuuugg | double | 272 | aaacaggauuggcgcuuuuTT | 273 | aaaagcgccaauccuguuuTT |
| 6568 | 719 | 274 | caaacaggauuggcgcuuuuggg | double | 275 | aacaggauuggcgcuuuugTT | 276 | caaaagcgccaauccuguuTT |
| 6569 | 720 | 277 | aaacaggauuggcgcuuuugggu | double | 278 | acaggauuggcgcuuuuggTT | 279 | ccaaaagcgccaauccuguTT |
| 6570 | 721 | 280 | aacaggauuggcgcuuuugggua | double | 281 | caggauuggcgcuuuugggTT | 282 | cccaaaagcgccaauccugTT |
| 6571 | 722 | 283 | acaggauuggcgcuuuuggguac | double | 284 | aggauuggcgcuuuuggguTT | 285 | acccaaaagcgccaauccuTT |
| 6572 | 723 | 286 | caggauuggcgcuuuuggguaca | double | 287 | ggauuggcgcuuuuggguaTT | 288 | uacccaaaagcgccaauccTT |
| 6573 | 724 | 289 | aggauuggcgcuuuuggguacau | double | 290 | gauuggcgcuuuuggguacTT | 291 | guacccaaaagcgccaaucTT |
| 6574 | 725 | 292 | ggauuggcgcuuuuggguacaug | double | 293 | auuggcgcuuuuggguacaTT | 294 | uguacccaaaagcgccaauTT |
| 6575 | 726 | 295 | gauuggcgcuuuuggguacaugg | double | 296 | uuggcgcuuuuggguacauTT | 297 | auguacccaaaagcgccaaTT |
| 6576 | 727 | 298 | auuggcgcuuuuggguacaugga | double | 299 | uggcgcuuuuggguacaugTT | 300 | cauguacccaaaagcgccaTT |
| 6577 | 728 | 301 | uuggcgcuuuuggguacauggag | double | 302 | ggcgcuuuuggguacauggTT | 303 | ccauguacccaaaagcgccTT |
| 6578 | 729 | 304 | uggcgcuuuuggguacauggagu | double | 305 | gcgcuuuuggguacauggaTT | 306 | uccauguacccaaaagcgcTT |
| 6579 | 730 | 307 | ggcgcuuuuggguacauggagug | double | 308 | cgcuuuuggguacauggagTT | 309 | cuccauguacccaaaagcgTT |
| 6580 | 731 | 310 | gcgcuuuuggguacauggagugu | double | 311 | gcuuuuggguacauggaguTT | 312 | acuccauguacccaaaagcTT |

TABLE 1-continued

Exemplary iRNA agents for targeting RhoA mRNA

| Agent number. | Start pos. in RNA[b] | SEQ ID NO. | target sequence (5'-3') | duplex design (overhang)[a] | sense strand SEQ ID NO. | sequence (5'-3') | antisense strand SEQ ID NO. | sequence (5'-3') |
|---|---|---|---|---|---|---|---|---|
| 6581 | 732 | 313 | cgcuuuuggguacauggaguguu | double | 314 | cuuuuggguacauggaguguTT | 315 | cacuccauguacccaaaagTT |
| 6582 | 733 | 316 | gcuuuuggguacauggaguguuc | double | 317 | uuuuggguacauggaguguuTT | 318 | acacuccauguacccaaaaTT |
| 6583 | 734 | 319 | cuuuuggguacauggaguguuca | double | 320 | uuuggguacauggaguguucaTT | 321 | aacacuccauguacccaaaTT |
| 6584 | 735 | 322 | uuuuggguacauggaguguucag | double | 323 | uuggguacauggaguguucagTT | 324 | gaacacuccauguacccaaTT |
| 6585 | 736 | 325 | uuuggguacauggaguguucagc | double | 326 | uggguacauggaguguucagcTT | 327 | ugaacacuccauguacccTT |
| 6586 | 737 | 328 | uuggguacauggaguguucagca | double | 329 | ggguacauggaguguucagcaTT | 330 | cugaacacuccauguacccTT |
| 6587 | 738 | 331 | uggguacauggaguguucagcaa | double | 332 | gguacauggaguguucagcTT | 333 | gcugaacacuccauguaccTT |
| 6588 | 739 | 334 | ggguacauggaguguucagcaaa | double | 335 | guacauggaguguucagcaTT | 336 | ugcugaacacuccauguacTT |
| 6589 | 740 | 337 | gguacauggaguguucagcaaag | double | 338 | uacauggaguguucagcaaTT | 339 | uugcugaacacuccauguaTT |
| 6590 | 741 | 340 | guacauggaguguucagcaaaga | double | 341 | acauggaguguucagcaaaTT | 342 | uuugcugaacacuccauguTT |
| 6591 | 742 | 343 | uacauggaguguucagcaaagac | double | 344 | cauggaguguucagcaaagTT | 345 | cuuugcugaacacuccaugTT |
| 6592 | 743 | 346 | acauggaguguucagcaaagacc | double | 347 | auggaguguucagcaaagaTT | 348 | ucuuugcugaacacuccauTT |
| 6593 | 744 | 349 | cauggaguguucagcaaagacca | double | 350 | uggaguguucagcaaagacTT | 351 | gucuuugcugaacacuccaTT |
| 6594 | 745 | 352 | auggaguguucagcaaagaccaa | double | 353 | ggaguguucagcaaagaccTT | 354 | ggucuuugcugaacacuccTT |
| 6595 | 746 | 355 | uggaguguucagcaaagaccaaa | double | 356 | gaguguucagcaaagaccaTT | 357 | uggucuuugcugaacacucTT |
| 6596 | 747 | 358 | ggaguguucagcaaagaccaaag | double | 359 | aguguucagcaaagaccaaTT | 360 | uuggucuuugcugaacacuTT |
| 6597 | 748 | 361 | gaguguucagcaaagaccaaaga | double | 362 | guguucagcaaagaccaaaTT | 363 | uuuggucuuugcugaacacTT |
| 6598 | 749 | 364 | aguguucagcaaagaccaaagau | double | 365 | uguucagcaaagaccaaagTT | 366 | cuuuggucuuugcugaacaTT |
| 6599 | 750 | 367 | guguucagcaaagaccaaagaug | double | 368 | guucagcaaagaccaaagaTT | 369 | ucuuuggucuuugcugaacTT |
| 6600 | 770 | 370 | auggagugagagagguuuugaa | double | 371 | ggagugagagagguuuugTT | 372 | caaaaaccucucucacuccTT |
| 6601 | 771 | 373 | uggagugagagagguuuugaaa | double | 374 | gagugagagagguuuugaTT | 375 | ucaaaaccucucucacucTT |
| 6602 | 797 | 376 | cuacgagagcugcucugcaagcu | double | 377 | acgagagcugcucugcaagTT | 378 | cuugcagagcagcucucguTT |
| 6603 | 798 | 379 | uacgagagcugcucugcaagcua | double | 380 | cgagagcugcucugcaagcTT | 381 | gcuugcagagcagcucucgTT |
| 6604 | 799 | 382 | acgagagcugcucugcaagcuag | double | 383 | gagagcugcucugcaagcuTT | 384 | agcuugcagagcagcucucTT |
| 6605 | 800 | 385 | cgagagcugcucugcaagcuaga | double | 386 | agagcugcucugcaagcuaTT | 387 | uagcuugcagagcagcucuTT |
| 6606 | 801 | 388 | gagagcugcucugcaagcuagac | double | 389 | gagcugcucugcaagcuagTT | 390 | cuagcuugcagagcagcucTT |
| 6607 | 802 | 391 | agagcugcucugcaagcuagacg | double | 392 | agcugcucugcaagcuagaTT | 393 | ucuagcuugcagagcagcuTT |
| 6608 | 803 | 394 | gagcugcucugcaagcuagacgu | double | 395 | gcugcucugcaagcuagacTT | 396 | gucuagcuugcagagcagcTT |
| 6609 | 804 | 397 | agcugcucugcaagcuagacgug | double | 398 | cugcucugcaagcuagacgTT | 399 | cgucuagcuugcagagcagTT |
| 6610 | 895 | 400 | uugaagugcuguuuauuaaucuu | double | 401 | gaagugcuguuuauuaaucTT | 402 | gauuaauaaacagcacuucTT |
| 6611 | 896 | 403 | ugaagugcuguuuauuaaucuua | double | 404 | aagugcuguuuauuaaucuTT | 405 | agauuaauaaacagcacuuTT |
| 6612 | 897 | 406 | gaagugcuguuuauuaaucuuag | double | 407 | agugcuguuuauuaaucuuTT | 408 | aagauuaauaaacagcacuTT |
| 6613 | 898 | 409 | aagugcuguuuauuaaucuuagu | double | 410 | gugcuguuuauuaaucuuaTT | 411 | uaagauuaauaaacagcacTT |
| 6614 | 899 | 412 | agugcuguuuauuaaucuuagug | double | 413 | ugcuguuuauuaaucuuagTT | 414 | cuaagauuaauaaacagcaTT |
| 6615 | 900 | 415 | gugcuguuuauuaaucuuagugu | double | 416 | gcuguuuauuaaucuuaguTT | 417 | acuaagauuaauaaacagcTT |

TABLE 1-continued

Exemplary iRNA agents for targeting RhoA mRNA

| Agent number | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6616 | 901 | 418 | ugcuguuuauuaaucuuagugua | double | 419 | cuguuuauuaaucuuagugu TT | 420 | cacuaagauuaauaaacag TT |
| 6617 | 902 | 421 | gcuguuuauuaaucuuaguguau | double | 422 | uguuuauuaaucuuaguguTT | 423 | acacuaagauuaauaaacaTT |
| 6618 | 903 | 424 | cuguuuauuaaucuuaguguaug | double | 425 | guuuauuaaucuuaguguaTT | 426 | uacacuaagauuaauaaacTT |
| 6619 | 904 | 427 | uguuuauuaaucuuaguguauga | double | 428 | uuuauuaaucuuaguguauTT | 429 | auacacuaagauuaauaaaTT |
| 6620 | 905 | 430 | guuuauuaaucuuaguguaugau | double | 431 | uuauuaaucuuaguguaugTT | 432 | cauacacuaagauuaauaaTT |
| 6621 | 906 | 433 | uuuauuaaucuuaguguaugauu | double | 434 | uauuaaucuuaguguaugaTT | 435 | ucauacacuaagauuaauaTT |
| 6622 | 907 | 436 | uuauuaaucuuaguguaugauua | double | 437 | auuaaucuuaguguaugauTT | 438 | aucauacacuaagauuaauTT |
| 6623 | 908 | 439 | uauuaaucuuaguguaugauuac | double | 440 | uuaaucuuaguguaugauuTT | 441 | aaucauacacuaagauuaaTT |
| 6624 | 909 | 442 | auuaaucuuaguguaugauuacu | double | 443 | uaaucuuaguguaugauuaTT | 444 | uaaucauacacuaagauuaTT |
| 6625 | 910 | 445 | uuaaucuuaguguaugauuacug | double | 446 | aaucuuaguguaugauuacTT | 447 | guaaucauacacuaagauuTT |
| 6626 | 911 | 448 | uaaucuuaguguaugauuacugg | double | 449 | aucuuaguguaugauuacuTT | 450 | aguaaucauacacuaagauTT |
| 6627 | 912 | 451 | aaucuuaguguaugauuacuggc | double | 452 | ucuuaguguaugauuacugTT | 453 | caguaaucauacacuaagaTT |
| 6628 | 913 | 454 | aucuuaguguaugauuacuggcc | double | 455 | cuuaguguaugauuacuggTT | 456 | ccaguaaucauacacuaagTT |
| 6629 | 914 | 457 | ucuuaguguaugauuacuggccu | double | 458 | uuaguguaugauuacuggcTT | 459 | gccaguaaucauacacuaaTT |
| 6630 | 915 | 460 | cuuaguguaugauuacuggccuu | double | 461 | uaguguaugauuacuggccTT | 462 | ggccaguaaucauacacuaTT |
| 6631 | 916 | 463 | uuaguguaugauuacuggccuuu | double | 464 | aguguaugauuacuggccuTT | 465 | aggccaguaaucauacacuTT |
| 6632 | 917 | 466 | uaguguaugauuacuggccuuuu | double | 467 | guguaugauuacuggccuuTT | 468 | aaggccaguaaucauacacTT |
| 6633 | 918 | 469 | aguguaugauuacuggccuuuuu | double | 470 | uguaugauuacuggccuuuTT | 471 | aaaggccaguaaucauacaTT |
| 6634 | 919 | 472 | guguaugauuacuggccuuuuuc | double | 473 | guaugauuacuggccuuuuTT | 474 | aaaaggccaguaaucauacTT |
| 6635 | 939 | 475 | uucauuuaucuauaauuuaccua | double | 476 | cauuuaucuauaauuuaccTT | 477 | gguaaauuauagauaaaugTT |
| 6636 | 940 | 478 | ucauuuaucuauaauuuaccuaa | double | 479 | auuuaucuauaauuuaccuTT | 480 | agguaaauuauagauaaauTT |
| 6637 | 941 | 481 | cauuuaucuauaauuuaccuaag | double | 482 | uuuaucuauaauuuaccuaTT | 483 | uagguaaauuauagauaaaTT |
| 6638 | 942 | 484 | auuuaucuauaauuuaccuaaga | double | 485 | uuaucuauaauuuaccuaaTT | 486 | uuagguaaauuauagauaaTT |
| 6639 | 943 | 487 | uuuaucuauaauuuaccuaagau | double | 488 | uaucuauaauuuaccuaagTT | 489 | cuuagguaaauuauagauaTT |
| 6640 | 944 | 490 | uuaucuauaauuuaccuaagauu | double | 491 | aucuauaauuuaccuaagaTT | 492 | ucuuagguaaauuauagauTT |
| 6641 | 945 | 493 | uaucuauaauuuaccuaagauua | double | 494 | ucuauaauuuaccuaagauTT | 495 | aucuuagguaaauuauagaTT |
| 6642 | 946 | 496 | aucuauaauuuaccuaagauuac | double | 497 | cuauaauuuaccuaagauuTT | 498 | aaucuuagguaaauuauagTT |
| 6643 | 947 | 499 | ucuauaauuuaccuaagauuaca | double | 500 | uauaauuuaccuaagauuaTT | 501 | uaaucuuagguaaauuauaTT |
| 6644 | 948 | 502 | cuauaauuuaccuaagauuacaa | double | 503 | auaauuuaccuaagauuacTT | 504 | guaaucuuagguaaauuauTT |
| 6645 | 949 | 505 | uauaauuuaccuaagauuacaaa | double | 506 | uaauuuaccuaagauuacaTT | 507 | uguaaucuuagguaaauuaTT |
| 6646 | 950 | 508 | auaauuuaccuaagauuacaaau | double | 509 | aauuuaccuaagauuacaaTT | 510 | uuguaaucuuagguaaauuTT |
| 6647 | 951 | 511 | uaauuuaccuaagauuacaaauc | double | 512 | auuuaccuaagauuacaaaTT | 513 | uuuguaaucuuagguaaauTT |
| 6648 | 952 | 514 | aauuuaccuaagauuacaaauca | double | 515 | uuuaccuaagauuacaaauTT | 516 | auuuguaaucuuagguaaaTT |
| 6649 | 953 | 517 | auuuaccuaagauuacaaaucag | double | 518 | uuaccuaagauuacaaaucTT | 519 | gauuuguaaucuuagguaaTT |
| 6650 | 954 | 520 | uuuaccuaagauuacaaaucaga | double | 521 | uaccuaagauuacaaaucaTT | 522 | ugauuuguaaucuuaggua TT |

TABLE 1-continued

Exemplary iRNA agents for targeting RhoA mRNA

| Agent number. | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6651 | 974 | 523 | agaagucaucuugcuaccaguau | double | 524 | aagucaucuugcuaccaguTT | 525 | acugguagcaagaugacuuTT |
| 6652 | 975 | 526 | gaagucaucuugcuaccaguauu | double | 527 | agucaucuugcuaccaguaTT | 528 | uacugguagcaagaugacuTT |
| 6653 | 976 | 529 | aagucaucuugcuaccaguauuu | double | 530 | gucaucuugcuaccaguauTT | 531 | auacugguagcaagaugacTT |
| 6654 | 977 | 532 | agucaucuugcuaccaguauuua | double | 533 | ucaucuugcuaccaguauuTT | 534 | aauacugguagcaagaugaTT |
| 6655 | 978 | 535 | gucaucuugcuaccaguauuuag | double | 536 | caucuugcuaccaguauuuTT | 537 | aaauacugguagcaagaugTT |
| 6656 | 979 | 538 | ucaucuugcuaccaguauuuaga | double | 539 | aucuugcuaccaguauuuaTT | 540 | uaaauacugguagcaagauTT |
| 6657 | 980 | 541 | caucuugcuaccaguauuuagaa | double | 542 | ucuugcuaccaguauuuagTT | 543 | cuaaauacugguagcaagaTT |
| 6658 | 981 | 544 | aucuugcuaccaguauuuagaag | double | 545 | cuugcuaccaguauuuagaTT | 546 | ucuaaauacugguagcaagTT |
| 6659 | 982 | 547 | ucuugcuaccaguauuuagaagc | double | 548 | uugcuaccaguauuuagaaTT | 549 | uucuaaauacugguagcaaTT |
| 6660 | 983 | 550 | cuugcuaccaguauuuagaagcc | double | 551 | ugcuaccaguauuuagaagTT | 552 | cuucuaaauacugguagcaTT |
| 6661 | 984 | 553 | uugcuaccaguauuuagaagcca | double | 554 | gcuaccaguauuuagaagcTT | 555 | gcuucuaaauacugguagcTT |
| 6662 | 985 | 556 | ugcuaccaguauuuagaagccaa | double | 557 | cuaccaguauuuagaagccTT | 558 | ggcuucuaaauacugguagTT |
| 6663 | 986 | 559 | gcuaccaguauuuagaagccaac | double | 560 | uaccaguauuuagaagccaTT | 561 | uggcuucuaaauacugguaTT |
| 6664 | 987 | 562 | cuaccaguauuuagaagccaacu | double | 563 | accaguauuuagaagccaaTT | 564 | uuggcuucuaaauacugguTT |
| 6665 | 988 | 565 | uaccaguauuuagaagccaacua | double | 566 | ccaguauuuagaagccaacTT | 567 | guuggcuucuaaauacuggTT |
| 6666 | 1131 | 568 | cuugcuucuuucuagaaagagaa | double | 569 | ugcuucuuucuagaaagagTT | 570 | cucuuucuagaaagaagcaTT |
| 6667 | 1132 | 571 | uugcuucuuucuagaaagagaaa | double | 572 | gcuucuuucuagaaagagaTT | 573 | ucuuucuagaaagaagcTT |
| 6668 | 1133 | 574 | ugcuucuuucuagaaagagaaac | double | 575 | cuucuuucuagaaagagaaTT | 576 | uucucuuucuagaaagaagTT |
| 6669 | 1134 | 577 | gcuucuuucuagaaagagaaaca | double | 578 | uucuuucuagaaagagaaaTT | 579 | uuucuuucuagaaagaaTT |
| 6670 | 1135 | 580 | cuucuuucuagaaagagaaacag | double | 581 | ucuuucuagaaagagaaacTT | 582 | guuucucuuucuagaaagaTT |
| 6671 | 1136 | 583 | uucuuucuagaaagagaaacagu | double | 584 | cuuucuagaaagagaaacaTT | 585 | uguuucucuuucuagaaagTT |
| 6672 | 1137 | 586 | ucuuucuagaaagagaaacaguu | double | 587 | uuucuagaaagagaaacagTT | 588 | cuguuucucuuucuagaaaTT |
| 6673 | 1138 | 589 | cuuucuagaaagagaaacaguug | double | 590 | uucuagaaagagaaacaguTT | 591 | acuguuucucuuucuagaaTT |
| 6674 | 1139 | 592 | uuucuagaaagagaaacaguugg | double | 593 | ucuagaaagagaaacaguuTT | 594 | aacuguuucucuuucuagaTT |
| 6675 | 1140 | 595 | uucuagaaagagaaacaguuggu | double | 596 | cuagaaagagaaacaguugTT | 597 | caacuguuucucuuucuagTT |
| 6676 | 1141 | 598 | ucuagaaagagaaacaguuggua | double | 599 | uagaaagagaaacaguuggTT | 600 | ccaacuguuucucuuucuaTT |
| 6677 | 1142 | 601 | cuagaaagagaaacaguugguaa | double | 602 | agaaagagaaacaguugguTT | 603 | accaacuguuucucuuucuTT |
| 6678 | 1143 | 604 | uagaaagagaaacaguugguaac | double | 605 | gaaagagaaacaguugguaTT | 606 | uaccaacuguuucucuuucTT |
| 6679 | 1144 | 607 | agaaagagaaacaguugguaacu | double | 608 | aaagagaaacaguugguaaTT | 609 | uuaccaacuguuucucuuuTT |
| 6680 | 1145 | 610 | gaaagagaaacaguugguaacuu | double | 611 | aagagaaacaguugguaacTT | 612 | guuaccaacuguuucucuuTT |
| 6681 | 1146 | 613 | aaagagaaacaguugguaacuuu | double | 614 | agagaaacaguugguaacuTT | 615 | aguuaccaacuguuucucuTT |
| 6682 | 1147 | 616 | aagagaaacaguugguaacuuuu | double | 617 | gagaaacaguugguaacuuTT | 618 | aaguuaccaacuguuucucTT |
| 6683 | 1148 | 619 | agagaaacaguugguaacuuuug | double | 620 | agaaacaguugguaacuuuTT | 621 | aaaguuaccaacuguuucuTT |
| 6684 | 1149 | 622 | gagaaacaguugguaacuuuugu | double | 623 | gaaacaguugguaacuuuuTT | 624 | aaaaguuaccaacuguuucTT |
| 6685 | 1150 | 625 | agaaacaguugguaacuuuugug | double | 626 | aaacaguugguaacuuuugTT | 627 | caaaaguuaccaacuguuuTT |

TABLE 1-continued

Exemplary iRNA agents for targeting RhoA mRNA

| Agent number | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6686 | 1151 | 628 | gaaacaguugguaacuuuuguga | double | 629 | aacaguugguaacuuuugugTT | 630 | acaaaaguuaccaacuguTT |
| 6687 | 1152 | 631 | aaacaguugguaacuuuugugaa | double | 632 | acaguugguaacuuuugugTT | 633 | cacaaaaguuaccaacuguTT |
| 6688 | 1153 | 634 | aacaguugguaacuuuugugaau | double | 635 | caguugguaacuuuugugaTT | 636 | ucacaaaaguuaccaacugTT |
| 6689 | 1154 | 637 | acaguugguaacuuuugugaauu | double | 638 | aguugguaacuuuugugaaTT | 639 | uucacaaaaguuaccaacuTT |
| 6690 | 1155 | 640 | caguugguaacuuuugugaauua | double | 641 | guugguaacuuuugugaauTT | 642 | auucacaaaaguuaccaacTT |
| 6691 | 1156 | 643 | aguugguaacuuuugugaauuag | double | 644 | uugguaacuuuugugaauuTT | 645 | aauucacaaaaguuaccaaTT |
| 6692 | 1157 | 646 | guugguaacuuuugugaauuagg | double | 647 | ugguaacuuuugugaauuaTT | 648 | uaauucacaaaaguuaccaTT |
| 6693 | 1158 | 649 | uugguaacuuuugugaauuaggc | double | 650 | gguaacuuuugugaauuagTT | 651 | cuaauucacaaaaguuaccTT |
| 6694 | 1159 | 652 | ugguaacuuuugugaauuaggcu | double | 653 | guaacuuuugugaauuaggTT | 654 | ccuaauucacaaaaguuacTT |
| 6695 | 1160 | 655 | gguaacuuuugugaauuaggcug | double | 656 | uaacuuuugugaauuaggcTT | 657 | gccuaauucacaaaaguuaTT |
| 6696 | 1161 | 658 | guaacuuuugugaauuaggcugu | double | 659 | aacuuuugugaauuaggcuTT | 660 | agccuaauucacaaaaguuTT |
| 6697 | 1162 | 661 | uaacuuuugugaauuaggcugua | double | 662 | acuuuugugaauuaggcugTT | 663 | cagccuaauucacaaaaguTT |
| 6698 | 1163 | 664 | aacuuuugugaauuaggcuguaa | double | 665 | cuuuugugaauuaggcuguTT | 666 | acagccuaauucacaaaagTT |
| 6699 | 1164 | 667 | acuuuugugaauuaggcuguaac | double | 668 | uuuugugaauuaggcuguaTT | 669 | uacagccuaauucacaaaaTT |
| 6700 | 1165 | 670 | cuuuugugaauuaggcuguaacu | double | 671 | uuugugaauuaggcuguaaTT | 672 | uuacagccuaauucacaaaTT |
| 6701 | 1166 | 673 | uuuugugaauuaggcuguaacua | double | 674 | uugugaauuaggcuguaacTT | 675 | guuacagccuaauucacaaTT |
| 6702 | 1167 | 676 | uuugugaauuaggcuguaacuac | double | 677 | ugugaauuaggcuguaacuTT | 678 | aguuacagccuaauucacaTT |
| 6703 | 1168 | 679 | uugugaauuaggcuguaacuacu | double | 680 | gugaauuaggcuguaacuaTT | 681 | uaguuacagccuaauucacTT |
| 6704 | 1169 | 682 | ugugaauuaggcuguaacuacuu | double | 683 | ugaauuaggcuguaacuacTT | 684 | guaguuacagccuaauucaTT |
| 6705 | 1170 | 685 | gugaauuaggcuguaacuacuuu | double | 686 | gaauuaggcuguaacuacuTT | 687 | aguaguuacagccuaauucTT |
| 6706 | 1171 | 688 | ugaauuaggcuguaacuacuuua | double | 689 | aauuaggcuguaacuacuuTT | 690 | aaguaguuacagccuaauuTT |
| 6707 | 1172 | 691 | gaauuaggcuguaacuacuuuau | double | 692 | auuaggcuguaacuacuuuTT | 693 | aaaguaguuacagccuaauTT |
| 6708 | 1173 | 694 | aauuaggcuguaacuacuuuaua | double | 695 | uuaggcuguaacuacuuuaTT | 696 | uaaaguaguuacagccuaaTT |
| 6709 | 1174 | 697 | auuaggcuguaacuacuuuauaa | double | 698 | uaggcuguaacuacuuuauTT | 699 | auaaaguaguuacagccuaTT |
| 6710 | 1175 | 700 | uuaggcuguaacuacuuuauaac | double | 701 | aggcuguaacuacuuuauaTT | 702 | uauaaaguaguuacagccuTT |
| 6711 | 1176 | 703 | uaggcuguaacuacuuuauaacu | double | 704 | ggcuguaacuacuuuauaaTT | 705 | uucuaaaguaguuacagccTT |
| 6712 | 1177 | 706 | aggcuguaacuacuuuauaacua | double | 707 | gcuguaacuacuuuauaacTT | 708 | guuauaaaguaguuccagcTT |
| 6713 | 1178 | 709 | ggcuguaacuacuuuauaacuaa | double | 710 | cuguaacuacuuuauaacuTT | 711 | aguuauacaguaguuacagTT |
| 6714 | 1179 | 712 | gcuguaacuacuuuauaacuaac | double | 713 | uguaacuacuuuauaacuaTT | 714 | uaguuauaaaguaguuacaTT |
| 6715 | 1180 | 715 | cuguaacuacuuuauaacuaaca | double | 716 | guaacuacuuuauaacuaaTT | 717 | uuaguuauaaaguaguuacTT |
| 6716 | 1181 | 718 | uguaacuacuuuauaacuaacau | double | 719 | uaacuacuuuauaacuaacTT | 720 | guuaguuauaaaguaguuaTT |
| 6717 | 1182 | 721 | guaacuacuuuauaacuaacaug | double | 722 | aacuacuuuauaacuaacaTT | 723 | uguuaguuauaaaguaguuTT |
| 6718 | 1183 | 724 | uaacuacuuuauaacuaacaugu | double | 725 | acuacuuuauaacuaacauTT | 726 | auguuaguuauaaaguaguTT |
| 6719 | 1184 | 727 | aacuacuuuauaacuaacauguc | double | 728 | cuacuuuauaacuaacaugTT | 729 | cauguuaguuauaaaguagTT |
| 6720 | 1185 | 730 | acuacuuuauaacuaacaugucc | double | 731 | uacuuuauaacuaacauguTT | 732 | acauguuaguuauaaaguaTT |

TABLE 1-continued

Exemplary iRNA agents for targeting RhoA mRNA

| Agent number. | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6721 | 1186 | 733 | cuacuuuauaacuaacauguccu | double | 734 | acuuuauaacuaacaugucTT | 735 | gacauguuaguuauaaaguTT |
| 6722 | 1187 | 736 | uacuuuauaacuaacauguccug | double | 737 | cuuuauaacuaacauguccTT | 738 | ggacauguuaguuauaaagTT |
| 6723 | 1188 | 739 | acuuuauaacuaacauguccugc | double | 740 | uuuauaacuaacauguccuTT | 741 | aggacauguuaguuauaaaTT |
| 6724 | 1189 | 742 | cuuuauaacuaacauguccugcc | double | 743 | uuauaacuaacauguccugTT | 744 | caggacauguuaguuauaaTT |
| 6725 | 1190 | 745 | uuuauaacuaacauguccugcc | double | 746 | uauaacuaacauguccugcTT | 747 | gcaggacauguuaguuauaTT |
| 6726 | 1191 | 748 | uuauaacuaacauguccugcca | double | 749 | auaacuaacauguccugccTT | 750 | ggcaggacauguuaguuauTT |
| 6727 | 1192 | 751 | uauaacuaacauguccugccau | double | 752 | uaacuaacauguccugccuTT | 753 | aggcaggacauguuaguuaTT |
| 6728 | 1193 | 754 | auaacuaacauguccugccauu | double | 755 | aacuaacauguccugccuaTT | 756 | uaggcaggacauguuaguuTT |
| 6729 | 1352 | 757 | uggcagaguuacaguucugugu | double | 758 | gcagaguuacaguucugugTT | 759 | cacagaacuguaacucugcTT |
| 6730 | 1353 | 760 | ggcagaguuacaguucuguggu | double | 761 | cagaguuacaguucuguggTT | 762 | ccacagaacuguaacucugTT |
| 6731 | 1354 | 763 | gcagaguuacaguucugugguu | double | 764 | agaguuacaguucugugguTT | 765 | accacagaacuguaacucuTT |
| 6732 | 1374 | 766 | uuucauguuaguuaccuuauagu | double | 767 | ucauguuaguuaccuuauaTT | 768 | uauaagguaacuaacaugaTT |
| 6733 | 1375 | 769 | uucauguuaguuaccuuauaguu | double | 770 | cauguuaguuaccuuauagTT | 771 | cuauaagguaacuaacaugTT |
| 6734 | 1376 | 772 | ucauguuaguuaccuuauaguua | double | 773 | auguuaguuaccuuauaguTT | 774 | acuauaagguaacuaacauTT |
| 6735 | 1377 | 775 | cauguuaguuaccuuauaguuac | double | 776 | uguuaguuaccuuauaguuTT | 777 | aacuauaagguaacuaacaTT |
| 6736 | 1378 | 778 | auguuaguuaccuuauaguuacu | double | 779 | guuaguuaccuuauaguuaTT | 780 | uaacuauaagguaacuaacTT |
| 6737 | 1379 | 781 | uguuaguuaccuuauaguuacug | double | 782 | uuaguuaccuuauaguuacTT | 783 | guaacuauaagguaacuaaTT |
| 6738 | 1380 | 784 | guuaguuaccuuauaguuacugu | double | 785 | uaguuaccuuauaguuacuTT | 786 | aguaacuauaagguaacuaTT |
| 6739 | 1381 | 787 | uuaguuaccuuauaguuacugug | double | 788 | aguuaccuuauaguuacugTT | 789 | caguaacuauaagguaacuTT |
| 6740 | 1382 | 790 | uaguuaccuuauaguuacugugu | double | 791 | guuaccuuauaguuacuguTT | 792 | acaguaacuauaagguaacTT |
| 6741 | 1383 | 793 | aguuaccuuauaguuacugugua | double | 794 | uuaccuuauaguuacugugTT | 795 | cacaguaacuauaagguaaTT |
| 6742 | 1384 | 796 | guuaccuuauaguuacuguguaa | double | 797 | uaccuuauaguuacuguguTT | 798 | acacaguaacuauaagguaTT |
| 6743 | 1385 | 799 | uuaccuuauaguuacuguguaau | double | 800 | accuuauaguuacuguguaTT | 801 | uacacaguaacuauaagguTT |
| 6744 | 1386 | 802 | uaccuuauaguuacuguguaauu | double | 803 | ccuuauaguuacuguguaaTT | 804 | uuacacaguaacuauaaggTT |
| 6745 | 1387 | 805 | accuuauaguuacuguguaauua | double | 806 | cuuauaguuacuguguaauTT | 807 | auuacacaguaacuauaagTT |
| 6746 | 1388 | 808 | ccuuauaguuacuguguaauuag | double | 809 | uuauaguuacuguguaauuTT | 810 | aauuacacaguaacuauaaTT |
| 6747 | 1389 | 811 | cuuauaguuacuguguaauuagu | double | 812 | uauaguuacuguguaauuaTT | 813 | uaauuacacaguaacuauaTT |
| 6748 | 1390 | 814 | uuauaguuacuguguaauuagug | double | 815 | auaguuacuguguaauuagTT | 816 | cuaauuacacaguaacuauTT |
| 6749 | 1391 | 817 | uauaguuacuguguaauuagugc | double | 818 | uaguuacuguguaauuaguTT | 819 | acuaauuacacaguaacuaTT |
| 6750 | 1392 | 820 | auaguuacuguguaauuagugcc | double | 821 | aguuacuguguaauuagugTT | 822 | cacuaauuacacaguaacuTT |
| 6751 | 1393 | 823 | uaguuacuguguaauuagugcca | double | 824 | guuacuguguaauuagugcTT | 825 | gcacuaauuacacaguaacTT |
| 6752 | 1394 | 826 | aguuacuguguaauuagugccac | double | 827 | uuacuguguaauuagugccTT | 828 | ggcacuaauuacacaguaaTT |
| 6753 | 1395 | 829 | guuacuguguaauuagugccacu | double | 830 | uacuguguaauuagugccaTT | 831 | uggcacuaauuacacaguaTT |
| 6754 | 1396 | 832 | uuacuguguaauuagugccacuu | double | 833 | acuguguaauuagugccacTT | 834 | guggcacuaauuacacaguTT |
| 6755 | 1397 | 835 | uacuguguaauuagugccacuua | double | 836 | cuguguaauuagugccacuTT | 837 | aguggcacuaauuacacagTT |

TABLE 1-continued

Exemplary iRNA agents for targeting RhoA mRNA

| Agent number. | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6756 | 1398 | 838 | acuguguaauuagugccacuuaa | double | 839 | uguguaauuagugccacuuTT | 840 | aaguggcacuaauuacacaTT |
| 6757 | 1399 | 841 | cuguguaauuagugccacuuaau | double | 842 | guguaauuagugccacuuaTT | 843 | uaaguggcacuaauuacacTT |
| 6758 | 1400 | 844 | uguguaauuagugccacuuaaug | double | 845 | uguaauuagugccacuuaaTT | 846 | uuaaguggcacuaauuacaTT |
| 6759 | 1401 | 847 | guguaauuagugccacuuaaugu | double | 848 | guaauuagugccacuuaauTT | 849 | auuaaguggcacuaauuacTT |
| 6760 | 1402 | 850 | uguaauuagugccacuuaaugua | double | 851 | uaauuagugccacuuaaugTT | 852 | cauuaaguggcacuaauuaTT |
| 6761 | 1403 | 853 | guaauuagugccacuuaauguau | double | 854 | aauuagugccacuuaauguTT | 855 | acauuaaguggcacuaauuTT |
| 6762 | 1404 | 856 | uaauuagugccacuuaauguaug | double | 857 | auuagugccacuuaauguaTT | 858 | uacauuaaguggcacuaauTT |
| 6763 | 1405 | 859 | aauuagugccacuuaauguaugu | double | 860 | uuagugccacuuaauguauTT | 861 | auacauuaaguggcacuaaTT |
| 6764 | 1406 | 862 | auuagugccacuuaauguauguu | double | 863 | uagugccacuuaauguaugTT | 864 | cauacauuaaguggcacuaTT |
| 6765 | 1407 | 865 | uuagugccacuuaauguauguua | double | 866 | agugccacuuaauguauguTT | 867 | acauacauuaaguggcacuTT |
| 6766 | 1408 | 868 | uagugccacuuaauguauguuac | double | 869 | gugccacuuaauguauguuTT | 870 | aacauacauuaaguggcacTT |
| 6767 | 1409 | 871 | agugccacuuaauguauguuacc | double | 872 | ugccacuuaauguauguuaTT | 873 | uaacauacauuaaguggcaTT |
| 6768 | 1410 | 874 | gugccacuuaauguauguuacca | double | 875 | gccacuuaauguauguuacTT | 876 | guaacauacauuaaguggcTT |
| 6769 | 1411 | 877 | ugccacuuaauguauguuaccaa | double | 878 | ccacuuaauguauguuaccTT | 879 | gguaacauacauuaagugg TT |
| 6770 | 1412 | 880 | gccacuuaauguauguuaccaaa | double | 881 | cacuuaauguauguuaccaTT | 882 | ugguaacauacauuaagugTT |
| 6771 | 1413 | 883 | ccacuuaauguauguuaccaaaa | double | 884 | acuuaauguauguuaccaaTT | 885 | uugguaacauacauuaaguTT |
| 6772 | 1414 | 886 | cacuuaauguauguuaccaaaaa | double | 887 | cuuaauguauguuaccaaaTT | 888 | uuugguaacauacauuaagTT |
| 6773 | 1415 | 889 | acuuaauguauguuaccaaaaau | double | 890 | uuaauguauguuaccaaaaTT | 891 | uuuugguaacauacauuaaTT |
| 6774 | 1416 | 892 | cuuaauguauguuaccaaaaaua | double | 893 | uaauguauguuaccaaaaaTT | 894 | uuuuugguaacauacauuaTT |
| 6775 | 1435 | 895 | aauaaauauaucuaccccagacu | double | 896 | uaaauauaucuaccccagaTT | 897 | ucugggguagauauauuuaTT |
| 6776 | 1436 | 898 | auaaauauaucuaccccagacua | double | 899 | aaauauaucuaccccagacTT | 900 | gucugggguagauauauuuTT |
| 6777 | 1437 | 901 | uaaauauaucuaccccagacuag | double | 902 | aauauaucuaccccagacuTT | 903 | agucugggguagauauauuTT |
| 6778 | 1438 | 904 | aaauauaucuaccccagacuaga | double | 905 | auauaucuaccccagacuaTT | 906 | uagucugggguagauauauTT |
| 6779 | 1439 | 907 | aauauaucuaccccagacuagau | double | 908 | uauaucuaccccagacuagTT | 909 | cuagucugggguagauauaTT |
| 6780 | 1440 | 910 | auauaucuaccccagacuagaug | double | 911 | auaucuaccccagacuagaTT | 912 | ucuagucugggguagauauTT |
| 6781 | 1441 | 913 | uauaucuaccccagacuagaugu | double | 914 | uaucuaccccagacuagauTT | 915 | aucuagucugggguagauaTT |
| 6782 | 1442 | 916 | auaucuaccccagacuagaugua | double | 917 | aucuaccccagacuagaugTT | 918 | caucuagucugggguagauTT |
| 6783 | 1443 | 919 | uaucuaccccagacuagauguag | double | 920 | ucuaccccagacuagauguTT | 921 | acaucuagucugggguagaTT |
| 6784 | 1444 | 922 | aucuaccccagacuagauguagu | double | 923 | cuaccccagacuagauguaTT | 924 | uacaucuagucugggguagTT |
| 6785 | 1445 | 925 | ucuaccccagacuagauguagua | double | 926 | uaccccagacuagauguagTT | 927 | cuacaucuagucuggggua TT |
| 6786 | 1446 | 928 | cuaccccagacuagauguaguau | double | 929 | accccagacuagauguaguTT | 930 | acuacaucuagucuggggu TT |
| 6787 | 1447 | 931 | uaccccagacuagauguaguauu | double | 932 | ccccagacuagauguaguaTT | 933 | uacuacaucuagucugggg TT |
| 6788 | 1448 | 934 | accccagacuagauguaguauuu | double | 935 | cccagacuagauguaguauTT | 936 | auacuacaucuagucuggg TT |
| 6789 | 1449 | 937 | ccccagacuagauguaguauuuu | double | 938 | ccagacuagauguaguauuTT | 939 | aauacuacaucuagucuggTT |
| 6790 | 1450 | 940 | cccagacuagauguaguauuuuu | double | 941 | cagacuagauguaguauuuTT | 942 | aaauacuacaucuagucugTT |

TABLE 1-continued

Exemplary iRNA agents for targeting RhoA mRNA

| Agent number. | Start pos. in RNA[b] | SEQ ID NO. | target sequence (5'-3') | duplex design (over-hang)[a] | sense strand SEQ ID NO. | sequence (5'-3') | antisense strand SEQ ID NO. | sequence (5'-3') |
|---|---|---|---|---|---|---|---|---|
| 6791 | 1451 | 943 | ccagacuagauguaguauuuuuu | double | 944 | agacuagauguaguauuuuuTT | 945 | aaaauacuacaucuagucuTT |
| 6792 | 1452 | 946 | cagacuagauguaguauuuuug | double | 947 | gacuagauguaguauuuuugTT | 948 | aaaaauacuacaucuagucTT |
| 6793 | 1453 | 949 | agacuagauguaguauuuuugu | double | 950 | acuagauguaguauuuuuguTT | 951 | aaaaaauacuacaucuaguTT |
| 6794 | 1454 | 952 | gacuagauguaguauuuuugua | double | 953 | cuagauguaguauuuuuguaTT | 954 | caaaaaauacuacaucuagTT |
| 6795 | 1455 | 955 | acuagauguaguauuuuuguau | double | 956 | uagauguaguauuuuuguauTT | 957 | acaaaaaauacuacaucuaTT |
| 6796 | 1456 | 958 | cuagauguaguauuuuuguaua | double | 959 | agauguaguauuuuuguauaTT | 960 | uacaaaaaauacuacaucuTT |
| 6797 | 1457 | 961 | uagauguaguauuuuuguauaa | double | 962 | gauguaguauuuuuguauaaTT | 963 | auacaaaaaauacuacaucTT |
| 6798 | 1458 | 964 | agauguaguauuuuuguauaau | double | 965 | auguaguauuuuuguauaauTT | 966 | uauacaaaaaauacuacauTT |
| 6799 | 1459 | 967 | gauguaguauuuuuguauaauu | double | 968 | uguaguauuuuuguauaauuTT | 969 | uuauacaaaaaauacuacaTT |
| 6800 | 1460 | 970 | auguaguauuuuuguauaauug | double | 971 | guaguauuuuuguauaauugTT | 972 | auuauacaaaaaauacuacTT |
| 6801 | 1461 | 973 | uguaguauuuuuguauaauugg | double | 974 | uaguauuuuuguauaauuggTT | 975 | aauuauacaaaaaauacuaTT |
| 6802 | 1462 | 976 | guaguauuuuuguauaauugga | double | 977 | aguauuuuuguauaauuggaTT | 978 | caauuauacaaaaaauacuTT |
| 6803 | 1463 | 979 | uaguauuuuuguauaauuggau | double | 980 | guauuuuuguauaauuggauTT | 981 | ccaauuauacaaaaaauacTT |
| 6804 | 1464 | 982 | aguauuuuuguauaauuggauu | double | 983 | uauuuuuguauaauuggauuTT | 984 | uccaauuauacaaaaaauaTT |
| 6805 | 1465 | 985 | guauuuuuguauaauuggauuu | double | 986 | auuuuuguauaauuggauuuTT | 987 | auccaauuauacaaaaaauTT |
| 6806 | 1466 | 988 | uauuuuuguauaauuggauuuc | double | 989 | uuuuuguauaauuggauuucTT | 990 | aauccaauuauacaaaaaaTT |
| 6807 | 1467 | 991 | auuuuuguauaauuggauuucc | double | 992 | uuuuguauaauuggauuuccTT | 993 | aaauccaauuauacaaaaaTT |
| 6808 | 1468 | 994 | uuuuuguauaauuggauuuccu | double | 995 | uuuguauaauuggauuuccuTT | 996 | gaaauccaauuauacaaaaTT |
| 6809 | 1469 | 997 | uuuuguauaauuggauuuccua | double | 998 | uuguauaauuggauuuccuaTT | 999 | ggaaauccaauuauacaaaTT |
| 6810 | 1470 | 1000 | uuuguauaauuggauuuccuaa | double | 1001 | uuguauaauuggauuuccuaTT | 1002 | aggaaauccaauuauacaaTT |
| 6811 | 1471 | 1003 | uuguauaauuggauuuccuaau | double | 1004 | uguauaauuggauuuccuaaTT | 1005 | uaggaaauccaauuauacaTT |
| 6812 | 1472 | 1006 | uguauaauuggauuuccuaaua | double | 1007 | guauaauuggauuuccuaauTT | 1008 | uuaggaaauccaauuauacTT |
| 6813 | 1473 | 1009 | guauaauuggauuuccuaauac | double | 1010 | uauaauuggauuuccuaauTT | 1011 | auuaggaaauccaauuauaTT |
| 6814 | 1540 | 1012 | guauuuggaaauaaagucagaug | double | 1013 | auuuggaaauaaagucagaTT | 1014 | ucugacuuuauuccaaauTT |
| 6815 | 1541 | 1015 | uauuuggaaauaaagucagaugg | double | 1016 | uuuggaaauaaagucagauTT | 1017 | aucugacuuuauuccaaaTT |
| 6816 | 1542 | 1018 | auuuggaaauaaagucagaugga | double | 1019 | uuggaaauaaagucagaugTT | 1020 | caucugacuuuauuccaaTT |
| 6817 | 1543 | 1021 | uuuggaaauaaagucagauggaa | double | 1022 | uggaaauaaagucagauggTT | 1023 | ccaucugacuuuauuccaTT |
| 6818 | 1544 | 1024 | uuggaaauaaagucagauggaaa | double | 1025 | ggaaauaaagucagauggaTT | 1026 | uccaucugacuuuauuccTT |
| 6819 | 1545 | 1027 | uggaaauaaagucagauggaaaa | double | 1028 | gaaauaaagucagauggaaTT | 1029 | uuccaucugacuuuauucTT |
| 6820 | 1796 | 1030 | ucccucccagaggagccaccagu | double | 1031 | ccucccagaggagccaccaTT | 1032 | ugguggcuccucugggaggTT |
| 6821 | 1797 | 1033 | cccucccagaggagccaccaguu | double | 1034 | cucccagaggagccaccagTT | 1035 | cugguggcuccucugggagTT |
| 6822 | 1798 | 1036 | ccucccagaggagccaccaguuc | double | 1037 | ucccagaggagccaccaguTT | 1038 | acugguggcuccucugggaTT |
| 6823 | 1799 | 1039 | cucccagaggagccaccaguucu | double | 1040 | cccagaggagccaccaguuTT | 1041 | aacugguggcuccucugggTT |
| 6824 | 1800 | 1042 | ucccagaggagccaccaguucuc | double | 1043 | ccagaggagccaccaguucTT | 1044 | gaacugguggcuccucugTT |
| 6825 | 1801 | 1045 | cccagaggagccaccaguucuca | double | 1046 | cagaggagccaccaguucuTT | 1047 | agaacugguggcuccucugTT |

TABLE 1-continued

Exemplary iRNA agents for targeting RhoA mRNA

| Agent number. | Start pos. in RNA[b] | SEQ ID NO. | target sequence (5'-3') | duplex design (over-hang)[a] | SEQ ID NO. | sense strand sequence (5'-3') | SEQ ID NO. | antisense strand sequence (5'-3') |
|---|---|---|---|---|---|---|---|---|
| 6826 | 1843 | 1048 | cuucucuccagcugacuaaacuu | double | 1049 | ucucuccagcugacuaaacTT | 1050 | guuuagucagcuggagagaTT |
| 6827 | 1869 | 1051 | uucuguaccaguuaauuuuucca | double | 1052 | cuguaccaguuaauuuuucTT | 1053 | gaaaaauuaacugguacagTT |
| 6828 | 1870 | 1054 | ucuguaccaguuaauuuuuccaa | double | 1055 | uguaccaguuaauuuuuccTT | 1056 | ggaaaaauuaacugguacaTT |
| 6829 | 1871 | 1057 | cuguaccaguuaauuuuuccaac | double | 1058 | guaccaguuaauuuuuccaTT | 1059 | uggaaaaauuaacugguacTT |
| 6830 | 1872 | 1060 | uguaccaguuaauuuuuccaacu | double | 1061 | uaccaguuaauuuuuccaaTT | 1062 | uuggaaaaauuaacugguaTT |
| 6831 | 1873 | 1063 | guaccaguuaauuuuuccaacua | double | 1064 | accaguuaauuuuuccaacTT | 1065 | guuggaaaaauuaacugguTT |
| 6832 | 1874 | 1066 | uaccaguuaauuuuuccaacuac | double | 1067 | ccaguuaauuuuuccaacuTT | 1068 | aguuggaaaaauuaacuggTT |
| 6833 | 1875 | 1069 | accaguuaauuuuuccaacuacu | double | 1070 | caguuaauuuuuccaacuaTT | 1071 | uaguuggaaaaauuaacugTT |
| 6834 | 1897 | 1072 | uaauagaauaaaggcaguuuucu | double | 1073 | auagaauaaaggcaguuuuTT | 1074 | aaaacugccuuuauucuauTT |
| 6835 | 1898 | 1075 | aauagaauaaaggcaguuuucua | double | 1076 | uagaauaaaggcaguuuucTT | 1077 | gaaaacugccuuuauucuaTT |
| 6836 | 1899 | 1078 | auagaauaaaggcaguuuucaa | double | 1079 | agaauaaaggcaguuuucuTT | 1080 | agaaaacugccuuuauucuTT |

[a]Single: Single overhang design 21 mer sense, corresponding 23 mer antisense with 2 nucleotides overhang at 3' end; Double: double overhang design corresponding 19 mer sense and antisense strand each with 2 dT nucleotide overhang at 3' end
[b]"Start position" corresponds to the position within the sequence of human RhoA (Genbank accession no. NM_001664) mRNA to which the 5'-most nucleotide of the sense strand corresponds for single overhang designs; for double overhang designs, the 5'-most ribonucleotide of the sense strand corresponds to (Start position +2)

Based on these results, the invention specifically provides an iRNA agent that includes a sense strand having at least 15 contiguous nucleotides of the sense strand sequences of the agents provided in Table 1 under agent numbers 6477-6836, and an antisense strand having at least 15 contiguous nucleotides of the antisense sequences of the agents provided in Table 1 under agent numbers 6477 to 6836.

The iRNA agents shown in Table 1 are composed of two strands of 19 nucleotides in length which are complementary or identical to the target sequence, plus a 3'-TT overhang. The present invention provides agents that comprise 15 contiguous nucleotides from these agents. However, while these lengths may potentially be optimal, the iRNA agents are not meant to be limited to these lengths. The skilled person is well aware that shorter or longer iRNA agents may be similarly effective, since, within certain length ranges, the efficacy is rather a function of the nucleotide sequence than strand length. For example, Yang, et al., *PNAS* 99:9942-9947 (2002), demonstrated similar efficacies for iRNA agents of lengths between 21 and 30 base pairs. Others have shown effective silencing of genes by iRNA agents down to a length of approx. 15 base pairs (Byrom, et al., "Inducing RNAi with siRNA Cocktails Generated by RNase III" *Tech Notes* 10(1), Ambion, Inc., Austin, Tex.).

Therefore, it is possible and contemplated by the instant invention to select from the sequences provided in Table 1 under agent numbers 6477 to 6836 a partial sequence of between 15 to 22 nucleotides for the generation of an iRNA agent derived from one of the sequences provided in Table 1 under agent numbers 6477 to 6836. Alternatively, one may add one or several nucleotides to one of the sequences provided in Table 1 under agent numbers 6477 to 6836, or an agent comprising 15 contiguous nucleotides from one of these agents, preferably, but not necessarily, in such a fashion that the added nucleotides are complementary to the respective sequence of the target gene, e.g., RhoA. For example, the first 15 nucleotides from one of the agents can be combined with the 8 nucleotides found 5' to these sequence in the RhoA mRNA to obtain an agent with 23 nucleotides in the sense and antisense strands. All such derived iRNA agents are included in the iRNA agents of the present invention, provided they essentially retain the ability to inhibit RhoA expression in cultured human RhoA expressing cells.

The antisense strand of an iRNA agent should be equal to or at least, 14, 15, 16 17, 18, 19, 25, 29, 40, or 50 nucleotides in length. It should be equal to or less than 60, 50, 40, or 30, nucleotides in length. Preferred ranges are 15-30, 17 to 25, 19 to 23, and 19 to 21 nucleotides in length.

The sense strand of an iRNA agent should be equal to or at least 14, 15, 16 17, 18, 19, 25, 29, 40, or 50 nucleotides in length. It should be equal to or less than 60, 50, 40, or 30 nucleotides in length. Preferred ranges are 15-30, 17 to 25, 19 to 23, and 19 to 21 nucleotides in length.

The double stranded portion of an iRNA agent should be equal to or at least, 15, 16 17, 18, 19, 20, 21, 22, 23, 24, 25, 29, 40, or 50 nucleotide pairs in length. It should be equal to or less than 60, 50, 40, or 30 nucleotides pairs in length. Preferred ranges are 15-30, 17 to 25, 19 to 23, and 19 to 21 nucleotides pairs in length.

Generally, the iRNA agents of the instant invention include a region of sufficient complementarity to the respective RhoA gene, and are of sufficient length in terms of nucleotides, that the iRNA agent, or a fragment thereof, can mediate down regulation of the RhoA gene. The ribonucleotide portions of the antisense strands of the iRNA agents of Table 1 under agent numbers 6477 to 6836 are fully complementary to the mRNA sequences of the RhoA gene, respectively, and ribonucleotide portion of their sense strands are fully complementary to the ribonucleotide portions of the respective antisense strands, except for the two 3'-terminal nucleotides on the antisense strand in single overhang design iRNA agents. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of a RhoA mRNA.

Therefore, the iRNA agents of the instant invention include agents comprising a sense strand and antisense strand each comprising a sequence of at least 16, 17 or 18 nucleotides which is essentially identical, as defined below, to one of the sequences of Table 1 under agent numbers 6477 to 6836, except that not more than 1, 2 or 3 nucleotides per strand, respectively, have been substituted by other nucleotides (e.g. adenosine replaced by uracil), while essentially retaining the ability to inhibit RhoA expression in cultured human RhoA expressing cells, respectively. These agents will therefore possess at least 15 nucleotides identical to one of the sequences of Table 1 under agent numbers 6477 to 6836, but 1, 2 or 3 base mismatches with respect to either the target RhoA mRNA sequence or between the sense and antisense strand are introduced. Mismatches to the target RhoA mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule. Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length, at one or both ends of the iRNA agent. The overhangs can be the result of one strand being longer than the other, or the result of two strands of the same length being staggered. The unpaired nucleotides forming the overhang can be ribonucleotides, or they can be deoxyribonucleotides, preferably thymidine. 5'-ends are preferably phosphorylated.

Preferred lengths for the duplexed region are between 15 and 30, most preferably 18, 19, 20, 21, 22, and 23 nucleotides in length, e.g., in the siRNA agent range discussed above. siRNA agents can resemble in length and structure the natural Dicer processed products from long dsRNAs. Embodiments in which the two strands of the siRNA agent are linked, e.g., covalently linked, are also included. Hairpin, or other single strand structures which provide the required double stranded region, and preferably a 3' overhang are also within the invention.

Evaluation of Candidate iRNA Agents

A candidate iRNA agent can be evaluated for its ability to downregulate target gene expression. For example, a candidate iRNA agent can be provided, and contacted with a cell, that expresses the target gene, e.g., the RhoA gene, either endogenously or because it has been transfected with a construct from which a RhoA protein can be expressed. The level of target gene expression prior to and following contact with the candidate iRNA agent can be compared, e.g., on an mRNA or protein level. If it is determined that the amount of RNA or protein expressed from the target gene is lower following contact with the iRNA agent, then it can be concluded that the iRNA agent downregulates target gene expression. The level of target RhoA RNA or RhoA protein in the cell can be determined by any method desired. For example, the level of target RNA can be determined by Northern blot analysis, reverse transcription coupled with polymerase chain reaction (RT-PCR), or RNAse protection assay. The level of protein can be determined, for example, by Western blot analysis or immuno-fluorescence. Preferably, the assay also tests the ability of the iRNA agent to inhibit RhoA expression on a functional level, e.g. by assessing the ability of the iRNA agent to facilitate neuronal growth, e.g. the restoration of neurite outgrowth on an otherwise inhibitory substrate, e.g a substrate comprising myelin.

Stability Testing, Modification, and Retesting of iRNA Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-methyl group. This further iRNA agent can be retested for stability, and this process may be iterated until an iRNA agent is found exhibiting the desired stability.

In Vivo Testing

An iRNA agent identified as being capable of inhibiting RhoA gene expression can be tested for functionality in vivo in an animal model (e.g., in a mammal, such as in mouse or rat). For example, the iRNA agent can be administered to an animal, and the iRNA agent evaluated with respect to its biodistribution, stability, and its ability to inhibit RhoA gene expression or reduce a biological or pathological process mediated at least in part by RhoA.

The iRNA agent can be administered directly to the target tissue, e.g. the spinal cord, and, in the case of a spinal cord injury model, to the site of spinal cord injury, such as by injection. Preferably, the iRNA agent is administered to the animal model in the same manner that it would be administered to a human.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}S$, $^{32}P$, $^{33}P$, or $^{3}H$; gold particles; or antigen particles for immunohistochemistry).

The iRNA agent can be evaluated with respect to its ability to down regulate RhoA gene expression. Levels of RhoA gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. RhoA mRNA can be detected by any desired method, including but not limited to RT-PCR, Northern blot, branched-DNA assay, or RNAase protection assay. Alternatively, or additionally, RhoA gene expression can be monitored by performing Western blot analysis on tissue extracts treated with the iRNA agent.

Animal models may be used to establish the concentration necessary to achieve a certain desired effect (e.g., $EC_{50}$ or $ED_{50}$). Such animal models may include transgenic animals that express a human gene, e.g., a gene that produces a target human RhoA RNA. In another embodiment, the composition for testing includes an iRNA agent that is complementary, at least in an internal region, to a sequence that is conserved between the target RhoA RNA in the animal model and the target RhoA RNA in a human.

iRNA Chemistry

Described herein are isolated iRNA agents, e.g., ds RNA agents that mediate RNAi to inhibit expression of a RhoA gene.

RNA agents discussed herein include otherwise unmodified RNA as well as RNA which has been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. Nucleic Acids Res. 22: 2183-2196, 1994. Such rare or unusual RNAs, often termed modified RNAs (apparently because they are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829, filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070, filed on Mar. 8, 2004.

An iRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070, filed on Mar. 8, 2004.

An iRNA agent can be complexed with an amphipathic moiety. Exemplary amphipathic moieties for use with iRNA agents are described in co-owned PCT Application No. PCT/US2004/07070, filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070, filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070, filed on Mar. 8, 2004.

Enhanced Nuclease Resistance

An iRNA agent, e.g., an iRNA agent that targets RhoA, can have enhanced resistance to nucleases. Naked RNA is often an easy prey for nucleolytic enzymes, such as exonucleases and endonucleases, which are omnipresent in biological media, such as the cellular cytoplasm, blood, or cerebrospinal fluid (CSF). Quick degradation can severely hamper the ability of an siRNA to inhibit the expression of a target gene. The vulnerability towards nucleolytic degradation can be greatly reduced by chemically modifying certain nucleotides of an siRNA. However, adding modifications in order to stabilize an siRNA sometimes represents a trade-off with its activity, and stabilizing modifications may even introduce toxic effects. It is therefore desirable to introduce the minimum number of modifications that still imparts the desired level of stability. Modifications in the sense strand usually have less impact on the activity of an siRNA.

In order to increase the stability of an siRNA towards nucleolytic degradation by endonucleases, it is therefore advantageous to modify only a limited number of nucleotides in particularly degradation prone positions, as described in co-owned U.S. Application No. 60/559,917, filed on May 4, 2004, co-owned U.S. Application No. 60/574,744, filed on May 27, 2004, and co-owned international application PCT/US2005/018931, filed May 27, 2005. We have determined that pyrimidine nucleotides, and specifically the 5' nucleotide in a 5'-ua-3' sequence context, a 5'-ug-3' sequence context, a 5'-ca-3' sequence context, a 5'-uu-3' sequence context, or a 5'-ca-3' sequence context are particularly prone to degradative attack, in that approximate order. Sufficiently stable and highly active siRNAs have been obtained by our laboratory when the 5'-most pyrimidines in all occurrences of the sequence contexts 5'-ua-3' and 5'-ca-3', or in all occurrences of 5'-ua-3',5'-ca-3', and 5'-uu-3', or in all occurrences of 5'-ua-3',5'-ca-3',5'-uu-3', and 5'-ug-3' were replaced by 2'-modified nucleotides, such as 2'-O-methyl nucleotides, in both strands. Alternatively, 2'-modifying all pyrimidine nucleotides in the sense strand and the 5'-most pyrimidines in all occurrences of the sequence contexts 5'-ua-3' and 5'-ca-3' in the antisense strand has given good results in terms of activity and stability. Sometimes, it has been necessary to 2'-modify all pyrimidine nucleotides in the sense strand and the 5'-most pyrimidines in all occurrences of the sequence contexts 5'-ua-3',5'-ca-3',5'-uu-3', and 5'-ug-3' in the antisense strand. The iRNA agent can include at least 2, at least 3, at least 4 or at least 5 of such dinucleotides.

Preferably, the 2'-modified nucleotides include, for example, a 2'-modified ribose unit, e.g., the 2'-hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-AMINE and aminoalkoxy, O(CH$_2$)$_n$AMINE, (e.g., AMINE=NH$_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'-OCH$_3$, 2'-O-allyl, 2'-C-allyl, and 2'-fluoro.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Nucleolytic cleavage can also be inhibited by the introduction of phosphate linker modifications, e.g., phosphorothioate linkages. Thus, preferred iRNA agents include nucleotide dimers enriched or pure for a particular chiral form of a modified phosphate group containing a heteroatom at a non-bridging position normally occupied by oxygen. The heteroatom can be S, Se, Nr$_2$, or Br$_3$. When the heteroatom is S, enriched or chirally pure Sp linkage is preferred. Enriched means at least 70, 80, 90, 95, or 99% of the preferred form. Modified phosphate linkages are particularly efficient in inhibiting exonucleolytic cleavage when introduced near the 5'- or 3'-terminal positions, and preferably the 5'-terminal positions, of an iRNA agent.

5' conjugates can also inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications can inhibit hybridization so it is preferable to use them only in terminal regions, and preferable to not use them at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the cleavage site, on the target or on the iRNA agent strand which hybridizes to it. Cleavage region means the nucleotides within 1, 2, or 3 nucleotides of the cleavagee site, in either direction.

Such modifications can be introduced into the terminal regions, e.g., at the terminal position or with 2, 3, 4, or 5 positions of the terminus, of a sense or antisense strand.

Tethered Ligands

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic molecules, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

5'-Phosphate Modifications

In preferred embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether-methoxymethyl (MeOCH2-), ethoxymethyl, etc., e.g. RP(OH)(O)—O-5'-).

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Transport of iRNA Agents into Cells

Not wishing to be bound by any theory, the chemical similarity between cholesterol-conjugated iRNA agents and certain constituents of lipoproteins (e.g. cholesterol, cholesteryl esters, phospholipids) may lead to the association of iRNA agents with lipoproteins (e.g. LDL, HDL) in blood and/or the interaction of the iRNA agent with cellular components having an affinity for cholesterol, e.g. components of the cholesterol transport pathway. Lipoproteins as well as their constituents are taken up and processed by cells by various active and passive transport mechanisms, for example, without limitation, endocytosis of LDL-receptor bound LDL, endocytosis of oxidized or otherwise modified LDLs through interaction with Scavenger receptor A, Scavenger receptor B1-mediated uptake of HDL cholesterol in the liver, pinocytosis, or transport of cholesterol across membranes by ABC (ATP-binding cassette) transporter proteins, e.g. ABC-A1, ABC-G1 or ABC-G4. Hence, cholesterol-conjugated iRNA agents could enjoy facilitated uptake by cells possessing such transport mechanisms, e.g. cells of the liver. As such, the present invention provides evidence and general methods for targeting iRNA agents to cells expressing certain cell surface components, e.g. receptors, by conjugating a natural ligand for such component (e.g. cholesterol) to the iRNA agent, or by conjugating a chemical moiety (e.g. cholesterol) to the iRNA agent which associates with or binds to a natural ligand for the component (e.g. LDL, HDL).

Other Embodiments

An RNA, e.g., an iRNA agent, can be produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of an iRNA agent and one that produces a transcript that includes the bottom strand of an iRNA agent. When the templates are transcribed, the iRNA agent is produced, and processed into siRNA agent fragments that mediate gene silencing.

Formulation

The iRNA agents described herein can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA agent preparation includes two or more iRNA agent(s), e.g., two or more iRNA agents that can mediate RNAi with respect to the same gene, or different alleles of the gene, or with respect to different genes. Such preparations can include at least three, five, ten, twenty, fifty, or a hundred or more different iRNA agent species. Such iRNA agents can mediate RNAi with respect to a similar number of different genes.

Where the two or more iRNA agents in such preparation target the same gene, they can have target sequences that are non-overlapping and non-adjacent, or the target sequences may be overlapping or adjacent.

Disorders Associated with RhoA Expression

An iRNA agent that targets RhoA, e.g., an iRNA agent described herein, can be used to treat a subject, e.g., a human having or at risk for developing a disease or disorder associated with RhoA gene expression or treating a subject where a biological process mediated by RhoA is unwanted. Since Nogo-L, RhoA, and Nogo-R participate in inhibiting axonal growth and elongations, the iRNA agents of the present invention are used to reverse this inhibition leading to nerve/ axonal growth and elongation. Such a treatment is useful in treating injuries to the nervous system such as spinal cord injury or peripheral nerve death (caused by, e.g., Metastatic cancers of the CNS, e.g., gliomas (such as glioblastomas, astrocytomas, oligodendrogliomas, ependymomas), meningiomas, medulloblastomas, neuroblastomas, choroid plexus papillomas, sarcomas can also be treated by the iRNA agents described herein. Other indications include diseases of the central nervous system, including but not limited to encephalomyelitis, ischemic stroke, Alzheimer's Disease, spongiform encephalopathy, Amyotrophic lateral sclerosis (ALS), spinal muscular atrophy (SMA), multiple sclerosis, transverse myelitis, motor neuron disease, Guillan Barre, Anterior Spinal Artery Syndrome, and schizophrenia.

For example, an iRNA agent that targets RhoA mRNA can be used to treat a subject with a spinal cord injury or a subject having another pathological state which can be ameliorated, at least in part, by nerve growth and elongation. In such a use, an iRNA agent of the present invention is administered preferably locally at the site of nerve damage or the site at which the inhibitory effects of RhoA is desired to be reversed. Administration of the iRNA agent leads to decrease in RhoA protein resulting in reversing Nogo mediated inhibition of axonal elongation and growth.

Treatment Methods and Routes of Delivery

A composition that includes an iRNA agent, e.g., an iRNA agent that targets RhoA, can be delivered to a subject by a variety of routes to achieve either local delivery to the site of action of systemic delivery to the subject. Exemplary routes include direct injection to the site of treatment, intrathecal, parenchymal, intravenous, nasal, oral, and ocular delivery. The preferred means of administering the iRNA agents of the present invention is through direct injection or infusion to the site of treatment.

An iRNA agent can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, or intrathecal or intraventricular administration.

The route of delivery can be dependent on the disorder of the patient. In general, the delivery of the iRNA agents of the present invention is done to achieve systemic delivery into the subject. One preferred means of achieving this is through parenteral administration. In a particularly preferred embodiment, the application is achieved by direct application of the pharmaceutical composition to the site of nerve injury, such as the site of spinal cord injury. Formulations for parenteral administration may include sterile aqueous solutions which may also contain buffers, diluents and other suitable additives. For intravenous use, the total concentration of solutes should be controlled to render the preparation isotonic.

Using the small interfering RNA vectors previously described, the invention also provides devices, systems, and methods for delivery of small interfering RNA to target locations in the nervous system and or/the brain. The envisioned route of delivery is through the use of implanted, indwelling, intrathecal or intraparenchymal catheters that provide a means for injecting small volumes of fluid containing the dsRNA of the invention directly into local nerves or local brain tissue. The proximal end of these catheters may be connected to an implanted, intrathecal or intracerebral access port surgically affixed to the patient's body or cranium, or to an implanted drug pump located in the patient's torso.

Alternatively, implantable delivery devices, such as an implantable pump may be employed. Examples of the delivery devices within the scope of the invention include the Model 8506 investigational device (by Medtronic, Inc. of Minneapolis, Minn.), which can be implanted subcutaneously in the body or on the cranium, and provides an access port through which therapeutic agents may be delivered to the nerves or brain. Delivery occurs through a stereotactically implanted polyurethane catheter. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPA1 catheter by Medtronic, Inc., for delivery to the brain tissue itself (i.e., intraparenchymal delivery), disclosed in U.S. Ser. Nos. 09/540,444 and 09/625,751, which are incorporated herein by reference. The latter catheter has multiple outlets on its distal end to deliver the therapeutic agent to multiple sites along the catheter path. In addition to the aforementioned device, the delivery of the small interfering RNA vectors in accordance with the invention can be accomplished with a wide variety of devices, including but not limited to U.S. Pat. Nos. 5,735,814, 5,814,014, and 6,042,579, all of which are incorporated herein by reference. Using the teachings of the invention and those of skill in the art will recognize that these and other devices and systems may be suitable for delivery of small interfering RNA vectors for the treatment of pain in accordance with the invention.

In one such embodiment, the method further comprises the steps of implanting a pump outside the body or brain, the pump coupled to a proximal end of the catheter, and operating the pump to deliver the predetermined dosage of the at least one small interfering RNA or small interfering RNA vector through the discharge portion of the catheter. A further embodiment comprises the further step of periodically refreshing a supply of the at least one small interfering RNA or small interfering RNA vector to the pump outside said body or brain.

Thus, the invention includes the delivery of small interfering RNA vectors using an implantable pump and catheter, like that taught in U.S. Pat. Nos. 5,735,814 and 6,042,579, and further using a sensor as part of the infusion system to regulate the amount of small interfering RNA vectors delivered to the nerves or brain, like that taught in U.S. Pat. No. 5,814,014. Other devices and systems can be used in accordance with the method of the invention, for example, the devices and systems disclosed in U.S. Ser. No. 09/872,698 (filed Jun. 1, 2001) and U.S. Ser. No. 09/864,646 (filed May 23, 2001), which are incorporated herein by reference.

Preferably, the outlet of the pump or catheter is placed in close proximity of the desired site of action of the pharmaceutical composition, such as near the site of spinal cord, or other nerve, injury.

Administration can be provided by the subject or by another person, e.g., a caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The term "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered. In one embodiment, both Nogo-L, RhoA, and Nogo-R iRNA agents are co-administered.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage. An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of iRNA agent (e.g., about $4.4\times10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of iRNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. Because iRNA agent mediated silencing can persist for several days after administering the iRNA agent composition, in many instances, it is possible to administer the composition with a frequency of less than once per day, or, for some instances, only once for the entire therapeutic regimen.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of body weight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Following successful treatment, it may be desirable to have the patient undergo maintenance therapy to prevent the recurrence of the disease state, wherein the compound of the invention is administered in maintenance doses, ranging from 0.001 g to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, pulmonary, or topical, such as intrathecal or at the site of nerve injury. For example, topical formulations tend to require much lower concentrations of some ingredients in order to avoid irritation or burning.

Certain factors may influence the dosage required to effectively treat a subject, including but not limited to the severity of the disease or disorder, previous treatments, the general health and/or age of the subject, and other diseases present. It will also be appreciated that the effective dosage of an iRNA agent such as an siRNA used for treatment may increase or decrease over the course of a particular treatment. Changes in dosage may result and become apparent from the results of diagnostic assays. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient, or of drug accumulation at the site of application when delivering locally, e.g. at the site of nerve injury, e.g. at the site of spinal cord injury. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models as described above.

The invention is further illustrated by the following examples, which should not be construed as further limiting.

EXAMPLES

Nucleic acid sequences are represented below using standard nomenclature, and specifically the abbreviations of Table 2.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| N, n | any 2'-deoxy-nucleotide/nucleotide (G, A, C, or T, g, a, c or u) |
| am | 2'-O-methyladenosine-5'-phosphate |
| cm | 2'-O-methylcytidine-5'-phosphate |
| gm | 2'-O-methylguanosine-5'-phosphate |
| tm | 2'-O-methyl-thymidine-5'-phosphate |
| um | 2'-O-methyluridine-5'-phosphate |
| A, C, G, T, U, a, c, g, t, u | underlined: nucleoside-5'-phosphorothioate |
| -Chol | 1-{6-[cholester-3-yloxycarbonylamino]-hexanoyl}-4-hydroxy-pyrrolidin-3-phosphorothioate diester |

[a]capital letters represent 2'-deoxyribonucleotides (DNA), lower case letters represent ribonucleotides (RNA)

Source of Reagents

Where the source of a reagent is not specifically given herein, such reagent may be obtained from any supplier of reagents for molecular biology at a quality/purity standard for application in molecular biology.

Example 1

Selection of Sequences

Sequence alignment was performed to identify regions within the sequence of human RhoA mRNA with full homology to the respective sequences in both mouse and rat RhoA mRNA (human RhoA mRNA: Genbank accession no. NM_001664; mouse RhoA mRNA: Genbank accession no. NM_016802; rat RhoA mRNA: Genbank accession no. NM_057132). Within the regions of homology thus identified, all possible contiguous sequences of 19 nucleotides were examined by further BLAST comparison for potential cross-reactivity of an siRNA comprising such sequence to other mRNA sequences present in humans. Only sequences with 3 or more mismatches to any other human mRNA or genomic sequence were chosen. The resulting set of 19 nt sequences is represented in the sense strand ribonucleotide sequences of the double-overhang iRNA agents given in Table 1.

In order to maximise the stability of the siRNAs for testing in biological media, particularly towards nucleolytic attack by endo- and exonucleases, the siRNAs were synthesized such that in the sense strands, all cytidine and uridine nucleotides comprise a 2'-O-methyl group, and in the antisense strand, all cytidines and uridines appearing in a sequence context of 5'-ca-3' or 5'-ua-3' comprise a 2'-O-methyl group.

To the same end, phosphorothioate linkages were introduced between 3'-terminal 5'-TT-3'-group thymidines. It has been our experience that the most active exonucleases in serum and other biological media relevant for the in vivo activity of siRNAs act by degrading siRNA strands 3'-5'. It has proven advantageous, and often sufficient, to replace the 2 penultimate nucleotides in the antisense strand by 2'-O-methyl-5'-phosphorothioate-modified nucleotides (e.g. the nucleotides in positions 21 and 22, counting 5' to 3', of a 23-nucleotide antisense strand); sometimes it is sufficient to modify only the penultimate nucleotide, or to use only 5'-phosphorothioate-modified nucleotides, or both. The sense strand may be protected in a similar fashion, and/or it may be 3'-conjugated to a tethered ligand via a phosphodiester or a phosphorothioate diester.

In addition to the sequences selected as described above, four siRNAs were synthesized which corresponded to four of those utilized by the authors of Ahmed, Z., et al, Mol Cell Neurosci. 2005, 28:509-23. AL-DP-5850 corresponds to RHO-A1 of Ahmed et al., supra, AL-DP-5851 to RHO-A2, AL-DP-5852 to RHO-A5 and AL-DP-5853 to RHO-A4 of Ahmed et al., supra.

Example 2
siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Glen Research, Sterling Va.) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification by anion exchange HPLC of the crude oligoribonucleotides were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The purified RNA solution was stored at −20° C. until use.

As a result of the synthesis strategy described above, all oligonucleotides synthesized as described above do not comprise a phosphate group on their 5'-most nucleotide.

Cholesterol was 3'-conjugated to siRNA as illustrated in FIG. 1. For the synthesis of these 3'-cholesterol-conjugated siRNAs, an appropriately modified solid support was used for RNA synthesis. The modified solid support was prepared as follows:

Diethyl-2-azabutane-1,4-dicarboxylate AA

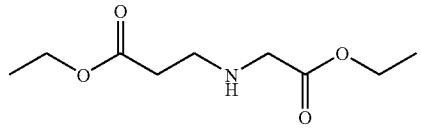

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until the completion of reaction was ascertained by TLC (19 h). After 19 h which it was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

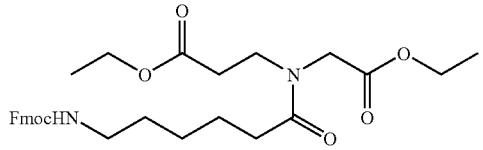

Fmoc-6-amino-hexanoic acid (9.12 g, 25.83 mmol) was dissolved in dichloromethane (50 mL) and cooled with ice. Diisopropylcarbodiimide (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. the completion of the reaction was ascertained by TLC. The reaction mixture was concentrated in vacuum and to the ethylacetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

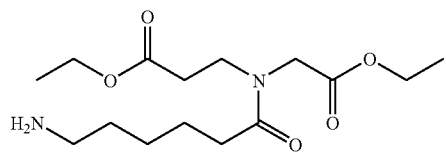

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated in vacuum and the residue water was added and the product was extracted with ethyl acetate. The crude product was purified by converting into hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

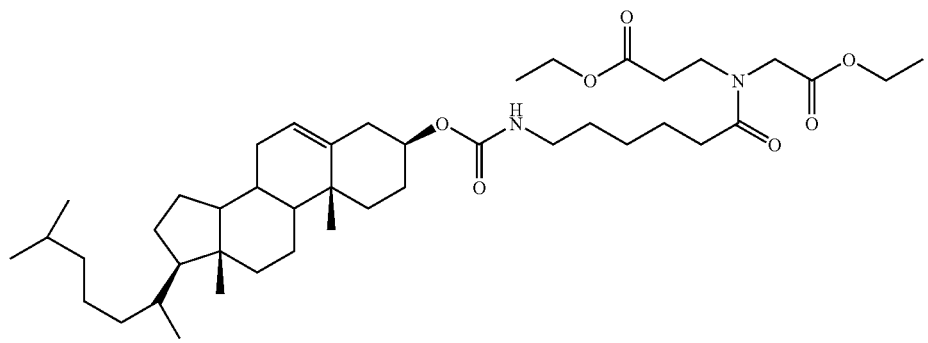

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

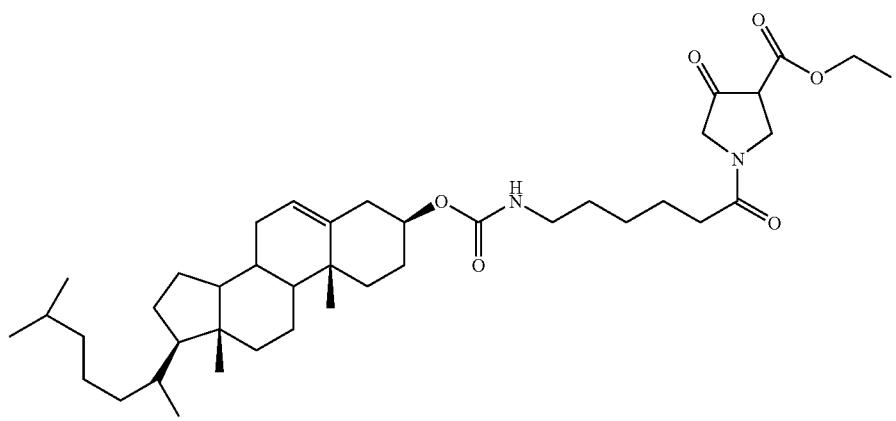

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to a residue. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

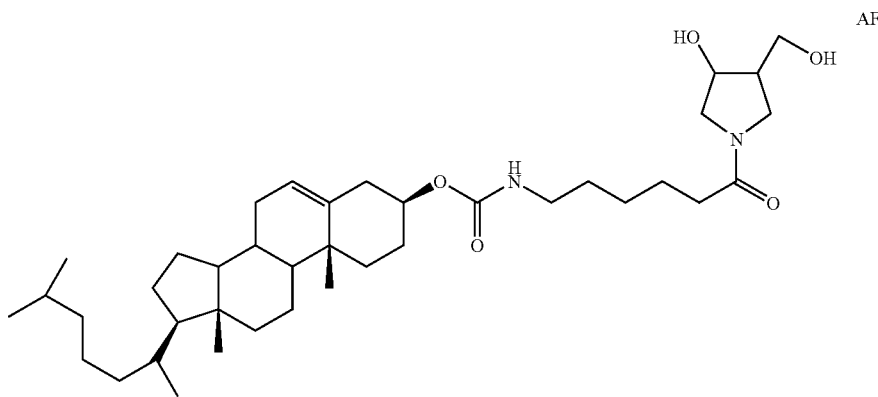

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated in vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

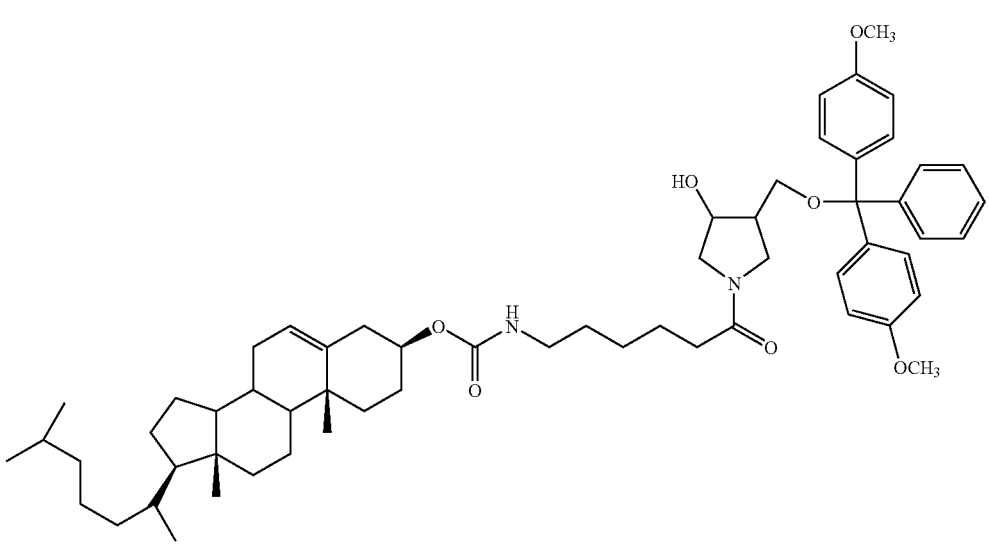

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated in vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15, 16,17-tetradecahydro-1H cyclopenta[a]phenanthren-3-yloxycarbonylamino]-hexanoyl}-pyrrolidin-3-yl) ester AH

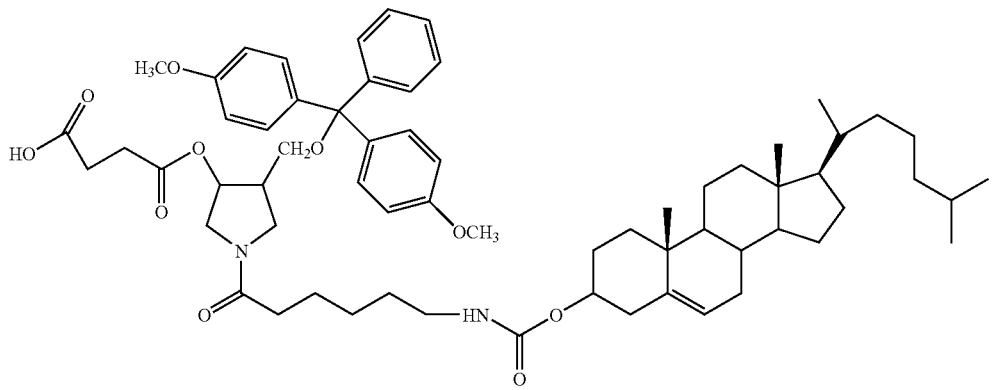

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG A1

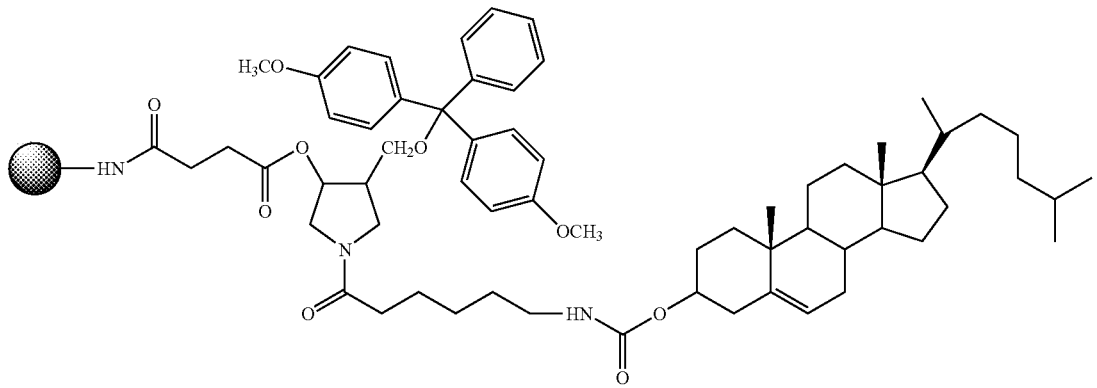

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using wrist-action shaker (5 mins). Long chain alkyl amine-CPG (LCAA-CPG) (1.5 g, 61 mm/g) was added. The suspension was agitated for 2 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement (37 mM/g).

The synthesis and structure of cholesterol conjugated RNA strands is illustrated in FIG. 1.

The siRNAs listed Table 3 were synthesized for activity screening.

TABLE 3 siRNAs specific for RhoA

| Agent number | Sense strand | SEQ ID NO. | Antisense strand | SEQ ID NO. | C. a. #[1] |
|---|---|---|---|---|---|
| AL-DP-5850 | gauuaugaccgucugaggcTT | 1081 | gccucagucggucauaaucTT | 1082 | n. a. |
| AL-DP-5851 | ggaucuucggaaugaugagTT | 1083 | cucaucauuccgaagauccTT | 1084 | n. a. |
| AL-DP-5852 | agaccaaagacggagugagTT | 1085 | cucacuccgucuuuggucuTT | 1086 | n. a. |
| AL-DP-5853 | ugaagcaggagccgguaaaTT | 1087 | uuuaccggcuccugcuucaTT | 1088 | n. a. |
| AL-DP-5972 | gcmumacmcmagumaumumumagaagcmTT | 1089 | gcuucumaaaumacuggumagcTT | 1090 | 6661 |
| AL-DP-5973 | cmumacmcmagumaumumumagaagcmcmTT | 1091 | ggcuucumaaaumacuggumagTT | 1092 | 6662 |
| AL-DP-5974 | gcmumgumaacmumacmumumumaumaacmTT | 1093 | guumaumaaaagumaguumacmagcTT | 1094 | 6712 |
| AL-DP-5975 | gumumacmumgumgumaaumumagumgcmTT | 1095 | gcmacumaauumacmacmagumaacTT | 1096 | 6751 |
| AL-DP-5976 | cmcmacmumumaaumgumaumgumumacmcmTT | 1097 | ggumaacmaumacmauumaaguggTT | 1098 | 6769 |
| AL-DP-5977 | cmagcmcmcmumgaumagumumumagaaTT | 1099 | uucumaaacumaucmagggcugTT | 1100 | 6521 |
| AL-DP-5978 | gcmcmcmumgaumagumumumagaaaaTT | 1101 | uuuucumaaacumaucmagggcTT | 1102 | 6523 |
| AL-DP-5979 | cmcmcmumgaumagumumumagaaaacmTT | 1103 | guuuucumaaacumaucmagggTT | 1104 | 6524 |
| AL-DP-5980 | gaumagumumumagaaaacmaumcmcmTT | 1105 | ggauguuuucumaaacumaucTT | 1106 | 6528 |
| AL-DP-5981 | umagumumumagaaaacmaumcmcmcmaTT | 1107 | ugggauguuuucumaaacumaTT | 1108 | 6530 |
| AL-DP-5982 | cmagacmumagaumgumagumaumumumTT | 1109 | aaaumacumacmaucumagucugTT | 1110 | 6790 |
| AL-DP-5983 | cmcmcmcmagacmumagaumgumagumaTT | 1111 | umacumacmaucumagucuggggTT | 1112 | 6787 |
| AL-DP-5984 | cmcmagacmumagaumgumagumaumumTT | 1113 | aaumacumacmaucumagucuggTT | 1114 | 6789 |
| AL-DP-5985 | cmcmcmagacmumagaumgumagumaumTT | 1115 | aumacumacmaucumagucugggTT | 1116 | 6788 |
| AL-DP-5986 | umgcmcmacmumumaaumgumaumgumumaTT | 1117 | umaacmaumacmauumaaguggcmaTT | 1118 | 6767 |
| AL-DP-5987 | umgcmumgumumumaumumaaumcmumumagTT | 1119 | cumaagauumaaumaaacmagcmaTT | 1120 | 6614 |
| AL-DP-5988 | umcmaumgumumagumumacmcmumumumaumaTT | 1121 | umaumaaggumaacumaacmaugaTT | 1122 | 6732 |
| AL-DP-5989 | cmcmagumumaaumumumumumcmcmaacmumTT | 1123 | aguuggaaaaauumaacuggTT | 1124 | 6832 |
| AL-DP-5990 | umacmcmumaagaumumacmaaaumcmaTT | 1125 | ugauuugumaaucuumaggumaTT | 1126 | 6650 |
| AL-DP-5991 | umcmumumgcmumacmcmagumaumumumagTT | 1127 | cumaaaumacuggumagcmaagaTT | 1128 | 6657 |
| AL-DP-5992 | umgumgumaaumumagumgcmcmacmumumumTT | 1129 | aaguggcmacumaauumacmacmaTT | 1130 | 6756 |
| AL-DP-5993 | aumcmumumumgcmumacmcmagumaumumumaTT | 1131 | umaaaumacuggumagcmaagauTT | 1132 | 6656 |
| AL-DP-5994 | cmumgumaacmumacmumumumumaumaacmumTT | 1133 | aguumaumaaaagumaguumacmagTT | 1134 | 6713 |
| AL-DP-5995 | gumgaaumumaggcmumgumaacmumaTT | 1135 | umaguumacmagccumaauucmacTT | 1136 | 6703 |

TABLE 3-continued siRNAs specific for RhoA

| Agent number | Sense strand | SEQ ID NO. | Antisense strand | SEQ ID NO. | C. a. #[1] |
|---|---|---|---|---|---|
| AL-DP-6176 | cmumacmcmagumaumumumagaagcmcmTT-Chol | 1137 | ggcuucumaaaumacuggumagTT | 1138 | 6662 |
| AL-DP-6177 | umgcmumgumumumaumumaaumcmumumagTT-Chol | 1139 | cumaagauumaaumaaacmagcmaTT | 1140 | 6614 |

[1] C. a. # = corresponding agent # in Table 2. The agent given under this agent number in Table 3 possesses the same core nucleotide sequence when nucleotide modifications, e.g. 2'-O-methyl modifications and phosphorothioate linkages, are disregarded

Example 3 siRNA Activity Testing

The ability of the iRNA agents represented in Table 3 to inhibit the expression of human RhoA was tested in human cell lines expressing the respective gene product from an expression construct, or in cell lines constitutively expressing the respective gene product. The iRNA agent is transfected into the cells, e.g., by transfection or electroporation, allowed to act on the cells for a certain time, e.g., 24 hours, and levels of RhoA expression were determined by measurement of RhoA mRNA concentrations in cell lysates. These expression levels were then compared to RhoA expression levels in cells treated equivalently but without addition of the iRNA agent, or to expression levels of housekeeping genes (e.g. GAPDH), and the ability of the iRNA agents represented in Table 3 to inhibit the expression of human RhoA thereby assessed.

Screening for Inhibition of RhoA Expression

One day before transfection, Neuroscreen-1 cells (Cellomics Inc., Pittsburgh, USA) were seeded at $1.5 \times 10^4$ cells/well on 96-well collagen-coated plates (Greiner Bio-One GmbH, Frickenhausen, Germany) in 100 µl of growth medium (RPMI 1640, 10% horse serum, 5% fetal calf serum, 100 u penicillin/100 µg/ml streptomycin, 2 mM L-glutamine, Biochrom AG, Berlin, Germany). Transfections were performed in triplicates. For each well 0.5 µl Lipofectamine2000 (Invitrogen GmbH, Karlsruhe, Germany) were mixed with 12 µl Opti-MEM (Invitrogen) and incubated for 15 min at room temperature. 2 µl of a 5 µM solution of siRNA in annealing buffer (20 mM sodium phosphate, pH 6.8; 100 mM sodium chloride) were mixed with 10.5 µl Opti-MEM per well, combined with the Lipofectamine2000-Opti-MEM mixture and again incubated for 15 minutes at room temperature. During this incubation, growth medium was removed from cells and replaced by 75 µl/well of fresh medium. The 25 µl solution of siRNA-Lipofectamine2000-complex were added, resulting in an overall 100 nM siRNA concentration in the 100 µl incubation volume, and the cells were incubated for 24 h at 37° C. and 5% $CO_2$ in a humidified incubator (Heraeus GmbH, Hanau).

mRNA levels in cell lysates were quantitated by a commercially available branched DNA hybridization assay (QuantiGene bDNA-kit, Genospectra, Fremont, USA). Cells were harvested by applying 50 µl additional growth medium and 75 µl of Lysis Mixture (from QuantiGene bDNA-kit) to each well and were lysed at 53° C. for 30 min. 50 µl of the lysates were incubated with probes specific to rat RhoA and rGAPDH (sequence of probes given in Table 4 and Table 5) according to the manufacturer's protocol for the QuantiGene bDNA kit assay. Finally, chemoluminescence was measured in a Victor2-Light (Perkin Elmer, Wiesbaden, Germany) as RLUs (relative light units) and values obtained with RhoA probes were normalized to the respective GAPDH values for each well. Mock transfected cells (following the same protocol except that no siRNA was added) served as controls and for comparison of mRNA levels.

Effective siRNAs from the screen were further characterized by establishment of dose response curves and calculation of $IC_{50}$ concentrations (the concentration at which 50% inhibition of gene expression would be observed). For dose response assessment, transfections were performed at the following concentrations: 100 nM, 33.3 nM, 11.1 nM, 3.7 nM, 1.2 nM, 0.4 nM, 137 pM, 46 pM, 15 pM, 5 pM and mock (no siRNA) by serially diluting the 5 µM siRNA stock solution with annealing buffer and using 2 µl of the diluted stock according to the above protocol. The $IC_{50}$ was determined by curve fitting using the computer software Xlfit using the following parameters: Dose Response One Site, 4 Parameter Logistic Model, fit=$(A+((B-A)/(1+(((10^\wedge C)/x)^\wedge D))))$, inv=$((10^\wedge C)/(((( B-A)/(y-A))-1)^\wedge(1/D)))$, res=$(y-fit)$.

TABLE 4

Rat RhoA probes

| Probe type[1] | Nucleotide sequence | SEQ ID NO. |
|---|---|---|
| CE | CCATTTTTCTGGGATGTTTTCTAAATTTTTCTCTTGGAAAGAAAGT | 1141 |
| CE | ACAGAAATGCTTGACTTCTGGAGTTTTTTCTCTTGGAAAGAAAGT | 1142 |
| CE | CTTCAGGTTTTACCGGCTCCTTTTTCTCTTGGAAAGAAAGT | 1143 |
| CE | CTGTTTGCCATATCTCTGCCTTTTTTTCTCTTGGAAAGAAAGT | 1144 |
| CE | TTGGTCTTTGCTGAACACTCCATTTTTCTCTTGGAAAGAAAGT | 1145 |

TABLE 4-continued

Rat RhoA probes

| Probe type[1] | Nucleotide sequence | SEQ ID NO. |
|---|---|---|
| CE | CCCGCGTCTAGCTTGCAGATTTTTCTCTTGGAAAGAAAGT | 1146 |
| LE | AGGATGATGGGCACATTTGGTTTTTAGGCATAGGACCCGTGTCT | 1147 |
| LE | GCCTTGTGTGCTCATCATTCCTTTTTAGGCATAGGACCCGTGTCT | 1148 |
| LE | TGCTTCATTTTGGCTAACTCCCTTTTTAGGCATAGGACCCGTGTCT | 1149 |
| LE | TGTACCCAAAAGCGCCAATCTTTTTAGGCATAGGACCCGTGTCT | 1150 |
| LE | GCAGCTCTCGTGGCCATCTTTTTTAGGCATAGGACCCGTGTCT | 1151 |
| LE | AGGCACCCCGACTTTTTCTTTTTTAGGCATAGGACCCGTGTCT | 1152 |
| BL | CTATCAGGGCTGTCGATGGAA | 1153 |
| BL | GAAGATCCTTCTTGTTCCCAACT | 1154 |
| BL | CAAAAACCTCTCTCACTCCGTCT | 1155 |

[1] CE = Capture Extender probe;
LE = Label Extender probe;
BL = blocking probe

TABLE 5

Rat GAPDH probes

| Probe type[1] | Nucleotide sequence | SEQ ID NO. |
|---|---|---|
| CE | CCAGCTTCCCATTCTCAGCCTTTTTCTCTTGGAAAGAAAGT | 1156 |
| CE | TCTCGCTCCTGGAAGATGGTTTTTTCTCTTGGAAAGAAAGT | 1157 |
| CE | CCCATTTGATGTTAGCGGGATTTTTCTCTTGGAAAGAAAGT | 1158 |
| CE | CGGAGATGATGACCCTTTTGGTTTTTCTCTTGGAAAGAAAGT | 1159 |
| LE | GATGGGTTTCCCGTTGATGATTTTTAGGCATAGGACCCGTGTCT | 1160 |
| LE | GACATACTCAGCACCAGCATCACTTTTTAGGCATAGGACCCGTGTCT | 1161 |
| LE | CCCAGCCTTCTCCATGGTGGTTTTTAGGCATAGGACCCGTGTCT | 1162 |
| BL | TTGACTGTGCCGTTGAACTTG | 1163 |
| BL | CCCCACCCTTCAGGTGAGC | 1164 |
| BL | GGCATCAGCGGAAGGGG | 1165 |

[1] CE = Capture Extender probe;
LE = Label Extender probe;
BL = blocking probe

Table 6 lists the agent number, the position of the nucleotide within the human RhoA mRNA sequence (Genbank accession number NM_001664) corresponding to the 5'-most nucleotide of the sense strand of the agent, the amount of total RhoA mRNA remaining in cells treated with the agent at 100 nM concentration in % of controls, and the IC$_{50}$ value for selected agents.

TABLE 6

Ability of siRNAs specific for RhoA to reduce RhoA mRNA levels in cultured cells

| Agent number | Pos. in mRNA[1] | Rem. RhoA mRNA at 100 nM agent, first screen | Rem. RhoA mRNA at 100 nM agent, second screen | IC$_{50}$ RhoA [nM] |
| --- | --- | --- | --- | --- |
| AL-DP-5850 | | | 73 ± 8% | 142 |
| AL-DP-5852 | | | 17 ± 4% | 3.1 |
| AL-DP-5853 | | | 18 ± 3% | 2.8 |
| AL-DP-5854 | | | 17 ± 1% | 4.2 |
| AL-DP-5972 | 986 | 30 ± 9% | 17 ± 2% | |
| AL-DP-5973 | 987 | 21 ± 2% | 15 ± 1% | 0.003 |
| AL-DP-5974 | 1179 | 44 ± 12% | 48 ± 2% | |
| AL-DP-5975 | 1395 | 33 ± 4% | 27 ± 10% | |
| AL-DP-5976 | 1413 | 26 ± 3% | 17 ± 2% | |
| AL-DP-5977 | 537 | n.d. | 30 ± 1% | |
| AL-DP-5978 | 539 | 58 ± 4% | 51 ± 1% | |
| AL-DP-5979 | 540 | 12 ± 2% | 15 ± 2% | 0.06 |
| AL-DP-5980 | 544 | 75 ± 3% | 95 ± 3% | |
| AL-DP-5981 | 546 | 17 ± 2% | 16 ± 1% | 0.13 |
| AL-DP-5982 | 1452 | 18 ± 2% | 22 ± 2% | 0.13 |
| AL-DP-5983 | 1449 | 37 ± 4% | 29 ± 3% | |
| AL-DP-5984 | 1451 | 26 ± 1% | 33 ± 4% | |
| AL-DP-5985 | 1450 | n.d. | 33 ± 1% | 0.37 |
| AL-DP-5986 | 1411 | 18 ± 1% | 22 ± 1% | 0.4 |
| AL-DP-5987 | 901 | 22 ± 5% | 10 ± 0% | 0.01 |
| AL-DP-5988 | 1376 | 17 ± 1% | 16 ± 1% | 0.34 |
| AL-DP-5989 | 1876 | 20 ± 1% | 25 ± 3% | 3.1 |
| AL-DP-5990 | 956 | 16 ± 2% | 17 ± 1% | 0.36 |
| AL-DP-5991 | 982 | 55 ± 5% | 33 ± 5% | |
| AL-DP-5992 | 1400 | 55 ± 6% | 55 ± 6% | |
| AL-DP-5993 | 981 | 32 ± 2% | 33 ± 3% | |
| AL-DP-5994 | 1180 | 23 ± 2% | 20 ± 1% | 0.24 |
| AL-DP-5995 | 1170 | 25 ± 2% | 26 ± 2% | 6.0 |
| AL-DP-6176 | 987 | | 14 ± 2% | 1.17 |
| AL-DP-6177 | 901 | | 19 ± 5% | 0.005 |

[1]Position of nucleotide within human Nogo-R mRNA corresponding to the 5'-most nucleotide of the sense strand of the agent In summary, agents AL-DP-5979, AL-DP-5990, AL-DP-5988, AL-DP-5981, AL-DP-5982, AL-DP-5986, AL-DP-5989 AL-DP-6176, and AL-DP-6177 were able to reduce the expression of RhoA mRNA by 80% or more, AL-DP-5973, AL-DP-5987, AL-DP-5994, AL-DP-5995, AL-DP-5976, AL-DP-5984, and AL-DP-5972 were able to reduce the expression of RhoA mRNA by 70% or more, AL-DP-5993, AL-DP-5975, and AL-DP-5983 were able to reduce the expression of RhoA mRNA by 60% or more, AL-DP-5974 was able to reduce the expression of RhoA mRNA by 50% or more, and AL-DP-5991, AL-DP-5992, and AL-DP-5978 were able to reduce the expression of RhoA mRNA by 40% or more. The high activity of AL-DP-6176 and AL-DP-6177 shows that a cholesteryl moiety may be conjugated to the 3'-end of the sense strand of an siRNA without significant loss of activity. AL-DP-6176 and AL-DP-6177 are identical to AL-DP-5973 and AL-DP-5987, respectively, except for the 3'-conjugated cholesteryl moiety on the sense strand.

Example 4

Stability Testing

In order to verify the stability of siRNAs in the biological matrix most relevant to their intended physiological application, cerebrospinal fluid (CSF), we established a method for determining the degradation half life of siRNAs in this medium. This method comprises the incubation of siRNAs with CSF followed by Proteinase K treatment of the CSF sample and the separation of CSF sample constituents on an HPLC.

The example below shows the analyses of CSF samples which were contacted with siRNAs in vitro. However, this method can equally be applied to biological samples ex vivo, i.e. obtained from a subject which was contacted with an siRNA in vivo.

Bovine CSF was obtained from a calf (Bos bovis), age 6 months (Prof. Dr. J. Rehage, University of Veterinary Medicine Hannover, Foundation, Hannover, Germany). Porcine CSF was pooled from 3 healthy weaner pigs (Sus scrofa domesticus), age 3-4 months (Prof. Dr. M. Wendt, University of Veterinary Medicine Hannover, Foundation, Hannover, Germany). Rat CSF was pooled from 20 male Sprague Dawley rats (*Rattus norvegicus*), 175-200 g in weight (Charles River Laboratories, L'Arbresle Cedex, France). Proteinase K (20 mg/ml) was obtained from peQLab (Erlangen, Germany; Cat.-No. 04-1075) and diluted 1:1 with deionized water (18.2 mΩ) to a final concentration of 10 mg/ml Proteinase K. Proteinase K Buffer (4.0 ml TRIS-HCl 1M pH 7.5, 1.0 ml EDTA 0.5M, 1.2 ml NaCl 5M, 4.0 ml SDS 10%) was prepared fresh and kept at 50° C. until use to avoid precipitation.

A 40 mer of poly(L-dT), (L-dT)$_{40}$ was obtained from Noxxon Pharma AG (Berlin, Germany) and used as an internal standard. Polymers of the L-enantiomers of nucleic acids show an extraordinary stability towards nucleolytic degradation (Klussman S, et al., Nature Biotechn. 1996, 14:1112) but otherwise very similar properties when compared to naturally occuring nucleic acids consisting of R-enantiomers.

Proteinase K Treatment of siRNA Incubation Samples

6 μl of a 50 μM solution of the respective siRNA in phosphate buffered saline (PBS, Sigma-Aldrich Chemie GmbH, Taufkirchen, Germany) was incubated with 54 μl CSF at 37° C. for 30 min, 1, 2, 4, 8, 16, 24 or 48 hours. To terminate the siRNA-degradation, 25 μl of Proteinase K buffer were added to incubation samples immediately after expiry of the respective incubation period, the mixture vortexed at highest speed for 5 s (Vortex Genie 2, Scientific Industries, Inc., Bohemia, N.Y., USA, cat. no. SI 0256), 8 μl Proteinase K (10 mg/ml) were added followed by vortexing for 5 s, and finally the mixture was incubated for 20 min in a thermomixer at 42° C. and 1050 rpm.

5 μl of a 50 μM solution (250 pmole) of (L-dT)$_{40}$ were added as an internal standard to each well, the solution was vortexed for 5 s, and the tube centrifuged for 1 min in a tabletop centrifuge to collect all droplets clinging to the inner surfaces of the wells at the bottom. The solution was transferred to a 96 well Captiva 0.2 μm filter plate (Varian, Germany, Cat. No. A5960002) and filtered by centrifugation at 21900 rcf for 45 min.

The incubation wells were washed with 47.5 μl deionized water (18.2 mΩ), the wash filtered through the Captiva Filter Unit at 21900 rcf for 15 min, and the wash step repeated.

Approximately 180 µl of the theoretical total volume of 200 µl are on average recovered after the second washing step.

Ion Exchange Chromatographic Separation of siRNA Single Strands from Each Other and from Degradation Products:

A Dionex BioLC HPLC-system equipped with inline-degasser, autosampler, column oven and fixed wavelength UV-detector (Dionex GmbH, Idstein, Germany) was used under denaturing conditions. Standard run parameters were:

| | | |
|---|---|---|
| Column: | Dionex DNA-Pac100; 4 × 250 mm | |
| Temperature: | 75° C. | |
| Eluent A: | 10 mM $NaClO_4$, 20 mM TRIS-HCl, 1 mM EDTA; 10% acetonitrile, pH = 8.0 | |
| Eluent B: | 800 mM $NaClO_4$, 20 mM TRIS-HCl, 1 mM EDTA; 10% acetonitrile, pH = 8.0 | |
| Detection: | @ 260 nm | |
| Gradient: | 0-1 min: | 10% B |
| | 1-11 min: | 10% –> 35% B |
| | 11-12 min: | 35% B –> 100% B |
| | 12-14 min: | 100% B –> 10% B |
| | 14-16 min: | 10% B for column reequilibration |
| Injection volume: | 20 µl | |

Where separation between the two strands of an siRNA was not satisfactory or a degradation fragment co-eluted with one strand, the chromatographic parameters were adjusted by changing temperature, pH, replacement of $NaClO_4$ by NaBr, the concentration of acetonitrile, and/or adjusting the slope of the eluent gradient until separation was achieved which allowed separate quantitation of the peaks from sense and antisense strand.

Peak areas for full length strands were obtained by integration of the UV detector signal using software supplied by the manufacturer of the instrument (Chromeleon 6.6; Dionex GmbH, Idstein, Germany).

Data Analysis:

Integrated sense strand, antisense strand, and internal standard peak areas were obtained for all samples and the normalization control.

A correction factor CF, accounting for liquid losses in the filtration and washing steps, was determined for every sample by calculating the ratio of experimental to theoretical internal standard peak area. The theoretical internal standard peak area is obtained, e.g. from a calibration curve of the internal standard obtained by injecting 50 µl each of a serial dilution of the 50 µM solution of $(L-dT)_{40}$ onto the HPLC column, and calculation of the theoretical peak area corresponding to 25 pmole $(L-dT)_{40}$ with the equation obtained by linear least square fit to the peak areas from the dilution series. The correction factor CF to be applied to the peak areas of the sense and antisense strand is the obtained as:

$$CF = PeakArea_{intStd}(theoretical)/PeakArea_{intStd}(Sample)$$

This treatment assumes that, by virtue of washing the filter twice, virtually complete recovery is achieved in the combined filtrates, and corrects for the variable volume of wash water retained in the filter, such that peak areas from different samples can be compared.

The peak areas obtained for the sense and antisense strand peaks for each time point are then multiplied with the correction factor CF to obtain Normalized Peak Areas ($NPA_{sense,t}$, $NPA_{antisense,t}$):

$$NPA_{sense\ or\ antisense,t} = (Peak\ Area_{sense\ or\ antisense,t}) \times CF$$

To obtain the relative amount of remaining Full Length Product (% FLP) for the sense and antisense strands at time t, the Normalized Peak Area for each strand at time t=0 min ($NPA_{sense,t=0}$, $NPA_{antisense,t=0}$) is set as 100%, and the NPAs from other time points are divided by these values.

$$\% FLP_{t=1,2,3\ldots n} = (NPA_{t=1,2,3\ldots n}/NPA_{t=0})*100$$

The value obtained from the control sample, where the siRNA was incubated with annealing buffer only, may serve as a control of the accuracy of the method. The % FLP for both strands should lie near 100%, within error margins, regardless of time of incubation.

The degradation half life $t_{1/2}$ may then be calculated for each strand, assuming first order kinetics, from the slope of a linear least square fit to a plot of ln(% FLP) versus time as:

$$t_{1/2} = \ln(0,5)/slope$$

Stability of siRNAs specific for NogoL and RhoA in rat, bovine and porcine CSF

Table 7 shows the results for select siRNAs of the determination of the relative amount of full length dsRNA present in porcine, rat, and bovine CSF, and PBS, after 48 h of incubation in the respective medium. In addition, the degradation half life was determined for the sense and antisense strands separately for some siRNAs.

TABLE 7

Stability of various siRNAs specific for NogoL and RhoA in rat, bovine and porcine CSF

| | % full length duplex present after 48 h in | | | | | | |
|---|---|---|---|---|---|---|---|
| Agent number | Porcine CSF | Rat CSF | Bovine CSF | PBS | Specific for | Modification[1] | C. a. #[2] |
| AL-DP-5973 | 95 | 3 | 95 | 100 | RhoA | 3/TTs | 6662 |
| AL-DP-5979 | 99 | | | 108 | RhoA | 3/TTs | 6524 |
| AL-DP-5981 | 96 | | | 103 | RhoA | 3/TTs | 6530 |
| AL-DP-5982 | 56 | | | 98 | RhoA | 3/TTs | 6790 |
| AL-DP-5986 | 100 | | | 105 | RhoA | 3/TTs | 6767 |
| AL-DP-5987 | 87 | | | 97 | RhoA | 3/TTs | 6614 |

TABLE 7-continued

Stability of various siRNAs specific for NogoL
and RhoA in rat, bovine and porcine CSF

| Agent number | % full length duplex present after 48 h in | | | | Specific for | Modification[1] | C. a. #[2] |
|---|---|---|---|---|---|---|---|
| | Porcine CSF | Rat CSF | Bovine CSF | PBS | | | |
| AL-DP-5988 | 41 | | | 99 | RhoA | 3/TTs | 6732 |
| AL-DP-5989 | 87 | | | 101 | RhoA | 3/TTs | 6832 |
| AL-DP-5990 | 76 | | | 92 | RhoA | 3/TTs | 6650 |

[1] 0 = no 2'-modifications; 1 = 5'-nucleotide in 5'-ua-3', 5'-uu-3', 5'-ca-3', and 5'-ug-3' motifs is 2'-modified in sense strand, 5'-nucleotide in 5'-ua-3' and 5'-ca-3' motifs is 2'-modified in antisense strand; 2 = 5'-nucleotide in 5'-ua-3', 5'-uu-3', 5'-ca-3', and 5'-ug-3' motifs is 2'-modified in sense and antisense strand; 3 = all pyrmidine nucleotides are 2'-modified in sense strand, 5'-nucleotide in 5'-ua-3' and 5'-ca-3' motifs is 2'-modified in antisense strand; 4 = all pyrimidine nucleotides are 2'-modified in sense strand, 5'-nucleotide in 5'-ua-3', 5'-uu-3', 5'-ca-3', and 5'-ug-3' motifs is 2'-modified in antisense strand; 5 = all pyrimidine nucleotides are 2'-modified in sense strand, no 2'-modifications in antisense strand; TT = 21 nucleotides and 3'-terminal TT single strand overhangs in sense and antisense strands; TTs = 21 nucleotides and 3'-terminal TT single strand overhangs in sense and antisense strands; 23 = 21 nucleotide sense, 23 nucleotide antisense strand, 2 nucleotide single strand overhang on 3'-end of antisense strand; 23s = 21 nucleotide sense, 23 nucleotide antisense strand, 2 nucleotide single strand overhang on 3'-end of antisense strand, nucleotides comprise 5'-phosphorothioate groups in positions 21 and 22 of antisense strand
[2] C. a. # = corresponding agent # in Table 2. The agent given under this agent number in Table 2 possesses the same core nucleotide sequence when nucleotide modifications, e.g. 2'-O-methyl modifications and phosphorothioate linkages, are disregarded As is evident from Table 7, the modification of siRNAs in select sites vulnerable to degradation can lead to agents with excellent properties in terms of activity and stability. For example, AL-DP-5871, AL-DP-5938, AL-DP-5963, AL-DP-5973, AL-DP-5979, AL-DP-5981, AL-DP-5986, AL-DP-5987, AL-DP-5989, and AL-DP-5990 all inhibit their respective target gene by more than 70% in the in vitro assays described above, and more than 70% full length duplex remain after incubation with porcine CSF for 48 h. However, there is some indication that rat CSF is more aggressive towards siRNAs than porcine or bovine CSF.

Example 5

Inhibition of RhoA Expression in Rat Primary Dorsal Root Ganglia (DRG) Cells in Culture The inhibition of RhoA expression was assessed in rat primary dorsal root ganglia (DRG) cells in culture in order to validate results obtained using Neuroscreen 1 cells as described above.

DRG cells were isolated from Sprague-Dawley rats at postnatal day 3 to 6. Rats were dissected and cells dissociated into single cells by addition of 1.3 ml (0.28 Wunsch units/ml) Liberase Blendzyme (Roche) in S-MEM (Invitrogen Gibco, Carlsbad Calif., USA) and incubated for 35 min at 37° C. The cell suspension was pre-plated on tissue-culture plates to remove non-neuronal cells. Neurons were then plated onto tissue-culture Biocoat™ PDL Poly-D-Lysine/Laminin 96 well plates (BD Biosciences, Bedford Mass., USA) in F12-HAM's Medium containing glutamine (Invitrogen Gibco, Carlsbad Calif., USA) with 5% fetal bovine serum (FBS, heat inactivated) and 5% horse serum (heat inactivated) (both Invitrogen Gibco, Carlsbad Calif., USA) supplemented with 50 ng/ml mouse nerve growth factor 2.5S (NGF; Promega Corp., Madison Wis., USA) and kept at 37° C., 5% $CO_2$ in a humidified incubator until transfection.

A rhoA-specific siRNA, agent number AL-DP-5987, was tested in DRG cultures at 200 nM concentration using Trans-Messenger™ Transfection reagent (Qiagen GmbH, Hilden, Germany, cat. no. 301525) which is based on a lipid formulation, specific RNA-condensing reagent (Enhancer R™) and an RNA-condensing buffer (Buffer EC-R™) keeping siRNA:Enhancer R™ ratio (μg:μl) constant at 1:2, and siRNA:Trans-Messenger™ ratio (μg:μl) constant at 1:12.

DRG neurons were transfected 24 h post-plating. For each well 0.52 μl Enhancer R™ were first mixed with 13.68 μl Buffer EC-R™. 0.8 μl of a 25 μM solution of AL-DP-5987 (0.26 μg) in annealing buffer (20 mM sodium phosphate, pH 6.8; 100 mM sodium chloride), or 0.8 μl of annealing buffer (siRNA-free control) were added and the mixture incubated for 5 min at RT. 3.12 μl TransMesssenger™ Transfection Reagent were diluted with 6.88 μl Buffer EC-R™, added to the mixture, and the mixture incubated for another 10 min at room temperature to allow transfection-complex formation. 75 μl serum free F12-HAM's Medium containing glutamine (Invitrogen Gibco, Carlsbad Calif., USA) supplemented with 50 ng/ml NGF 2.5S (Promega Corp., Madison Wis., USA) and 1:50 B27 supplement (Invitrogen Gibco, Carlsbad Calif., USA) were added to the transfection complexes and complete mixing achieved by gently pipetting up and down. The growth medium was removed from the DRG cells, and 90 μl of the above transfection complex mixture were added onto the cells. After 8 h of incubation at 37° C., 5% $CO_2$ in a humidified incubator supernatant was removed from the cells, fresh F12-HAM's medium containing glutamine supplemented with 5% FBS, 5% horse serum (both Invitrogen Gibco, Carlsbad Calif., USA), 50 ng/ml mouse NGF 2.5S (Promega Corp., Madison Wis., USA) and 1:100 Penicillin/Streptomycin (Invitrogen Gibco, Carlsbad Calif., USA) was added, the cells were incubated for another 16 h at 37° C., 5% $CO_2$ in a humidified incubator, and rhoA mRNA was quantified.

RhoA mRNA levels were measured using the Quanti-Gene™ bDNA kit (Genospectra, Fremont, USA) according to manufacturer's protocol. Briefly, the supernatant was removed from the DRG cells, and the cells were lysed by addition of 150 μl of Lysis Working Reagent (1 volume of Lysis Mixture plus 2 volumes of medium) and incubation at 52° C. for 30 min. 40 μl of the lysates were incubated at 52° C. for 40 min with the probe sets specific to rat RhoA and rat GAPDH given above in Table 4 and Table 5. Chemoluminescence was read on a Victor²-Light™ (PerkinElmer Life And Analytical Sciences, Inc., Boston Mass., USA) as Relative Light Units (RLU). RLU for RhoA were normalized to GAPDH RLU for each well. Normalized RhoA/GAPDH ratios were then compared to the siRNA-free control, which was set as 100%.

In several independent experiments, rhoA mRNA was reduced in primary DRG cells treated with AL-DP-5987 in culture consistently to 20-25% of rhoA mRNA levels found in the siRNA free controls.

We claim:

1. An iRNA agent comprising a sense strand and an antisense strand, wherein each strand is 21 nucleotides in length, and wherein the sequence of the sense strand is identical to the sense strand sequence of agent number 6662 (SEQ ID NO:557), and wherein the sequence of the antisense strand is identical to the antisense strand sequence of agent number 6662 (SEQ ID NO:558), and wherein every pyrimidine in the sense strand except for deoxythimidine is 2'-O-methyl modified, and wherein every 5'-nucleotide in 5'-ua-3' motifs in the antisense strand is 2'-O-methyl modified, and wherein the 21 nucleotides include two deoxythymidine nucleotides at the 3' end of each strand.

2. The iRNA agent of claim 1, wherein said deoxythymidine nucleotides at the 3' end of each strand comprise a phosphorothioate linkage.

3. The iRNA agent of claim 2, further comprising a cholesterol moiety conjugated to the deoxythymidine nucleotide at the 3'-end of the sense strand of the iRNA agent.

4. A composition, comprising:
  a.) an iRNA agent of claim 1, 2 or 3; and
  b.) a pharmaceutically acceptable carrier.

5. An isolated cell comprising an iRNA agent of claim 1, 2 or 3.

* * * * *